(12) United States Patent
Angibaud et al.

(10) Patent No.: US 9,737,544 B2
(45) Date of Patent: *Aug. 22, 2017

(54) COMPOUNDS

(71) Applicant: ASTEX THERAPEUTICS LIMITED, Cambridge (GB)

(72) Inventors: Patrick René Angibaud, Fontaine Bellenger (FR); Isabelle Noëlle Constance Pilatte, Louviers (FR); Olivier Alexis Georges Querolle, Saint Vigor (FR)

(73) Assignee: ASTEX THERAPEUTICS LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/000,304

(22) Filed: Jan. 19, 2016

(65) Prior Publication Data

US 2016/0213677 A1 Jul. 28, 2016

Related U.S. Application Data

(63) Continuation of application No. 14/404,188, filed as application No. PCT/GB2013/051428 on May 30, 2013, now Pat. No. 9,303,030.

(60) Provisional application No. 61/653,140, filed on May 30, 2012, provisional application No. 61/782,210, filed on Mar. 14, 2013.

(30) Foreign Application Priority Data

May 30, 2012 (GB) .................................. 1209609.5

(51) Int. Cl.
| | |
|---|---|
| *A61K 31/5377* | (2006.01) |
| *A61K 31/4375* | (2006.01) |
| *A61K 31/5025* | (2006.01) |
| *A61K 31/4985* | (2006.01) |
| *C07D 403/04* | (2006.01) |
| *A61K 45/06* | (2006.01) |
| *C07D 471/04* | (2006.01) |

(52) U.S. Cl.
CPC ...... *A61K 31/5377* (2013.01); *A61K 31/4375* (2013.01); *A61K 31/4985* (2013.01); *A61K 31/5025* (2013.01); *A61K 45/06* (2013.01); *C07D 403/04* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 2,940,972 A | 6/1960 | Roch | |
| 4,666,828 A | 5/1987 | Gusella | |
| 4,683,202 A | 7/1987 | Mullis | |
| 4,801,531 A | 1/1989 | Frossard | |
| 5,192,659 A | 3/1993 | Simons | |
| 5,272,057 A | 12/1993 | Smulson et al. | |
| 5,700,823 A | 12/1997 | Hirth et al. | |
| 5,882,864 A | 3/1999 | An et al. | |
| 6,218,529 B1 | 4/2001 | An et al. | |
| 6,271,231 B1 | 8/2001 | Bergstrand et al. | |
| 6,331,555 B1 | 12/2001 | Hirth et al. | |
| 7,432,279 B2 | 10/2008 | Green et al. | |
| 8,895,601 B2 | 11/2014 | Saxty et al. | |
| 9,145,367 B2 | 9/2015 | Tazi et al. | |
| 9,221,804 B2 | 12/2015 | Leonard et al. | |
| 9,290,478 B2 | 3/2016 | Saxty et al. | |
| 9,303,029 B2 | 4/2016 | Woodhead et al. | |
| 9,303,030 B2 * | 4/2016 | Angibaud ............ | C07D 403/04 |
| 9,309,241 B2 | 4/2016 | Angibaud et al. | |
| 9,309,242 B2 | 4/2016 | Berdini et al. | |
| 9,439,896 B2 | 9/2016 | Berdini et al. | |
| 9,447,098 B2 | 9/2016 | Saxty et al. | |
| 9,464,071 B2 | 10/2016 | Saxty et al. | |
| 9,493,426 B2 | 11/2016 | Angibaud et al. | |
| 9,527,844 B2 | 12/2016 | Angibaud et al. | |
| 2003/0207886 A1 | 11/2003 | Plucker et al. | |
| 2005/0261307 A1 | 11/2005 | Cai et al. | |
| 2005/0272728 A1 | 12/2005 | Altenbach et al. | |
| 2005/0272736 A1 | 12/2005 | Altenbach et al. | |
| 2007/0123494 A1 | 5/2007 | Seipelt et al. | |
| 2007/0149484 A1 | 6/2007 | Claus et al. | |
| 2008/0116789 A1 | 5/2008 | Yamaguchi et al. | |
| 2009/0054304 A1 | 2/2009 | Herbert et al. | |
| 2009/0118261 A1 | 5/2009 | Aquila et al. | |
| 2009/0221591 A1 | 9/2009 | Hartmann et al. | |

(Continued)

FOREIGN PATENT DOCUMENTS

| | | |
|---|---|---|
| CA | 2524525 | 12/2004 |
| CA | 2524948 | 12/2004 |

(Continued)

OTHER PUBLICATIONS

International Search Report for PCT/GB2013/051428 dated Oct. 1, 2013.
GB Search Report for GB1209609.5 dated Sep. 20, 2012.
Yan, Lin et al. "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.
Thompson, Andrew M. et al. "Synthesis and Structure—Activity Relationships of 7-Substituted 3-(2,6-Dichlorophenyl)-1,6-napthyridin-2(1H)-ones as Selective Inhibitors of pp60$^{c-src}$", *Journal of Medicinal Chemistry*, vol. 43, No. 16, 2000, pp. 3134-3147.

(Continued)

*Primary Examiner* — Samantha Shterengarts
(74) *Attorney, Agent, or Firm* — Heslin Rothenberg Farley & Mesiti P.C.

(57) ABSTRACT

The invention relates to new pyridopyrazine and naphthyridine derivative compounds, to pharmaceutical compositions comprising said compounds, to processes for the preparation of said compounds and to the use of said compounds in the treatment of diseases, e.g. cancer.

20 Claims, No Drawings

(56) References Cited

U.S. PATENT DOCUMENTS

| | | |
|---|---|---|
| 2010/0234347 A1 | 9/2010 | Dollinger et al. |
| 2013/0072457 A1 | 3/2013 | Saxty et al. |
| 2013/0267525 A1 | 10/2013 | Saxty et al. |
| 2014/0288053 A1 | 9/2014 | Berdini et al. |
| 2014/0296236 A1 | 10/2014 | Berdini et al. |
| 2015/0031669 A1 | 1/2015 | Woodhead et al. |
| 2015/0057293 A1 | 2/2015 | Angibaud et al. |
| 2015/0105368 A1 | 4/2015 | Saxty et al. |
| 2015/0239883 A1 | 8/2015 | Angibaud et al. |
| 2015/0291589 A1 | 10/2015 | Saxty et al. |
| 2016/0031856 A1 | 2/2016 | Saxty et al. |
| 2016/0075666 A1 | 3/2016 | Angibaud et al. |
| 2016/0108034 A1 | 4/2016 | Angibaud et al. |
| 2016/0220564 A1 | 8/2016 | Woodhead et al. |
| 2016/0235744 A1 | 8/2016 | Berdini et al. |
| 2016/0311800 A1 | 10/2016 | Saxty et al. |
| 2017/0000781 A1 | 1/2017 | Berdini et al. |
| 2017/0000796 A1 | 1/2017 | Saxty et al. |
| 2017/0100406 A1 | 4/2017 | Jovcheva et al. |
| 2017/0101396 A1 | 4/2017 | Vermeulen et al. |
| 2017/0105978 A1 | 4/2017 | Angibaud et al. |
| 2017/0119763 A1 | 5/2017 | Jovcheva et al. |

FOREIGN PATENT DOCUMENTS

| | | |
|---|---|---|
| CN | 1128496 A | 8/1996 |
| CN | 102036963 A | 4/2011 |
| EP | 0544445 A2 | 6/1993 |
| EP | 1001946 | 5/2000 |
| EP | 1990342 | 11/2008 |
| EP | 2332939 | 6/2011 |
| EP | 2650293 A1 | 10/2013 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 95/19169 A2 | 7/1995 |
| WO | 98/54156 A1 | 12/1998 |
| WO | 99/17759 A2 | 4/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 2004/006355 A2 | 1/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |
| WO | 2006/066361 A1 | 6/2006 |
| WO | 2006084338 A1 | 8/2006 |
| WO | 2006/092430 A1 | 9/2006 |
| WO | 2006124354 A2 | 11/2006 |
| WO | 2007/003419 A1 | 1/2007 |
| WO | 2007054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2008/003702 A2 | 1/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A2 | 7/2008 |
| WO | 2008/138878 A2 | 11/2008 |
| WO | 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009/064835 A1 | 5/2009 |
| WO | 2009/137378 A1 | 11/2009 |
| WO | 2009/141386 A1 | 11/2009 |
| WO | 2010059771 A1 | 5/2010 |
| WO | 2010/084152 A1 | 7/2010 |
| WO | 2010088177 A1 | 8/2010 |
| WO | 2010129570 A1 | 11/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013/179033 A1 | 12/2013 |
| WO | 2013/179034 A1 | 12/2013 |
| WO | 2014/174307 A1 | 10/2014 |
| WO | 2015144803 A1 | 10/2015 |
| WO | 2015144804 A1 | 10/2015 |
| WO | 2015144808 A1 | 10/2015 |
| WO | 2016128411 A1 | 8/2016 |

OTHER PUBLICATIONS

Berge, Stephen M. et al. "Pharmaceutical Salts", *Journal of Pharmaceutical Sciences*, vol. 66, No. 1, 1977, pp. 1-19.

Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.

Knights, Victoria et al. "De-regulated FGF receptors as therapeutic targets in cancer", *Pharmacology & Therapeutics*, 2010; vol. 125(1), pp. 105-117.

Korc, M. et al. "The Role of Fibroblast Growth Factors in Tumor Growth", *Current Cancer Drug Targets*, vol. 9(5), 2009, pp. 639-651.

Angerer, Lynne M. et al. "Demonstration of Tissue-Specific Gene Expression by in Situ Hybridization", *Methods in Enzymology*, vol. 152, 1987, pp. 649-661.

Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, Maxine and Rogers, Peter A.W. "VEGF, VEGFR-1, VEGFR-2, Microvessel Density and Endothelial Cell Proliferation in Tumours of the Ovary", *Int. J. Cancer (Pred. Oncol.)*, vol. 84(2), 1999, pp. 101-108.

Zhou, Wenjun et al., "A Structure-Guided Approach to Creating Covalent FGFR Inhibitors", *Chemistry & Biology*, vol. 17, pp. 285-295 (2010).

Avendaño, C., et al., "Drugs That Inhibit Signalling Pathways for Tumor Cell Growth and Proliferation", *Medicinal Chemistry of Anticancer Drugs*, pp. 251-305 (2008).

(56) References Cited

OTHER PUBLICATIONS

Garuti, L., et al., Irreversible Protein Kinase Inhibitors, *Current Medicinal Chemistry*, vol. 18, No. 20, Jul. 1, 2011, pp. 2981-2994.
Vippagunta, S.R. et al., Crystalline Solids, *Advanced Drug Delivery Reviews*, vol. 48, pp. 3-26 (2001).
Jordan, V.C., Tamoxifen: A Most Unlikely Pioneering Medicine, *Nature Reviews: Drug Discovery*, vol. 2, pp. 205-213 (2003).
Hackam, D.G., et al., Translation of Research Evidence From Animals to Humans, *JAMA*, vol. 14, pp. 1731-1732 (2006).
"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).
V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).
"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).
Dorwald, F.Z., Side Reactions in Organic Synthesis: A Guide to Successful Synthesis Design, Weinheim:WILEY-VCH Verlag GmbH & Co. KGaA, 2005, ISBN: 3-527-31021.5.
Lima, L.M., et al., "Bioisosterism: A Useful Strategy for Molecular Modification and Drug Design", *Current Medical Chemistry*, vol. 12(1), pp. 23-49 (2005).
Patani, G.A., et al., "Bioisosterism: A Rational Approach in Drug Design", *Chem. Rev.* vol. 96, pp. 3147-3176 (1996).
Dieci, M.V., et al., Fibroblast Growth Factor Receptor Inhibitors as a Cancer Treatment: From a Biologic Rationale to Medical Perspectives, Cancer Discovery, vol. 3, No. 3, pp. 264-279 (Feb. 2013).
Gallick, G.E., et al., Small-molecule protein tyrosine kinase inhibitors for the treatment of metastatic prostate cancer, Future Medicinal Chemistry, vol. 4, No. 1, pp. 107-119 (Jan. 2012).
Study to Assess the Relative Bioavailability of Orally Administered JNJ-42756493 Tablet Versus JNJ-42756493 Capsule in Healthy Participants, ClinicalTrials.gov, pp. 1-4 (2014).
Matsuda, Y., et al., Fibroblast Growth Factor Receptor-2 IIIc as a Novel Molecular Target in Colorectal Cancer, Current Colorectal Cancer Reports, vol. 10, No. 1, pp. 20-26 (2014).
Carneiro, B.A., et al., Emerging therapeutic targets in bladder cancer, Cancer Treatment Reviews, vol. 41, No. 2, pp. 170-178 (2015).
Fujita, M., et al., Generation of Formaldehyde by Pharmaceutical Excipients and Its Absorption by Meglumine, Chem. Pharm. Bull, vol. 57, No. 10, pp. 1096-1099 (2009).
Adcock, J., et al., Diversity oriented synthesis: substitution at C5 in unreactive pyrimidines by Claisen rearrangement and reactivity in nucleophilic substitution at C2 and C4 in pteridines and pyrido[2,3-d]pyrimidines, Tetrahedron, vol. 67, pp. 3226-3237 (2011).
Database Caplus, Grina, et al., Preparation of oxohydroquinazolinylaminophenylpropanesulfonamide derivatives and analogs for use as Raf inhibitors, Document No. 157:465574, Accession No. 2012:1301209 (2012).
Liang, G., et al., "Small molecule inhibition of fibroblast growth factor receptors in cancer", Cytokine & Growth Factor Reviews, vol. 24, pp. 467-475 (2013).
Golub, T.R., et al., "Molecular Classification of Cancer: Class Discovery and Class Prediction by Gene Expression Monitoring", Science, vol. 286, pp. 531-537 (1999).
Greulich, H., et al., "Targeting mutant fibroblast growth factor receptors in cancer", Trends in Molecular Medicine, vol. 17, No. 5, pp. 283-292 (2011).
Freshney, R.I., "Culture of Animal Cells, A Manual of Basic Technique", Published by Alan R. Liss, Inc, New York, pp. 1-6 (1983).
Cohen, P., "The development and therapeutic potential of protein kinase inhibitors", Current Opinion in Chemical Biology, vol. 3, pp. 459-465 (1999).
Cecil Textbook of Medicine, edited by Bennet, J.C., and Plum, F., 20th edition, vol. 1, pp. 1004-1010 (1996).
Hynes, N.E., et al., "Potential for Targeting the Fibroblast Growth Factor Receptors in Breast Cancer", Cancer Research, vol. 70, pp. 5199-5202 (2010).
Neidle, S., "Cancer Drug Design and Discovery", Elsevier/Academic Press, pp. 427-431 (2008).
Dermer, G.B., "Another Anniversary for the War on Cancer", Biotechnology, vol. 12, p. 320 (1994).
Katoh, Y., et al., "FGFR2-related pathogenesis and FGFR2-targeted therapeutics (Review)", International Journal of Molecular Medicine, vol. 23, pp. 307-311 (2009).
Jain, V.K., et al., "Challenges and opportunities in the targeting of fibroblast growth factor receptors in breast cancer", Breast Cancer Research, vol. 14, No. 208, pp. 1-9 (2012).

\* cited by examiner

COMPOUNDS

CROSS REFERENCE TO RELATED APPLICATIONS

This application is a continuation of U.S. application Ser. No. 14/404,188, filed on Nov. 26, 2014, which is a national stage filing under section 371 of International Application No. PCT/GB2013/051428, filed on May 30, 2013, and published in English on Dec. 5, 2013 as WO 2013/179034, and claims priority to U.S. Provisional Application No. 61/653,140, filed on May 30, 2012, to U.S. Provisional Application No. 61/782,210, filed on Mar. 14, 2013, and to British Application No. 1209609.5, filed on May 30, 2012. The entire disclosures of each of the prior applications are hereby incorporated herein by reference.

FIELD OF THE INVENTION

The invention relates to new pyridopyrazine and naphthyridine derivative compounds, to pharmaceutical compositions comprising said compounds, to processes for the preparation of said compounds and to the use of said compounds in the treatment of diseases, e.g. cancer.

SUMMARY OF THE INVENTION

According to a first aspect of the invention there is provided compounds of formula (I-A) or (I-B):

including any tautomeric or stereochemically isomeric form thereof, wherein
for (I-A)
$X_1$ is N, $X_2$ is N and $X_3$ is CH; or
$X_1$ is $CR^{3d}$, $X_2$ is N and $X_3$ is CH; or
$X_1$ is $CR^{3d}$, $X_2$ is $CR^{3d}$ and $X_3$ is N;
for (I-B)
$X_1$ is N or $CR^{3d}$;
each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo-$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ and —C(=O)—$NR^7R^8$; or when two $R^2$ groups are attached to adjacent carbon atoms they may be taken together to form a radical of formula:

—O—(C($R^{17}$)$_2$)$_p$—O—;

—X—CH=CH—; or

—X—CH=N—;

wherein $R^{17}$ represents hydrogen or fluorine, p represents 1 or 2 and
X represents O or S;
D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;
$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl,
$C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, —C(=O)—$R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;
$R^{3a}$ represents —$NR^{10}R^{11}$, hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo-$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano-$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with
$C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—NR$^{10}$R$^{11}$, $C_{1-6}$alkyl substituted with —O—C(=O)—NR$^{10}$R$^{11}$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NR$^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, R$^{13}$, $C_{1-6}$alkyl substituted with —P(=O)(OH)$_2$ or $C_{1-6}$alkyl substituted with —P(=O)(OC$_{1-6}$alkyl)$_2$; provided that for a compound of formula (I-B), R$^{3a}$ may not represent —NR$^{10}$R$^{11}$;

R$^{3b}$ represents hydrogen or hydroxyl; provided that if R$^{3a}$ represents —NR$^{10}$R$^{11}$, then R$^{3b}$ represents hydrogen; or for a compound of formula (I-A), R$^{3a}$ and R$^{3b}$ may also be taken together to form =O, to form =NR$^{10}$, to form cyclopropyl together with the carbon atom to which they are attached, to form =CH—C$_{0-4}$alkyl substituted with R$^{3c}$, or to form

wherein ring A is a monocyclic 5 to 7 membered saturated heterocycle containing one heteroatom selected from N, O or S, said heteroatom not being positioned in alpha position of the double bond, wherein ring A is optionally being substituted with cyano, $C_{1-4}$alkyl, hydroxy$C_{1-4}$alkyl, H$_2$N—$C_{1-4}$ alkyl, (C$_{1-4}$alkyl)NH—$C_{1-4}$alkyl, (C$_{1-4}$alkyl)$_2$N—$C_{1-4}$alkyl, (haloC$_{1-4}$alkyl)NH—$C_{1-4}$alkyl, $C_{1-4}$alkoxy$C_{1-4}$alkyl, —C(=O)—NH$_2$, —C(=O)—NH(C$_{1-4}$alkyl), —C(=O)—N(C$_{1-4}$alkyl)$_2$;

R$^{3c}$ represents hydrogen, hydroxyl, $C_{1-6}$alkoxy, R$^9$, —NR$^{10}$R$^{11}$, —C(=O)—NR$^{14}$R$^{15}$, cyano, —C(=O)—$C_{1-6}$alkyl or —CH(OH)—$C_{1-6}$alkyl;

R$^{3d}$ represents hydrogen, chlorine, hydroxyl, or $C_{1-6}$alkoxy;

R$^4$ and R$^5$ each independently represent hydrogen, $C_{1-6}$alkyl, $C_{1-6}$alkyl substituted with —NR$^{14}$R$^{15}$, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—NR$^{14}$R$^{15}$, —C(=O)—NR$^{14}$R$^{16}$, —C(=O)—O—$C_{1-6}$alkyl, —C(=O)—R$^{13}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—NR$^{14}$R$^{15}$, R$^{13}$ or $C_{1-6}$alkyl substituted with R$^{13}$;

R$^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-4}$alkyl-O—C(=O)—, —NR$^{14}$R$^{15}$, —C(=O)—NR$^{14}$R$^{15}$, $C_{1-6}$alkyl substituted with —NR$^{14}$R$^{15}$, $C_{1-6}$alkyl substituted with —C(=O)—NR$^{14}$R$^{15}$, —S(=O)$_2$—$C_{1-6}$alkyl, —S(=O)$_2$-halo$C_{1-6}$alkyl, —S(=O)$_2$—NR$^{14}$R$^{16}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—NR$^{14}$R$^{15}$;

R$^7$ and R$^8$ each independently represent hydrogen, $C_{1-6}$alkyl, hydroxy$C_{1-6}$alkyl, halo$C_{1-6}$alkyl, hydroxyhalo-$C_{1-6}$alkyl or $C_{1-6}$alkoxy$C_{1-6}$alkyl;

R$^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl, substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —NR$^{14}$R$^{15}$, —C(=O)—NR$^{14}$R$^{15}$, $C_{1-4}$alkyl substituted with —NR$^{14}$R$^{15}$, $C_{1-4}$alkyl substituted with —C(=O)—NR$^{14}$R$^{15}$, $C_{1-4}$alkoxy, —S(=O)$_2$—$C_{1-4}$alkyl, —S(=O)$_2$-halo$C_{1-4}$alkyl, —S(=O)$_2$—NR$^{14}$R$^{15}$, $C_{1-4}$alkyl substituted with —S(=O)$_2$—NR$^{14}$R$^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—NR$^{14}$R$^{15}$, R$^{13}$, —C(=O)—R$^{13}$, $C_{1-4}$alkyl substituted with R$^{13}$, phenyl optionally substituted with R$^{16}$, phenylC$_{1-6}$ alkyl wherein the phenyl is optionally substituted with R$^{16}$, a 5 or 6-membered aromatic monocyclic heterocyclyl containing at least one heteroatom selected from N, O or S wherein said heterocyclyl is optionally substituted with R$^{16}$;

or when two of the substituents of R$^9$ are attached to the same atom, they may be taken together to form a 4 to 7-membered saturated monocyclic heterocyclyl containing at least one heteroatom selected from N, O or S;

R$^{10}$ and R$^{11}$ each independently represent hydrogen, carboxyl, $C_{1-6}$alkyl, cyano$C_{1-6}$alkyl, $C_{1-6}$ alkyl substituted with —NR$^{14}$R$^{15}$, $C_{1-6}$alkyl substituted with —C(=O)—NR$^{14}$R$^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, R$^6$, $C_{1-6}$alkyl substituted with R$^6$, —C(=O)—R$^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl, substituted with —Si(CH$_3$)$_3$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$ alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with carboxyl, or $C_{1-6}$alkyl substituted with —NH—S(=O)$_2$—NR$^{14}$R$^{15}$;

R$^{12}$ represents hydrogen or $C_{1-4}$alkyl optionally substituted with $C_{1-4}$alkoxy;

R$^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, halo$C_{1-6}$alkyl, =O, cyano, —C(=O)—$C_{1-6}$alkyl, $C_{1-6}$alkoxy, or —NR$^{14}$R$^{15}$;

R$^{14}$ and R$^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$ alkyl)amino;

R$^{16}$ represents hydroxyl, halogen, cyano, $C_{1-4}$alkoxy, —NR$^{14}$R$^{15}$ or —C(=O)NR$^{14}$R$^{15}$;

n independently represents an integer equal to 0, 1, 2, 3 or 4;

the N-oxides thereof, the pharmaceutically acceptable salts thereof or the solvates thereof.

WO1999/17759, WO2006/092430, WO2008/003702, WO01/68047, WO2005/007099, WO2004/098494, WO2009/141386, WO 2004/030635, WO 2008/141065, WO 2011/026579, WO 2011/028947, WO 00/42026, WO2008/138878, WO2004/104003, WO2004/104002, WO2007/079999, WO2007/054556, WO2010/084152, US2005/0272736, US2005/0272728, US2007/0123494, WO2011/135376, WO2012/073017, WO2013/061074, WO2013/061081, WO2013/061077 and WO2013/061080 which each disclose a series of heterocyclyl derivatives.

DETAILED DESCRIPTION OF THE INVENTION

Unless the context indicates otherwise, references to formula (I) in all sections of this document (including the uses, methods and other aspects of the invention) include references to all other sub-formula (e.g. I-A, I-B, I-C, I-D, I-E, I-F, I-G), sub-groups, preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term 'halo' or 'halogen' as used herein refers to a fluorine, chlorine, bromine or iodine atom.

The term '$C_{1-4}$alkyl', or '$C_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-4}$alkenyl' or '$C_{2-6}$alkenyl' as used herein as a group or part of a group refers to a linear or branched hydrocarbon group containing from 2 to 4 or 2 to 6 carbon atoms and containing a carbon carbon double bond.

The term '$C_{2-4}$alkynyl' or '$C_{2-6}$alkynyl' as used herein as a group or part of a group refers to a linear or branched hydrocarbon group having from 2 to 4 or 2 to 6 carbon atoms and containing a carbon carbon triple bond.

The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-4}$alkoxy$C_{1-4}$alkyl' or '$C_{1-6}$alkoxy$C_{1-6}$alkyl' as used herein as a group or part of a group refers to a $C_{1-4}$alkyl-O—$C_{1-4}$alkyl group or a $C_{1-6}$alkyl-O—$C_{1-6}$alkyl group wherein $C_{1-4}$alkyl and $C_{1-6}$alkyl are as defined herein. Examples of such groups include methoxyethyl, ethoxyethyl, propoxymethyl, butoxypropyl, and the like.

The term '$C_{3-8}$cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-8}$cycloalkenyl' as used herein refers to a monocyclic hydrocarbon ring of 3 to 8 carbon atoms having a carbon carbon double bond.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy-$C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo$C_{1-4}$alkyl' or 'halo$C_{1-6}$alkyl' therefore include monohalo$C_{1-4}$alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'hydroxyhalo$C_{1-4}$alkyl' or 'hydroxyhalo$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group and one or more than one hydrogen atom is replaced with a halogen. The term 'hydroxyhalo$C_{1-4}$alkyl' or 'hydroxyhalo$C_{1-6}$alkyl' therefore refers to a $C_{1-4}$alkyl or $C_{1-6}$alkyl group wherein one, two, three or more hydrogen atoms are replaced with a hydroxyl group and one, two, three or more hydrogen atoms are replaced with a halogen.

The term 'hydroxy$C_{1-4}$alkoxy' or 'hydroxy$C_{1-6}$alkoxy' as used herein as a group or part of a group refers to an —O—$C_{1-4}$alkyl group or an —O—$C_{1-6}$alkyl group wherein the $C_{1-4}$alkyl and $C_{1-6}$alkyl group is as defined above and one or more than one hydrogen atom of the $C_{1-4}$alkyl or $C_{1-6}$alkyl group is replaced with a hydroxyl group. The term 'hydroxy$C_{1-4}$alkoxy' or 'hydroxy$C_{1-6}$alkoxy' therefore include monohydroxy$C_{1-4}$alkoxy, monohydroxy$C_{1-6}$alkoxy and also polyhydroxy$C_{1-4}$alkoxy and polyhydroxy-$C_{1-6}$alkoxy. There may be one, two, three or more hydrogen atoms replaced with a hydroxyl group so the hydroxy-$C_{1-4}$alkoxy or hydroxy$C_{1-6}$alkoxy may have one, two, three or more hydroxyl groups. Examples of such groups include hydroxymethoxy, hydroxyethoxy, hydroxypropoxy and the like.

The term 'halo$C_{1-4}$alkoxy' or 'halo$C_{1-6}$alkoxy' as used herein as a group or part of a group refers to a —O—$C_{1-4}$alkyl group or a —O—$C_{1-6}$alkyl group as defined herein wherein one or more than one hydrogen atom is replaced with a halogen. The terms 'halo$C_{1-4}$alkoxy' or 'halo$C_{1-6}$alkoxy' therefore include monohalo$C_{1-4}$alkoxy, monohalo$C_{1-6}$alkoxy and also polyhalo$C_{1-4}$alkoxy and polyhalo$C_{1-6}$alkoxy. There may be one, two, three or more hydrogen atoms replaced with a halogen, so the halo$C_{1-4}$alkoxy or halo$C_{1-6}$alkoxy may have one, two, three or more halogens. Examples of such groups include fluoroethyloxy, difluoromethoxy or trifluoromethoxy and the like.

The term 'hydroxyhaloC$_{1-4}$alkoxy' as used herein as a group or part of a group refers to an —O—C$_{1-4}$alkyl group wherein the C$_{1-4}$alkyl group is as defined herein and wherein one or more than one hydrogen atom is replaced with a hydroxyl group and one or more than one hydrogen atom is replaced with a halogen. The term 'hydroxyhaloC$_{1-4}$alkoxy' therefore refers to a —O—C$_{1-4}$alkyl group wherein one, two, three or more hydrogen atoms are replaced with a hydroxyl group and one, two, three or more hydrogen atoms are replaced with a halogen.

The term 'haloC$_{1-4}$alkoxyC$_{1-4}$alkyl' as used herein as a group or part of a group refers to a C$_{1-4}$alkyl-O—C$_{1-4}$alkyl group wherein C$_{1-4}$alkyl is as defined herein and wherein in one or both of the C$_{1-4}$alkyl groups one or more than one hydrogen atom is replaced with a halogen. The term 'halo-C$_{1-4}$alkoxyC$_{1-4}$alkyl' therefore refers to a C$_{1-4}$alkyl-O—C$_{1-4}$alkyl group wherein in one or both of the C$_{1-4}$alkyl groups one, two, three or more hydrogen atoms are replaced with a halogen and wherein C$_{1-4}$alkyl is as defined herein. Preferably, in one of the C$_{1-4}$alkyl groups one or more than one hydrogen atom is replaced with a halogen. Preferably, haloC$_{1-4}$alkoxyC$_{1-4}$alkyl means C$_{1-4}$alkyl substituted with haloC$_{1-4}$alkoxy.

The term 'hydroxyhaloC$_{1-4}$alkoxyC$_{1-4}$alkyl' as used herein refers to a C$_{1-4}$alkyl-O—C$_{1-4}$alkyl group wherein C$_{1-4}$alkyl is as defined herein and wherein in one or both of the C$_{1-4}$alkyl groups one or more than one hydrogen atom is replaced with a hydroxyl group and one or more than one hydrogen atom is replaced with a halogen. The terms 'hydroxyhaloC$_{1-4}$alkoxyC$_{1-4}$alkyl' therefore refers to a C$_{1-4}$alkyl-O—C$_{1-4}$alkyl group wherein in one or both of the C$_{1-4}$alkyl groups one, two, three or more hydrogen atoms are replaced with a hydroxyl group and one, two, three or more hydrogen atoms are replaced with a halogen and wherein C$_{1-4}$alkyl is as defined herein.

The term 'hydroxyC$_{2-6}$alkenyl' as used herein refers to a C$_{2-6}$alkenyl group wherein one or more than one hydrogen atom is replaced with a hydroxyl group and wherein C$_{2-6}$alkenyl is as defined herein.

The term 'hydroxyC$_{2-6}$alkynyl' as used herein refers to a C$_{2-6}$alkynyl group wherein one or more than one hydrogen atom is replaced with a hydroxyl group and wherein C$_{2-6}$alkynyl is as defined herein.

The term phenylC$_{1-6}$alkyl as used herein refers to a C$_{1-6}$alkyl group as defined herein which is substituted with one phenyl group.

The term cyanoC$_{1-4}$alkyl or cyanoC$_{1-6}$alkyl as used herein refers to a C$_{1-4}$alkyl or C$_{1-6}$alkyl group as defined herein which is substituted with one cyano group.

The term "heterocyclyl" as used herein shall, unless the context indicates otherwise, include both aromatic and non-aromatic ring systems. Thus, for example, the term "heterocyclyl group" includes within its scope aromatic, non-aromatic, unsaturated, partially saturated and fully saturated heterocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to heterocyclyl groups, the heterocyclyl ring can, unless the context indicates otherwise, be optionally substituted (i.e. unsubstituted or substituted) by one or more substituents as discussed herein.

The heterocyclyl groups can be heteroaryl groups having from 5 to 12 ring members, more usually from 5 to 10 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 0, 1, 2 or 3 ring heteroatoms;
  c) a pyrimidine ring fused to a 5- or 6-membered ring containing 0, 1 or 2 ring heteroatoms;
  d) a pyrrole ring fused to a 5- or 6-membered ring containing 0, 1, 2 or 3 ring heteroatoms;
  e) a pyrazole ring fused to a 5- or 6-membered ring containing 0, 1 or 2 ring heteroatoms;
  f) an imidazole ring fused to a 5- or 6-membered ring containing 0, 1 or 2 ring heteroatoms;
  g) an oxazole ring fused to a 5- or 6-membered ring containing 0, 1 or 2 ring heteroatoms;
  h) an isoxazole ring fused to a 5- or 6-membered ring containing 0, 1 or 2 ring heteroatoms;
  i) a thiazole ring fused to a 5- or 6-membered ring containing 0, 1 or 2 ring heteroatoms;
  j) an isothiazole ring fused to a 5- or 6-membered ring containing 0, 1 or 2 ring heteroatoms;
  k) a thiophene ring fused to a 5- or 6-membered ring containing 0, 1, 2 or 3 ring heteroatoms;
  l) a furan ring fused to a 5- or 6-membered ring containing 0, 1, 2 or 3 ring heteroatoms;
  m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocylic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof.

Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

The term "carbocyclyl" as used herein shall, unless the context indicates otherwise, include both aromatic and non-aromatic ring systems. Thus, for example, the term "carbocyclyl group" includes within its scope aromatic, non-aromatic, unsaturated, partially saturated and fully saturated carbocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to carbocyclyl groups, the carbocyclyl ring can, unless the context indicates otherwise, be optionally substituted (i.e. unsubstituted or substituted) by one or more substituents as discussed herein.

The term carbocyclyl comprises aryl, $C_{3-8}$cycloalkyl, $C_{3-8}$cycloalkenyl.

The term aryl as used herein refers to carbocyclyl aromatic groups including phenyl, naphthyl, indenyl, and tetrahydronaphthyl groups.

Whenever used hereinbefore or hereinafter that substituents can be selected each independently out of a list of numerous definitions, all possible combinations are intended which are chemically possible. Whenever used hereinbefore or hereinafter that a particular substituent is further substituted with two or more groups, such as for example hydroxyhalo$C_{1-4}$alkyl, hydroxyhalo$C_{1-4}$alkoxy, all possible combinations are intended which are chemically possible.

In one embodiment, the invention relates to a compound of formula (I-A).

In one embodiment, the invention relates to a compound of formula (I-B).

In one embodiment, the invention relates to a compound of formula (I-A) wherein $X_1$ is N, $X_2$ is N and $X_3$ is CH.

In one embodiment, the invention relates to a compound of formula (I-A), wherein $X_1$ is $CR^{3d}$, $X_2$ is N and $X_3$ is CH.

In one embodiment, the invention relates to a compound of formula (I-A), wherein $X_1$ is $CR^{3d}$, $X_2$ is $CR^{3d}$ and $X_3$ is N.

In one embodiment, the invention relates to a compound of formula (I-B), wherein $X_1$ is $CR^{3d}$.

In one embodiment, the invention relates to a compound of formula (I-B), wherein $X_1$ is N.

In one embodiment, D represents a 5 to 12 ring membered monocyclic or bicyclic carbocyclyl or a 5 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, D represents an aromatic 3 to 12, in particular an aromatic 5 to 12, ring membered monocyclic or bicyclic carbocyclyl or an aromatic 3 to 12, in particular an aromatic 5 to 12, ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, D represents an aromatic 3 to 12 (e.g. 5 to 10) ring membered monocyclic or bicyclic carbocyclyl, wherein said carbocyclyl may be optionally substituted by one or more (e.g. 1, 2 or 3) $R^1$ groups.

In one embodiment, D represents phenyl or naphthyl, wherein said phenyl or naphthyl may each be optionally substituted by one or more (e.g. 1, 2 or 3) $R^1$ groups.

In one embodiment, D represents a 5 to 12 ring membered monocyclic or bicyclic heterocyclyl containing at least one heteroatom selected from N, O or S, wherein said heterocyclyl may each be optionally substituted by one or more (e.g. 1, 2 or 3) $R^1$ groups.

In one embodiment, D represents an aromatic 5 to 12 ring membered monocyclic heterocyclyl containing at least one heteroatom selected from N, O or S, wherein said heterocyclyl group may each be optionally substituted by one or more (e.g. 1, 2 or 3) $R^1$ groups.

In one embodiment, D represents a 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, D represents an aromatic 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, D represents a 5 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, D represents a 5 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, D represents pyrazolyl (e.g. pyrazol-4yl), wherein said pyrazolyl may each be optionally substituted by one or more (e.g. 1, 2 or 3) $R^1$ groups.

In one embodiment, D represents a 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, D represents a 6 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, D represents a 6 ring membered monocyclic fully saturated heterocyclyl containing at least one heteroatom selected from N, O or S, wherein said heterocyclyl may each be optionally substituted by one or more (e.g. 1, 2 or 3) $R^1$ groups.

In one embodiment, D represents a 12 ring membered bicyclic heterocyclyl containing at least one heteroatom selected from N, O or S, wherein said heterocyclyl may each be optionally substituted by one or more (e.g. 1, 2 or 3) $R^1$ groups.

In one embodiment, D represents a 12 ring membered bicyclic aromatic heterocyclyl containing at least one heteroatom selected from N, O or S, wherein said heterocyclyl may each be optionally substituted by one or more (e.g. 1, 2 or 3) $R^1$ groups.

In one embodiment D represents

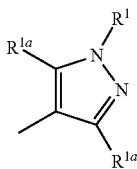

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo-$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy-$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$; and each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —NH($C_{3-8}$cycloalkyl), cyano$C_{1-4}$alkyl, $C_{1-4}$alkoxy$C_{1-4}$alkyl, and $C_{1-4}$alkyl substituted with one or more fluoro atoms. In one embodiment, $R^{1a}$ is independently selected from hydrogen and $C_{1-4}$alkyl. In one embodiment, $R^{1a}$ is hydrogen.

In one embodiment, D represents

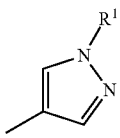

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy-$C_{1-6}$alkyl substituted with $R^6$, $C_{1-6}$alkyl substituted with Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$.

In one embodiment, D is other than pyrazolyl, in particular D is pyridinyl, phenyl, pyrolyl, pyrimidinyl, said rings being optionally substituted. Said optional substituents may represent halo, cyano, $C_{1-6}$alkyl, $C_{1-6}$alkoxy, —C(=O)—O—$C_{1-6}$alkyl, hydroxy$C_{1-6}$alkyl, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $R^6$, $C_{1-6}$alkyl substituted with $R^6$.

In one embodiment, D is optionally substituted 4-pyrazolyl. In one embodiment, D is 4-pyrazolyl substituted at the 1 position with $C_{1-6}$alkyl for example methyl.

In one embodiment, D is 1-pyrazolyl or 2-pyrazolyl, both may optionally be substituted.

In one embodiment, D is optionally substituted pyrazolyl.

In one embodiment, D is morpholinyl.

In one embodiment $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, $C_{1-6}$alkyl substituted with —C(=O)—$R^6$, hydroxy-$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$.

In one embodiment $R^1$ represents hydrogen, $C_{1-6}$alkyl, $C_{2-4}$alkenyl, hydroxy$C_{1-6}$alkyl, halo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —C(=O)—$NR^4R^5$, —S(=O)$_2$—$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —NH—S(=O)$_2$—$C_{1-6}$alkyl, $R^6$, $C_{1-6}$alkyl substituted with $R^6$, $C_{1-6}$alkyl substituted with —C(=O)—$R^6$, hydroxy$C_{1-6}$alkyl substituted with $R^6$, or $C_{1-6}$alkyl substituted with —Si(CH$_3$)$_3$.

In one embodiment $R^1$ represents hydrogen.

In one embodiment $R^1$ represents $C_{1-6}$alkyl. In one embodiment $R^1$ represents methyl.

In one embodiment each $R^2$ is independently selected from hydroxyl, halogen, cyano, $C_{1-4}$ alkyl, $C_{2-4}$alkenyl, $C_{1-4}$alkoxy, hydroxy$C_{1-4}$alkyl, hydroxy$C_{1-4}$alkoxy, halo$C_{1-4}$alkyl, halo$C_{1-4}$ alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ and —C(=O)—$NR^7R^8$; or when two $R^2$ groups are attached to adjacent carbon atoms they may be taken together to form a radical of formula —O—(C($R^{17}$)$_2$)$_p$—O— wherein $R^{17}$ represents hydrogen or fluorine and p represents 1 or 2.

In one embodiment each $R^2$ is independently selected from hydroxyl, halogen, cyano, $C_{1-4}$ alkyl, $C_{2-4}$alkenyl, $C_{1-4}$alkoxy, hydroxy$C_{1-4}$alkyl, hydroxy$C_{1-4}$alkoxy, halo$C_{1-4}$alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ or —C(=O)—$NR^7R^8$.

In one embodiment one or more $R^2$ represents $C_{1-4}$alkoxy, for example $CH_3O$—, or halogen, for example fluoro.

In one embodiment one or more $R^2$ represents $C_{1-4}$alkoxy, for example $CH_3O$—.

In one embodiment n is equal to 0. In one embodiment n is equal to 1. In one embodiment n is equal to 2. In one embodiment n is equal to 3. In one embodiment n is equal to 4.

In one embodiment, n is equal to 2, 3 or 4.

In one embodiment n is equal to 2 and one $R^2$ is present at the 3-position and the other is present at the 5-position.

In one embodiment n is equal to 2 and one $R^2$ is present at the 3-position and the other is present at the 5-position and each $R^2$ represents $C_{1-4}$alkoxy, for example each $R^2$ represents $CH_3O$—.

In one embodiment n is equal to 3 and one $R^2$ is present at the 2-position, one $R^2$ is present at the 3-position and one $R^2$ is present at the 5-position.

In one embodiment n is equal to 3 and one $R^2$ is present at the 3-position and represents $C_{1-4}$alkoxy, for example $CH_3O$—; one $R^2$ is present at the 5-position and represents $C_{1-4}$alkoxy, for example $CH_3O$—; one $R^2$ is present at the 2-position and represents halogen, for example fluoro.

In one embodiment n is equal to 4 and one $R^2$ is present at the 2-position, one $R^2$ is present at the 3-position, one $R^2$ is present at the 5-position and one $R^2$ is present at the 6-position.

In one embodiment n is equal to 4 and one $R^2$ is present at the 3-position and represents $C_{1-4}$alkoxy, for example $CH_3O$—; one $R^2$ is present at the 5-position and represents $C_{1-4}$ alkoxy, for example $CH_3O$—; one $R^2$ is present at the 2-position and represents halogen, for example fluoro, and one $R^2$ is present at the 6-position and represents halogen, for example fluoro.

In one embodiment, $R^{3a}$ represents $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy-$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with
—C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with
—O—C(=O)—$C_{1-6}$alkyl, $C_{2-6}$alkenyl substituted with $C_{1-6}$alkoxy, $C_{2-6}$alkynyl substituted with $C_{1-6}$ alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$.

In one embodiment, $R^{3a}$ is $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy-$C_{2-6}$alkenyl, hydroxy$C_{2-6}$alkynyl, hydroxyhalo$C_{1-6}$alkyl, cyano$C_{1-6}$ alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with
—O—C(=O)—$C_{1-6}$alkyl, $C_{2-6}$alkenyl substituted with $C_{1-6}$alkoxy, $C_{2-6}$alkynyl substituted with $C_{1-6}$ alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$, and the compound is a compound of formula (I-B).

In one embodiment, $R^{3a}$ is —$NR^{10}R^{11}$, hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo-$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl hydroxy$C_{2-6}$alkenyl, hydroxy-$C_{2-6}$alkynyl, hydroxyhalo$C_{1-6}$alkyl, cyano$C_{1-6}$ alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—,
$C_{1-6}$alkyl substituted with —O—C(=O)—$C_{1-6}$alkyl, $C_{1-6}$alkoxy$C_{1-6}$alkyl wherein each $C_{1-6}$alkyl may optionally be substituted with one or two hydroxyl groups or with
—O—C(=O)—$C_{1-6}$alkyl, $C_{2-6}$alkenyl substituted with $C_{1-6}$alkoxy, $C_{2-6}$alkynyl substituted with $C_{1-6}$ alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NR$^{12}$—S($=$O)$_2$—C$_{1-6}$alkyl, C$_{1-6}$alkyl substituted with —NH—S($=$O)$_2$-haloC$_{1-6}$alkyl, C$_{1-6}$alkyl substituted with —NR$^{12}$—S($=$O)$_2$—NR$^{14}$R$^{15}$, R$^{13}$, C$_{1-6}$alkyl substituted with —P($=$O)(OH)$_2$ or C$_{1-6}$alkyl substituted with —P($=$O)(OC$_{1-6}$alkyl)$_2$; for a compound of formula (I-A); and R$^{3a}$ is C$_{1-6}$alkyl, C$_{2-6}$alkenyl, C$_{2-6}$alkynyl,
haloC$_{1-6}$alkyl optionally substituted with —O—C($=$O)—C$_{1-6}$alkyl, hydroxyC$_{1-6}$alkyl optionally substituted with —O—C($=$O)—C$_{1-6}$alkyl, hydroxyC$_{2-6}$alkenyl, hydroxyC$_{2-6}$alkynyl, hydroxyhaloC$_{1-6}$ alkyl, cyano-C$_{1-6}$alkyl, C$_{1-6}$alkyl substituted with carboxyl, C$_{1-6}$alkyl substituted with —C($=$O)—C$_{1-6}$alkyl, C$_{1-6}$alkyl substituted with —C($=$O)—O—C$_{1-6}$alkyl, C$_{1-6}$alkyl substituted with C$_{1-6}$ alkoxyC$_{1-6}$alkyl-O—C($=$O)—, C$_{1-6}$alkyl substituted with C$_{1-6}$alkoxyC$_{1-6}$alkyl-C($=$O)—, C$_{1-6}$alkyl substituted with —O—C($=$O)—C$_{1-6}$alkyl, C$_{1-6}$alkoxyC$_{1-6}$alkyl wherein each C$_{1-6}$alkyl may optionally be substituted with one or two hydroxyl groups or with —O—C($=$O)—C$_{1-6}$alkyl, C$_{2-6}$alkenyl substituted with C$_{1-6}$alkoxy, C$_{2-6}$alkynyl substituted with C$_{1-6}$alkoxy, C$_{1-6}$alkyl substituted with R$^9$ and optionally substituted with —O—C($=$O)—C$_{1-6}$alkyl, C$_{1-6}$alkyl substituted with —C($=$O)—R$^9$, C$_{1-6}$alkyl substituted with hydroxyl and R$^9$, C$_{2-6}$alkenyl substituted with R$^9$, C$_{2-6}$alkynyl substituted with R$^9$, C$_{1-6}$alkyl substituted with —NR$^{10}$R$^{11}$, C$_{2-6}$alkenyl substituted with —NR$^{10}$R$^{11}$, C$_{2-6}$alkynyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, —C$_{1-6}$alkyl-C(R$^{12}$)$=$N—O—R$^{12}$, C$_{1-6}$alkyl substituted with —C($=$O)—NR$^{10}$R$^{11}$, C$_{1-6}$alkyl substituted with —O—C($=$O)—NR$^{10}$R$^{11}$, —S($=$O)$_2$—C$_{1-6}$alkyl, —S($=$O)$_2$-haloC$_{1-6}$alkyl, —S($=$O)$_2$—NR$^{14}$R$^{15}$, C$_{1-6}$alkyl substituted with —S($=$O)$_2$—C$_{1-6}$alkyl, C$_{1-6}$alkyl substituted with —S($=$O)$_2$-haloC$_{1-6}$alkyl, C$_{1-6}$alkyl substituted with —S($=$O)$_2$—NR$^{14}$R$^{15}$, C$_{1-6}$alkyl substituted with —NR$^{12}$—S($=$O)$_2$—C$_{1-6}$alkyl, C$_{1-6}$alkyl substituted with —NH—S($=$O)$_2$-haloC$_{1-6}$alkyl, C$_{1-6}$alkyl substituted with —NR$^{12}$—S($=$O)$_2$—NR$^{14}$R$^{15}$, R$^{13}$, C$_{1-6}$alkyl substituted with —P($=$O)(OH)$_2$ or C$_{1-6}$alkyl substituted with —P($=$O)(OC$_{1-6}$alkyl)$_2$, for a compound of formula (I-B).

In one embodiment, R$^{3a}$ is —NR$^{10}$R$^{11}$, hydroxyl, C$_{1-6}$alkyl, hydroxyC$_{1-6}$alkyl, hydroxyC$_{1-6}$alkyloxy, hydroxyhaloC$_{1-6}$alkyl, haloC$_{1-6}$alkyl, C$_{1-6}$alkyl substituted with —C($=$O)—C$_{1-6}$alkyl, C$_{1-6}$alkoxyC$_{1-6}$alkyl wherein each C$_{1-6}$alkyl may optionally be substituted with one or two hydroxyl groups, C$_{1-6}$alkyl substituted with R$^9$, C$_{1-6}$alkyl substituted with —NR$^{10}$R$^{11}$, C$_{1-6}$alkyl substituted with hydroxyl and —NR$^{10}$R$^{11}$, C$_{1-6}$alkyl substituted with one or two halogens and —NR$^{10}$R$^{11}$, C$_{1-6}$alkyl substituted with —C($=$O)—O—C$_{1-6}$alkyl, C$_{1-6}$alkyl substituted with —O—C($=$O)—NR$^{10}$R$^{11}$, C$_{1-6}$alkyl substituted with carboxyl, C$_{1-6}$alkyl substituted with —O—C($=$O)—NR$^{10}$R$^{11}$, C$_{1-6}$alkyl substituted with —NR$^{12}$—S($=$O)$_2$—C$_{1-6}$alkyl, C$_{1-6}$alkyl substituted with —NR$^{12}$—S($=$O)$_2$—NR$^{14}$R$^{15}$, C$_{1-6}$alkyl substituted with hydroxyl and R$^9$, —C$_{1-6}$alkyl-C(R$^{12}$)$=$N—O—R$^{12}$, C$_{1-6}$alkyl substituted with —C($=$O)—NR$^{10}$R$^{11}$, C$_{1-6}$alkyl substituted with —C($=$O)—R$^9$, hydroxyC$_{1-6}$alkoxy, C$_{2-6}$alkenyl, R$^{13}$ or C$_{1-6}$alkyl substituted with C$_{1-6}$alkoxyC$_{1-6}$alkyl-C($=$O)—.

In one embodiment R$^{3a}$ is —NR$^{10}$R$^{11}$, C$_{1-6}$alkyl, hydroxyl, hydroxyC$_{1-6}$alkyl, hydroxyC$_{1-6}$alkyloxy, cyanoC$_{1-6}$alkyl, C$_{1-6}$alkyl substituted with —C($=$O)—C$_{1-6}$alkyl, C$_{1-6}$alkyl substituted with —C($=$O)—O—C$_{1-6}$alkyl, C$_{1-6}$alkyl substituted with R$^9$, C$_{1-6}$alkyl substituted with —NR$^{10}$R$^{11}$, C$_{1-6}$alkyl substituted with hydroxyl and —NR$^{10}$R$^{11}$, or C$_{1-6}$alkyl substituted with —C($=$O)—NR$^{10}$R$^{11}$.

In one embodiment R$^{3a}$ is hydroxyl; C$_{1-6}$alkyl; hydroxyC$_{1-6}$alkyl; hydroxyC$_{1-6}$alkoxy; C$_{1-6}$alkyl substituted with —C($=$O)—O—C$_{1-6}$alkyl; C$_{1-6}$alkyl substituted with R$^9$, in particular C$_{1-6}$alkyl substituted with optionally substituted imidazolyl, in particular with optionally substituted imidazol-2-yl. In particular for a compound of formula (I-A).

In one embodiment R$^{3a}$ is hydroxyC$_{1-6}$alkyl. In particular for a compound of formula (I-B).

In one embodiment, R$^{3a}$ is hydroxyethyl.

In one embodiment R$^{3a}$ represents hydroxyl.

In one embodiment R$^{3b}$ represents hydrogen.

In one embodiment R$^{3b}$ represents hydroxyl.

In one embodiment R$^{3a}$ represents hydroxyl and R$^{3b}$ represents hydrogen.

In one embodiment R$^{3a}$ and R$^{3b}$ are taken together to form $=$O, to form $=$NR$^{10}$, to form cyclopropyl together with the carbon atom to which they are attached, to form $=$CH—C$_{0-4}$alkyl substituted with R$^{3c}$, or to form

wherein ring A is a monocyclic 5 to 7 membered saturated heterocycle containing one heteroatom selected from N, O or S, said heteroatom not being positioned in alpha position of the double bond, wherein ring A is optionally being substituted with cyano, C$_{1-4}$alkyl, hydroxyC$_{1-4}$alkyl, H$_2$N—C$_{1-4}$alkyl, (C$_{1-4}$alkyl)NH—C$_{1-4}$alkyl, (C$_{1-4}$ alkyl)$_2$N—C$_{1-4}$alkyl, (haloC$_{1-4}$alkyl)NH—C$_{1-4}$alkyl, C$_{1-4}$alkoxy-C$_{1-4}$alkyl, —C($=$O)—NH$_2$, —C($=$O)—NH(C$_{1-4}$alkyl), —C($=$O)—N(C$_{1-4}$alkyl)$_2$.

In one embodiment R$^{3a}$ and R$^{3b}$ are taken together to form $=$O, to form cyclopropyl together with the carbon atom to which they are attached, to form $=$CH—C$_{0-4}$alkyl substituted with R$^{3c}$, or to form

wherein ring A is a monocyclic 5 to 7 membered saturated heterocycle containing one heteroatom selected from N, O or S, said heteroatom not being positioned in alpha position of the double bond.

In one embodiment R$^{3a}$ and R$^{3b}$ are taken together to form $=$O.

In one embodiment R$^{3a}$ and R$^{3b}$ are taken together to form cyclopropyl together with the carbon atom to which they are attached.

In one embodiment R$^{3a}$ and R$^{3b}$ are taken together to form $=$CH—C$_{0-4}$alkyl substituted with R$^{3c}$.

In one embodiment R$^{3a}$ and R$^{3b}$ are taken together to form $=$CH—C$_{0-4}$alkyl substituted with R$^{3c}$ wherein R$^{3c}$ represents cyano.

In one embodiment R$^{3c}$ represents hydrogen.

In one embodiment R$^{3c}$ represents hydroxyl, C$_{1-6}$alkoxy, R$^9$, —NR$^{10}$R$^{11}$, —C($=$O)—NR$^{14}$R$^{15}$, cyano, —C($=$O)—C$_{1-6}$alkyl or —CH(OH)—C$_{1-6}$alkyl.

In one embodiment R$^{3c}$ represents hydroxyl, —C($=$O)—NR$^{14}$R$^{15}$, —NR$^{10}$R$^{11}$, cyano, or —C($=$O)—C$_{1-6}$alkyl.

In one embodiment R$^{3a}$ and R$^{3b}$ are taken together to form $=$CH—C$_{0-4}$alkyl substituted with R$^{3c}$ wherein R$^{3c}$ represents hydroxyl or —C($=$O)—NR$^{14}$R$^{15}$.

In one embodiment $R^{3a}$ and $R^{3b}$ are taken together to form =CH—$C_{1-4}$alkyl in the Z configuration.

In one embodiment $R^{3a}$ and $R^{3b}$ are taken together to form =CH—$C_{1-4}$alkyl in the E configuration.

In one embodiment, the invention relates to a compound of formula (I-B) wherein $R^{3b}$ represents hydroxyl and $R^{3a}$ represents hydroxy$C_{1-6}$alkyl.

In one embodiment, $R^{3d}$ represents hydrogen.

In one embodiment, $R^9$ is selected from:
an optionally substituted $C_{3-8}$cycloalkyl,
an optionally substituted aromatic 5 membered monocyclic heterocyclyl,
an optionally substituted saturated 6 membered monocyclic heterocyclyl.
a saturated or an aromatic 3, 4, 5 or 6 membered monocyclic heterocyclyl containing one or two oxygen heteroatoms,
an optionally substituted 4 membered heterocyclyl containing one oxygen heteroatom,
an optionally substituted aromatic 6 membered monocyclic heterocycle containing one or two nitrogen heteroatoms,
a partially saturated 6 membered monocyclic heterocyclyl containing one nitrogen heteroatom which may optionally be substituted,
an optionally substituted saturated 4 membered monocyclic heterocyclyl containing one nitrogen heteroatom,
a saturated 5 membered monocyclic heterocyclyl containing one nitrogen heteroatom,
a saturated 6 membered monocyclic heterocyclyl containing one nitrogen heteroatom,
a bicyclic heterocyclyl containing a benzene ring fused to a 5- or 6-membered ring containing 1, 2 or 3 ring heteroatoms,
a 4, 5 or 6 membered monocyclic saturated heterocycle substituted with two substituents which are attached to the same atom and which are taken together to form a 4 to 7-membered saturated monocyclic heterocyclyl containing at least one heteroatom selected from N, O or S,
an optionally substituted aromatic 5 membered monocyclic heterocyclyl containing one sulphur heteroatom,
an optionally substituted aromatic 5 membered monocyclic heterocyclyl containing one sulphur and one nitrogen heteroatom,
a saturated 6 membered monocyclic heterocyclyl containing two nitrogen heteroatoms,
an aromatic 5 membered monocyclic heterocyclyl containing four nitrogen heteroatoms,
an aromatic 5 membered monocyclic heterocyclyl containing one oxygen and two nitrogen heteroatoms,
an optionally substituted aromatic 5 membered monocyclic heterocyclyl containing two nitrogen heteroatoms,
an optionally substituted aromatic 5 membered monocyclic heterocyclyl containing three nitrogen heteroatoms,
a saturated 5 membered monocyclic heterocyclyl containing one nitrogen and one oxygen heteroatom,
a saturated 6 membered monocyclic heterocyclyl containing one nitrogen and one sulphur heteroatom,
a saturated 7 membered monocyclic heterocyclyl containing two nitrogen heteroatoms,
a saturated 7 membered monocyclic heterocyclyl containing one nitrogen and one oxygen heteroatom, and
phenyl or naphthyl, in particular phenyl.

In one embodiment, $R^9$ represents an optionally substituted 5 membered aromatic heterocycle, such as for example imidazolyl, or an optionally substituted 6 membered aromatic heterocycle, such as for example pyridyl, pyrimidinyl or pyrazinyl. Optional substituents may represent $C_{1-4}$alkoxy or —S(=O)$_2$—NR$^{14}$R$^{15}$.

In one embodiment, $R^9$ represents an optionally substituted 5 membered aromatic heterocycle, such as for example imidazolyl. Optional substituents may represent —S(=O)$_2$—NR$^{14}$R$^{15}$.

In one embodiment, $R^9$ represents an optionally substituted 6 membered aromatic heterocycle, such as for example pyridinyl or pyrimidinyl. Optional substituents may represent $C_{1-4}$alkoxy.

In one embodiment, $R^9$ represents an optionally substituted 5 membered aromatic or saturated heterocycle, such as for example imidazolyl, pyrolidinyl, oxazolidinyl. Optional substituents may represent =O, a 5 or 6-membered aromatic monocyclic heterocyclyl containing at least one heteroatom selected from N, O or S wherein said heterocyclyl is optionally substituted with $R^{16}$; or —S(=O)$_2$—NR$^{14}$R$^{15}$.

In one embodiment, $R^9$ represents $C_{3-6}$ cycloalkyl, such as for example cyclopropyl, a 3 membered saturated heterocyclyl, such as for example oxiranyl, an optionally substituted 5 membered saturated heterocycle, such as for example pyrolidinonyl, an optionally substituted 6 membered aromatic or saturated heterocycle, such as for example pyridyl, pyrimidinyl, pyrazinyl, piperazinyl, or morpholinyl, an optionally substituted bicyclic heterocycle, such as for example 1H-isoindol-1,3-dione. Optional substituents may represent =O, $C_{1-4}$alkoxy, $C_{1-4}$alkyl substituted with —NR$^{14}$R$^{15}$, hydroxy$C_{1-4}$alkyl, or $C_{1-4}$alkyl-C(=O)—.

In one embodiment $R^{10}$ represents hydrogen or $C_{1-6}$alkyl.

In one embodiment $R^{10}$ is hydrogen.

In one embodiment $R^{11}$ represents hydrogen, $C_{1-6}$alkyl, halo$C_{1-6}$alkyl, —C(=O)—$C_{1-6}$alkyl, —S(=O)$_2$—$C_{1-6}$alkyl, —S(=O)$_2$—NR$^{14}$R$^{15}$, hydroxy$C_{1-6}$alkyl, —C(=O)-hydroxyhalo$C_{1-6}$alkyl, —C(=O)—R$^6$, cyano-$C_{1-6}$alkyl, R$^6$, —C(=O)—R$^6$, $C_{1-6}$alkyl substituted with R$^6$, —C(=O)-halo$C_{1-6}$alkyl, $C_{1-6}$ alkyl substituted with —Si(CH$_3$)$_3$, $C_{1-6}$alkyl substituted with —NR$^{14}$R$^{15}$, $C_{1-6}$alkyl substituted with —C(=O)—NR$^{14}$R$^{15}$, $C_{1-6}$alkoxy, hydroxyhalo$C_{1-6}$alkyl, carboxyl, or $C_{1-6}$alkoxy$C_{1-6}$alkyl.

In one embodiment $R^{10}$ and $R^{11}$ represent hydrogen or $C_{1-6}$alkyl.

In one embodiment, $R^6$ represents a 6-membered monocyclic saturated heterocyclyl which is optionally substituted. For example piperazinyl or morpholinyl or tetrahydropyranyl, optionally substituted with halogen, $C_{1-6}$alkyl, or $C_{1-6}$alkyl-O—C(=O).

In one embodiment, $R^6$ represents a 6-membered monocyclic aromatic heterocyclyl which is optionally substituted. For example pyridinyl, optionally substituted with halogen, $C_{1-6}$alkyl, or $C_{1-6}$alkyl-O—C(=O)—.

In one embodiment, $R^{12}$ represents hydrogen or $C_{1-4}$alkyl optionally substituted with $C_{1-4}$alkyloxy.

In one embodiment, $R^{13}$ represents a saturated 4 to 6-membered monocyclic heterocyclyl containing at least one heteroatom selected from N or O.

In one embodiment, $R^{14}$ and $R^{15}$ each independently represent hydrogen or $C_{1-4}$alkyl.

In one embodiment of the invention, n represents an integer equal to 2; and each $R^2$ represents $C_{1-4}$alkoxy, for example CH$_3$O—; $R^{3a}$ represents hydroxyl, hydroxy$C_{1-6}$alkyl, hydroxy$C_{1-6}$alkoxy, $C_{1-6}$alkyl, $C_{1-6}$alkyl substituted with R$^9$, $C_{1-6}$alkyl substituted with —C(=O)—O—$C_{1-6}$alkyl; or $R^{3a}$ and $R^{3b}$ are taken together to form =O, or to form =CH—$C_{0-4}$alkyl substituted with $R^{3c}$; $R^{3c}$ represents hydroxyl or —C(=O)—NR$^{14}$R$^{15}$; $R^{3b}$ represents hydrogen or hydroxyl; $R^{3d}$ represents hydrogen; D represents pyrazolyl substituted with $C_{1-6}$alkyl; $R^9$ represents an optionally substituted 5 membered aromatic heterocycle, such as for example imidazolyl, $R^{14}$ and $R^{15}$ each independently represent hydrogen or $C_{1-4}$alkyl.

In one embodiment of the invention, n represents an integer equal to 1 or 2; and each $R^2$ represents hydroxyl or $C_{1-4}$alkoxy, for example $CH_3O—$; $R^{3a}$ represents hydroxyl, hydroxy$C_{1-6}$alkyl, hydroxy$C_{1-6}$alkoxy, $C_{1-6}$alkyl, $C_{1-6}$alkyl substituted with $R^9$, $C_{1-6}$alkyl substituted with —C(=O)—O—$C_{1-6}$alkyl; or $R^{3a}$ and $R^{3b}$ are taken together to form =O, or to form =CH—$C_{0-4}$alkyl substituted with $R^{3c}$; $R^{3c}$ represents hydroxyl, cyano or —C(=O)—$NR^{14}R^{15}$; $R^{3b}$ represents hydrogen or hydroxyl; $R^{3d}$ represents hydrogen; D represents morpholinyl or pyrazolyl substituted with $C_{1-6}$alkyl; $R^9$ represents an optionally substituted 5 membered aromatic heterocycle, such as for example imidazolyl, $R^{14}$ and $R^{15}$ each independently represent hydrogen or $C_{1-4}$alkyl.

In one embodiment of the invention, the compound is a compound of formula (I-A), wherein n represents an integer equal to 2; and each $R^2$ represents $C_{1-4}$alkoxy, for example $CH_3O—$; $R^{3a}$ represents hydroxyl; hydroxy$C_{1-6}$alkyl such as for example —$CH_2$—$CH_2$—OH; hydroxy$C_{1-6}$alkoxy such as for example —O—$CH_2$—$CH_2$—OH; $C_{1-6}$alkyl, for example $CH_3—$; $C_{1-6}$alkyl, for example —$CH_3$, substituted with $R^9$, for example imidazolyl or substituted imidazolyl; $C_{1-6}$alkyl substituted with —C(=O)—O—$C_{1-6}$alkyl, for example —$CH_2$—C(=O)—O—$CH_3$; or $R^{3a}$ and $R^{3b}$ are taken together to form =O, or to form =CH—$C_{0-4}$alkyl, for example =CH—$CH_2$—, substituted with $R^{3c}$; $R^{3c}$ represents hydroxyl or —C(=O)—$NR^{14}R^{15}$; $R^{3b}$ represents hydrogen or hydroxyl; $R^{3d}$ represents hydrogen; D represents pyrazolyl substituted with $C_{1-6}$alkyl such as for example —$CH_3$; $R^9$ represents an optionally substituted 5 membered aromatic heterocycle, such as for example imidazolyl optionally substituted with for example —S(=O)—$N(CH_3)_2$; $R^{14}$ and $R^{15}$ each independently represent hydrogen or $C_{1-4}$alkyl for example $CH_3—$. In particular, in the compound of formula (I-A), $X_1$ is N, $X_2$ is N and $X_3$ is CH, or $X_1$ is $CR^{3d}$, $X_2$ is N and $X_3$ is CH.

In one embodiment of the invention, the compound is a compound of formula (I-A), wherein n represents an integer equal to 1 or 2; and each $R^2$ represents hydroxyl or $C_{1-4}$alkoxy, for example $CH_3O—$; $R^{3a}$ represents hydroxyl; hydroxy$C_{1-6}$alkyl such as for example —$CH_2$—$CH_2$—OH; hydroxy$C_{1-6}$alkoxy such as for example —O—$CH_2$—$CH_2$—OH; $C_{1-6}$alkyl, for example $CH_3—$; $C_{1-6}$alkyl, for example —$CH_3$, substituted with $R^9$, for example imidazolyl or substituted imidazolyl; $C_{1-6}$alkyl substituted with —C(=O)—O—$C_{1-6}$alkyl, for example —$CH_2$—C(=O)—O—$CH_3$ or $CH_2$—C(=O)—O—$CH_2CH_3$; or $R^{3a}$ and $R^{3b}$ are taken together to form =O, or to form =CH—$C_{0-4}$alkyl, for example =CH— or =CH—$CH_2$—, substituted with $R^{3c}$; $R^{3c}$ represents hydroxyl, cyano or —C(=O)—$NR^{14}R^{15}$; $R^{3b}$ represents hydrogen or hydroxyl; $R^{3d}$ represents hydrogen; D represents morpholinyl or pyrazolyl substituted with $C_{1-6}$alkyl such as for example —$CH_3$; $R^9$ represents an optionally substituted 5 membered aromatic heterocycle, such as for example imidazolyl optionally substituted with for example —S(=O)—$N(CH_3)_2$; $R^{14}$ and $R^{15}$ each independently represent hydrogen or $C_{1-4}$alkyl for example $CH_3—$. In particular, in the compound of formula (I-A), $X_1$ is N, $X_2$ is N and $X_3$ is CH, or $X_1$ is $CR^{3d}$, $X_2$ is N and $X_3$ is CH, or $X_1$ is $CR^{3d}$, $X_2$ is CH and $X_3$ is N.

In one embodiment of the invention, the compound is a compound of formula (I-B), wherein n represents an integer equal to 2; and each $R^2$ represents $C_{1-4}$alkoxy, for example $CH_3O—$; $R^{3a}$ represents hydroxy$C_{1-6}$alkyl; $R^{3b}$ represents hydroxyl; $R^{3d}$ represents hydrogen; D represents pyrazolyl substituted with $C_{1-6}$alkyl. In particular, in the compound of formula (I-B), $X_1$ is N.

In one embodiment, D is a 5 membered monocyclic aromatic heterocyclyl, wherein said heterocyclyl may optionally be substituted by one or more (e.g. 1, 2 or 3) $R^1$ groups, and wherein one or more of the following applies:

n is 2;

$R^2$ is $C_{1-6}$alkyloxy;

$R^2$ is placed in position 3 and 5.

In one embodiment, D is pyridinyl, phenyl, pyrrolyl, pyrimidinyl, said rings being optionally substituted, more in particular D is pyridinyl, phenyl, pyrrolyl, said rings being optionally substituted and n is 2; even more in particular D is pyridinyl, phenyl, pyrrolyl, pyrimidinyl, said rings being optionally substituted; n is 2; $R^2$ is $C_{1-6}$alkyloxy; even further in particular D is pyridinyl, phenyl, pyrrolyl, said rings being optionally substituted; n is 2; $R^2$ is $C_{1-6}$alkyloxy and said $R^2$ is placed in position 3 and 5.

In one embodiment there is provided compounds of formula

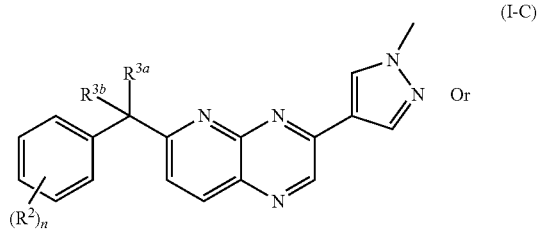

(I-C) Or

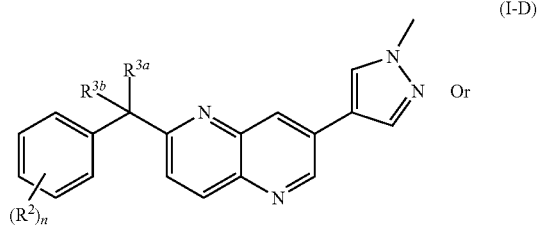

(I-D) Or

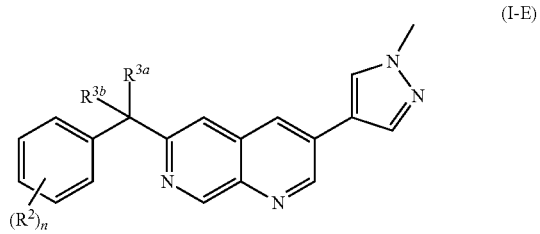

(I-E) Or

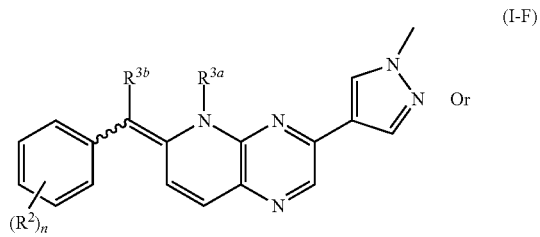

(I-F) Or

-continued

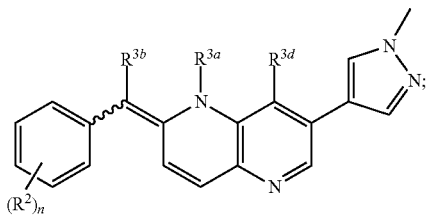

(I-G)

including any tautomeric or stereochemically isomeric form thereof;
wherein n, R², R³ᵃ, R³ᵇ and R³ᵈ are as defined herein;
the N-oxides thereof, the pharmaceutically acceptable salts thereof or the solvates thereof.

In one embodiment there is provided compounds of formula (I-C), (I-D), (I-E), (I-F), or (I-G) including any tautomeric or stereochemically isomeric form thereof, wherein:
R² represents $C_{1-4}$alkoxy (for example $CH_3O$—) or halogen (for example fluoro); in particular $C_{1-4}$alkoxy (for example $CH_3O$—); and
R³ᵃ represents hydroxy$C_{1-6}$alkyl (e.g. —$CH_2CH_2OH$), $C_{1-6}$alkyl (e.g. $C_{1-4}$alkyl) substituted with R⁹ (e.g. wherein R⁹ represents an optionally substituted aromatic 5 or 6 membered monocyclic heterocyclyl, for example optionally substituted imidazolyl, pyrimidinyl, or pyrazinyl), $C_{1-6}$alkyl (e.g. $C_{1-4}$alkyl) substituted with —$NR^{10}R^{11}$ wherein R¹⁰ and R¹¹ are independently selected from hydrogen, $C_{1-6}$alkyl and halo$C_{1-6}$alkyl (e.g. hydrogen, iso-propyl or —$CH_2CF_3$);
the N-oxides thereof, the pharmaceutically acceptable salts thereof or the solvates thereof.

In one embodiment there is provided compounds of formula (I-C) or Formula (I-D) including any tautomeric or stereochemically isomeric form thereof, wherein:
R² represents $C_{1-4}$alkoxy (for example $CH_3O$—) or halogen (for example fluoro); and
R³ᵃ represents hydroxy$C_{1-6}$alkyl (e.g. —$CH_2CH_2OH$ or —$CH_2CH_2CH_2OH$),
$C_{1-6}$alkoxy$C_{1-6}$alkyl wherein each $C_{1-6}$alkyl may optionally be substituted with one or two hydroxyl groups (e.g. —$CH_2CHOHCH_2OCH_3$), hydroxyhalo$C_{1-6}$alkyl (e.g. —$CH_2CHOHCF_3$), $C_{1-4}$alkyl (e.g. methyl) substituted with R⁹ (e.g. wherein R⁹ represents an optionally substituted aromatic 5 or 6 membered monocyclic heterocyclyl, for example unsubstituted imidazolyl (e.g. imidazol-2-yl), unsubstituted pyrimidinyl (e.g. pyrimidin-2-yl), unsubstituted pyrazinyl, or imidazolyl substituted with —$S(O)_2$—N$(CH_3)_2$), $C_{1-4}$alkyl (e.g. —$CH_2CH_2$—) substituted with —$NR^{10}R^{11}$ wherein one of R¹⁰ and R¹¹ represents hydrogen and the other represents $C_{1-6}$alkyl, for example —$CH_3$ or —$CH(CH_3)_2$ (e.g. R³ represents —$CH_2CH_2NHCH_3$ or —$CH_2CH_2NHCH(CH_3)_2$),
the N-oxides thereof, the pharmaceutically acceptable salts thereof or the solvates thereof.

In one embodiment there is provided compounds of formula (I-C) including any tautomeric or stereochemically isomeric form thereof, wherein:
R² represents $C_{1-4}$alkoxy (for example $CH_3O$—) or halogen (for example fluoro); and
R³ᵃ represents hydroxy$C_{1-6}$alkyl (e.g. —$CH_2CH_2OH$ or —$CH_2CH_2CH_2OH$),
$C_{1-6}$alkoxy$C_{1-6}$alkyl wherein each $C_{1-6}$alkyl may optionally be substituted with one or two hydroxyl groups (e.g. —$CH_2CHOHCH_2OCH_3$), hydroxyhalo$C_{1-6}$alkyl (e.g. —$CH_2CHOHCF_3$), $C_{1-6}$alkyl (e.g. $C_{1-4}$alkyl) substituted with R⁹ (e.g. wherein R⁹ represents an optionally substituted aromatic 5 or 6 membered monocyclic heterocyclyl, for example optionally substituted imidazolyl, pyrimidinyl, or pyrazinyl), $C_{1-6}$alkyl (e.g. $C_{1-4}$alkyl) substituted with —$NR^{10}R^{11}$ wherein R¹⁰ and R¹¹ are independently selected from hydrogen, $C_{1-6}$alkyl and halo$C_{1-6}$alkyl (e.g. hydrogen, iso-propyl or —$CH_2CF_3$),
the N-oxides thereof, the pharmaceutically acceptable salts thereof or the solvates thereof.

In one embodiment there is provided compounds of Formula (I-D) including any tautomeric or stereochemically isomeric form thereof, wherein:
R² represents $C_{1-4}$alkoxy (for example $CH_3O$—) or halogen (for example fluoro); and
R³ᵃ represents $C_{1-6}$alkyl (e.g. $C_{1-4}$alkyl) substituted with —$NR^{10}R^{11}$ wherein R¹⁰ and R¹¹ are independently selected from hydrogen, $C_{1-6}$alkyl and halo$C_{1-6}$alkyl (e.g. hydrogen, iso-propyl or —$CH_2CF_3$) (e.g. R³ᵃ represents $CH_2CH_2NHCH_3$ or —$CH_2CH_2NHCH(CH_3)_2$);
the N-oxides thereof, the pharmaceutically acceptable salts thereof or the solvates thereof.

In one embodiment the compound is a compound of formula (I-C):

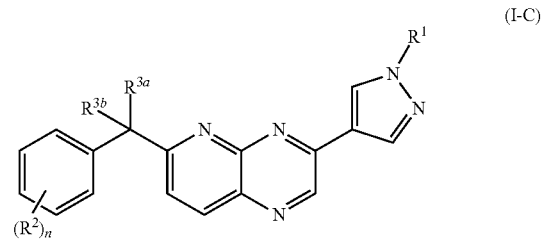

(I-C)

wherein n, R¹, R², R³ᵃ and R³ᵇ are as defined herein.

In one embodiment, the present invention relates to any one of the following compounds

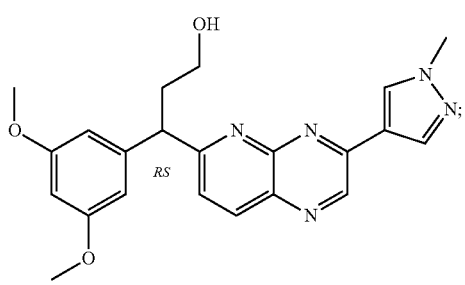

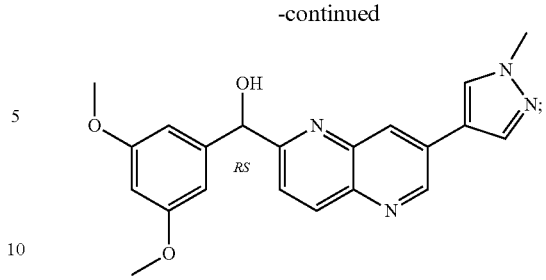

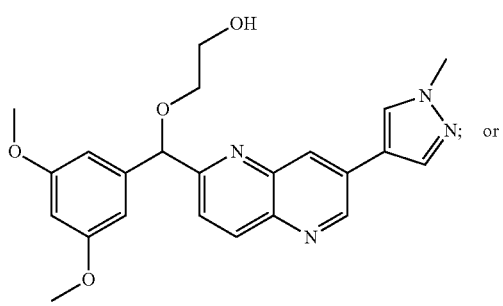

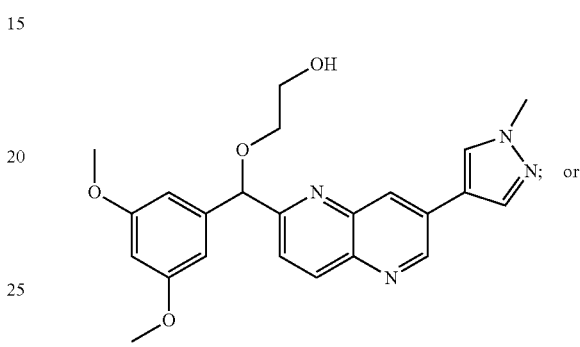

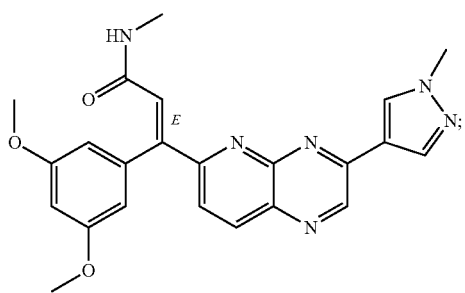

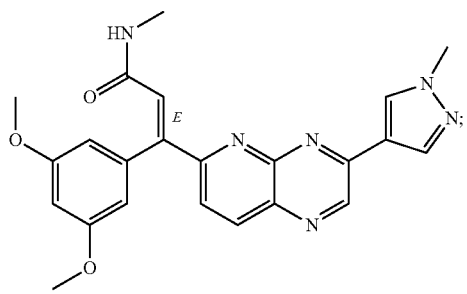

a N-oxide thereof, a pharmaceutically acceptable salt thereof or a solvate thereof.

In one embodiment, the present invention relates to any one of the following compounds

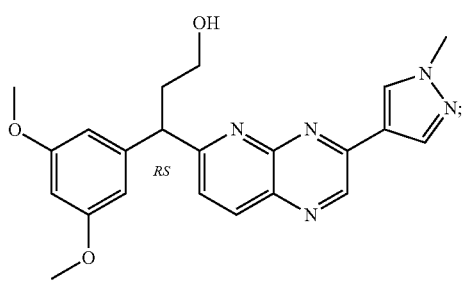

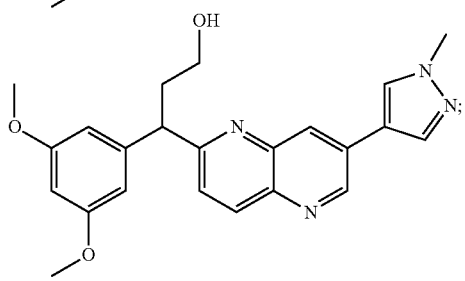

a N-oxide thereof, a pharmaceutically acceptable salt thereof or a solvate thereof.

For the avoidance of doubt, it is to be understood that each general and specific preference, embodiment and example for one substituent may be combined, whenever possible, with each general and specific preference, embodiment and example for one or more, preferably, all other substituents as defined herein and that all such embodiments are embraced by this application.

Whenever reference is made hereinbefore or hereinafter to a compound of formula (I), it means a compound of formula (I-A) or (I-B).

Methods for the Preparation of Compounds of Formula (I)

In this section, as in all other sections of this application unless the context indicates otherwise, references to formula (I) also include all other sub-groups and examples thereof as defined herein.

In general, compounds of formula (I-A) or (I-B) can be prepared according to the following reaction Scheme 1.

Scheme 1

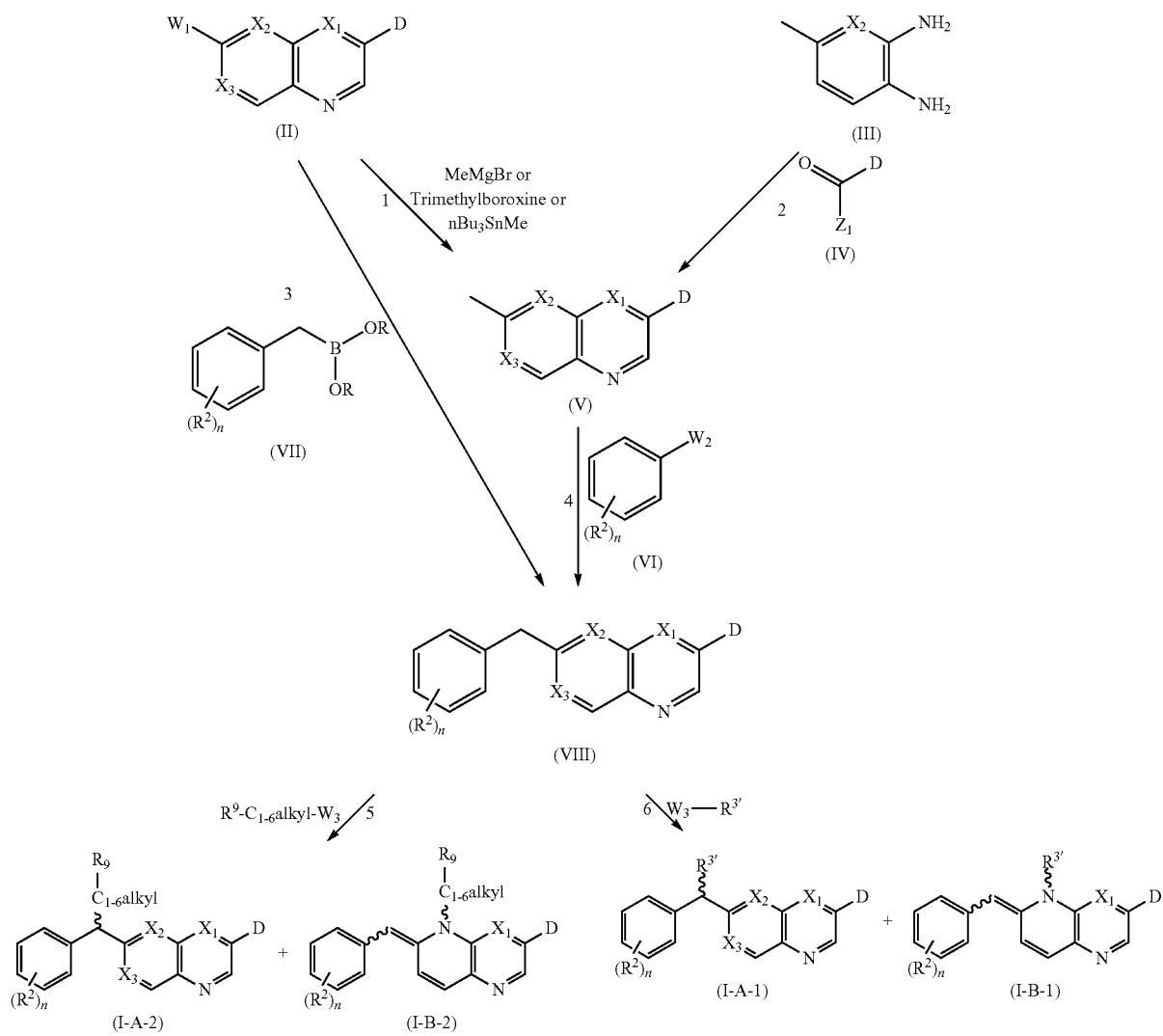

In Scheme 1, the following reaction conditions apply:
1: in the presence of a suitable methylating agent, such as for example MeMgBr, trimethylboroxine or nBu₃SnMe; a suitable catalyst, such as for example Pd(PPh₃)₄ or PdCl₂(dppf).CH₂Cl₂; a suitable solvent, such as for example N,N-dimethylformamide or dioxane and water; and optionally a suitable base, such as for example K₂CO₃; and wherein $W_1$ is a suitable leaving group, such as for example halogen, e.g. chloro;
2: in the presence of a suitable base, such as for example diisopropyl ethylamine; and a suitable solvent, such as for example acetonitrile and wherein $Z_1$ in the intermediate of formula (IV) is —CH₂—Br or —CH(=O);
3: in the presence of a suitable catalyst such as for example Pd(Ph₃)₄, a suitable base such as for example Na₂CO₃ and a suitable solvent such as for example dioxane and water
4: in the presence of Cs₂CO₃, a suitable catalyst, such as for example Pd(3,5,3'5'-OMe-dba)₂, a suitable ligand, such as for example 9,9-dimethyl-4,5-bis(diphenylphosphino)xanthenes, and a suitable solvent, such as for example dioxane, and wherein $W_2$ in the intermediate of formula (VI) is a suitable leaving group, such as for example halogen, e.g. bromo;
5: in the presence of a suitable base, such as for example butyl lithium, and a suitable solvent, such as for example tetrahydrofuran, and wherein $W_3$ represents a suitable leaving group, such as for example halo, e.g. chloro and the like;

6: in the presence of a suitable base, such as for example butyl lithium, and a suitable solvent, such as for example—THF, and wherein $W_3$ represents a suitable leaving group, such as for example halo, e.g. bromo and the like, and $R^{3'}$ represents optionally substituted $C_{1-6}$alkyl. This reaction can also be performed with a protected form of the reactant, namely $W_3$-$R^{3'}$-P wherein P is a suitable protective group, such as for example a tert-butyldimethylsilyl group, followed by a suitable deprotection reaction, such as in the presence of a suitable reagent, such as for example tetrabutylammonium fluoride or a suitable acid, e.g. HCl or trifluoroacetic acid, and a suitable solvent such as for example tetrahydrofuran.

Compounds of formula (I-A) can also be prepared according to the following reaction Scheme 2.

Scheme 2

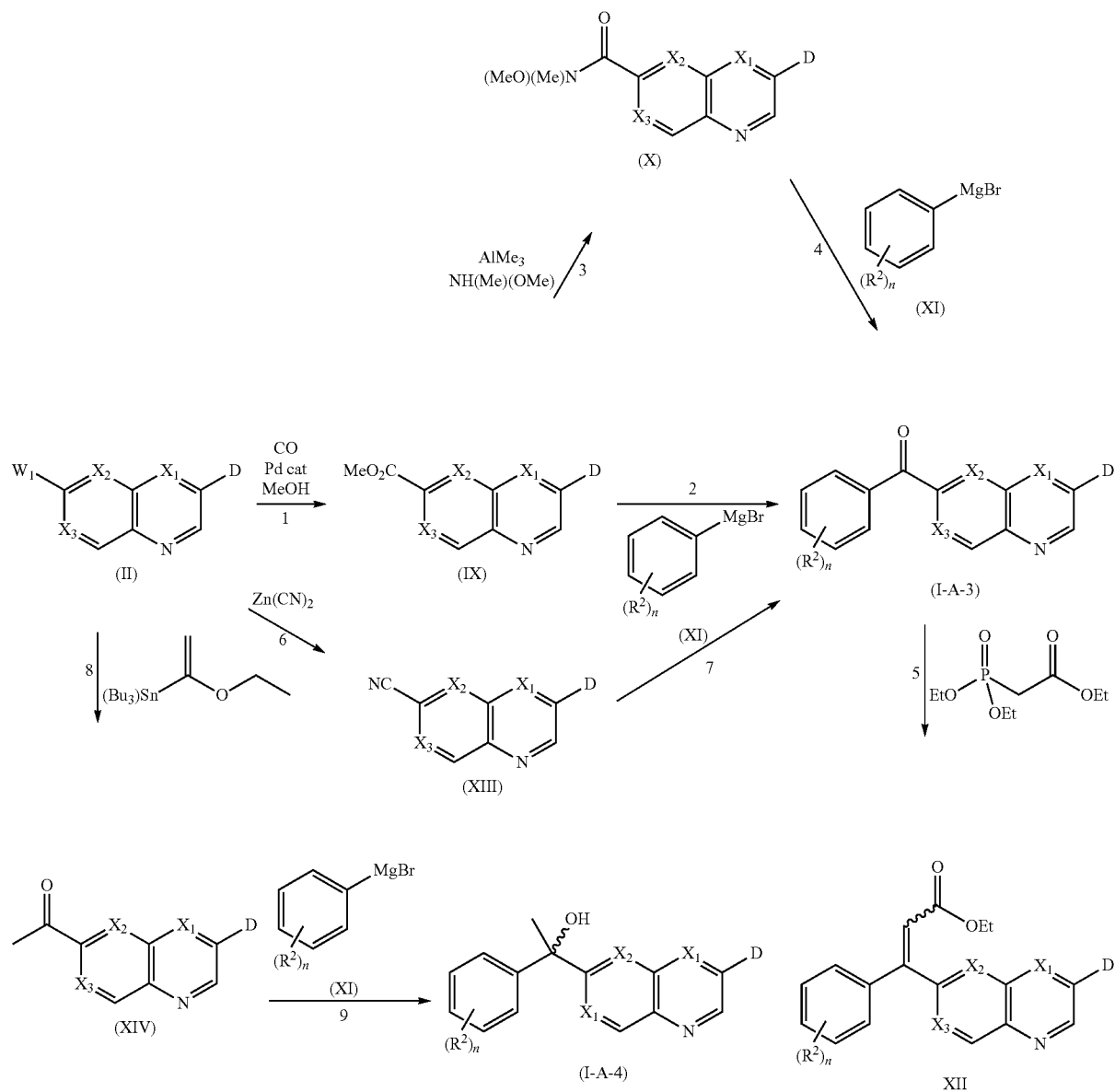

In Scheme 2, the following reaction conditions apply:
1: under CO atmosphere, in the presence of a suitable solvent, such as a suitable alcohol, e.g. methanol, and wherein the palladium catalyst is for example Pd(OAc)$_2$ or PdCl$_2$(dppf).CH$_2$Cl$_2$, and a suitable ligand, such as for example 1,3-bis(diphenylphosphino)propane, and optionally in the presence of a suitable base, such as for example potassium acetate or triethylamine;
2: in the presence of a suitable solvent, such as for example tetrahydrofuran;
3: in the presence of a suitable solvent, such as for example tetrahydrofuran;
4: in the presence of a suitable solvent, such as for example tetrahydrofuran;
5: in the presence of a suitable base, such as for example sodium hydride, and a suitable solvent, such as for example N,N-dimethylformamide or tetrahydrofuran;
6: in the presence of a suitable catalyst, such as for example Pd(PPh$_3$)$_4$, and a suitable solvent, such as for example N,N-dimethylformamide;

7: in the presence of a suitable solvent, such as for example toluene;

8: in the presence of a suitable catalyst, such as for example Pd(PPh$_3$)$_4$, and a suitable solvent, such as for example toluene, and further in the presence of a suitable acid, such as aqueous hydrochloric acid 9: in the presence of a suitable solvent, such as for example tetrahydrofuran.

Compounds of formula (I-A) can also be prepared according to the following reaction Scheme 3.

Scheme 3

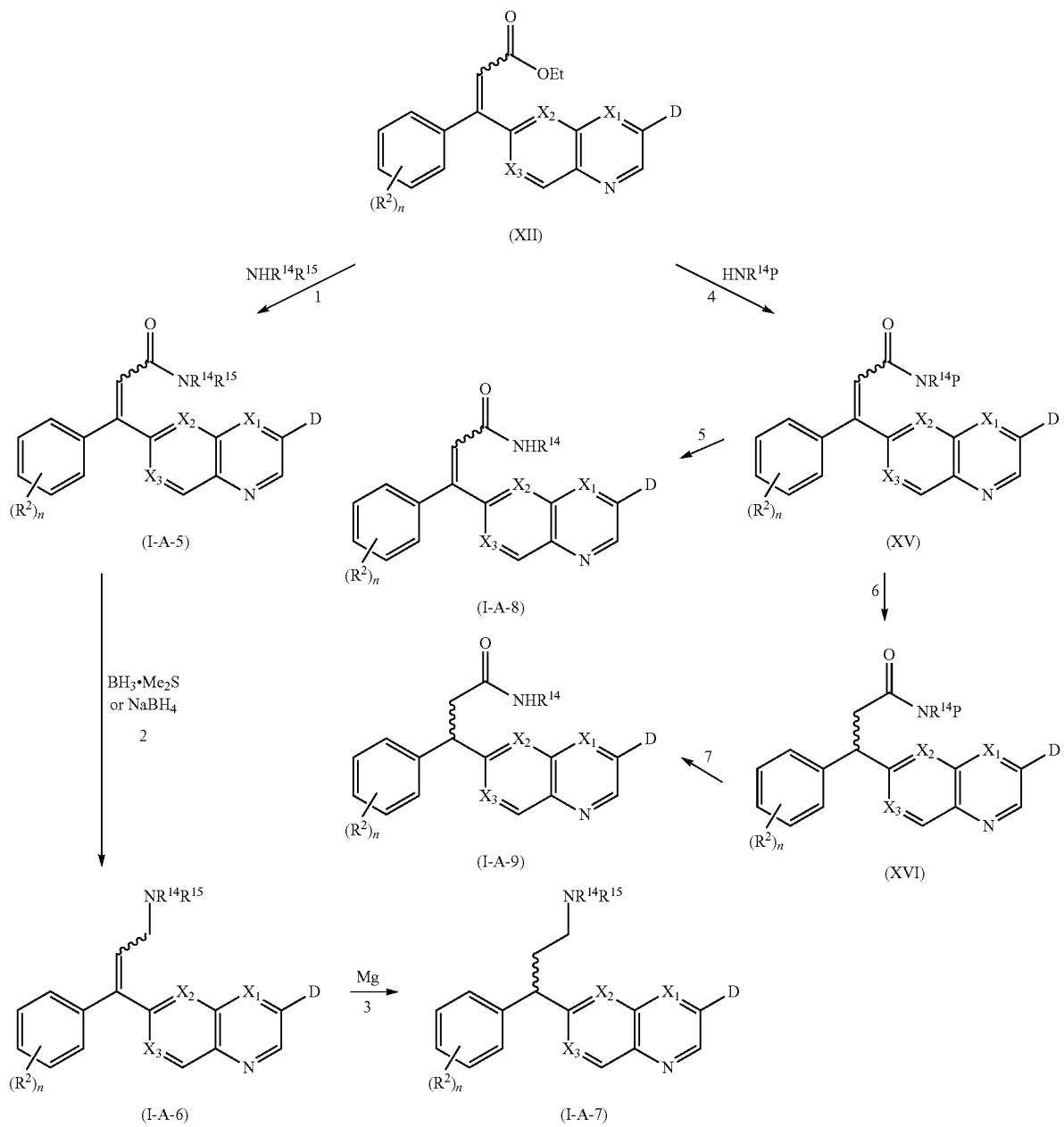

In Scheme 3, the following reaction conditions apply:

1: in the presence of a suitable lewis acid such as for example trimethylaluminium, and a suitable solvent, such as for example toluene;

2: in the presence of a suitable solvent such as for example tetrahydrofuran or dioxane 3: in the presence of a suitable solvent, such as for example tetrahydrofuran, and an alcohol, e.g. methanol and the like;

4: in the presence of a suitable lewis acid such as for example trimethylaluminium, and a suitable solvent, such as for example toluene; and wherein P represents a suitable protective group, such as for example —C(=O)—OC(CH$_3$)$_3$;

5: in the presence of a suitable acid, such as for example HCl or trifluoroacetic acid, and a suitable solvent, such as for example an alcohol, e.g. methanol, or dichloromethane;

6: in the presence of Mg and a suitable solvent, such as for example tetrahydrofuran or a suitable alcohol, e.g. methanol; or in the presence of H$_2$ and a suitable catalyst, such as for example palladium on charcoal, and a suitable solvent, such as for example tetrahydrofuran;

7: in the presence of a suitable acid, such as for example HCl or trifluoroacetic acid, and a suitable solvent, such as for example an alcohol, e.g. methanol, or dichloromethane.

Compounds of formula (I-A) can also be prepared according to the following reaction Scheme 4.

Scheme 4

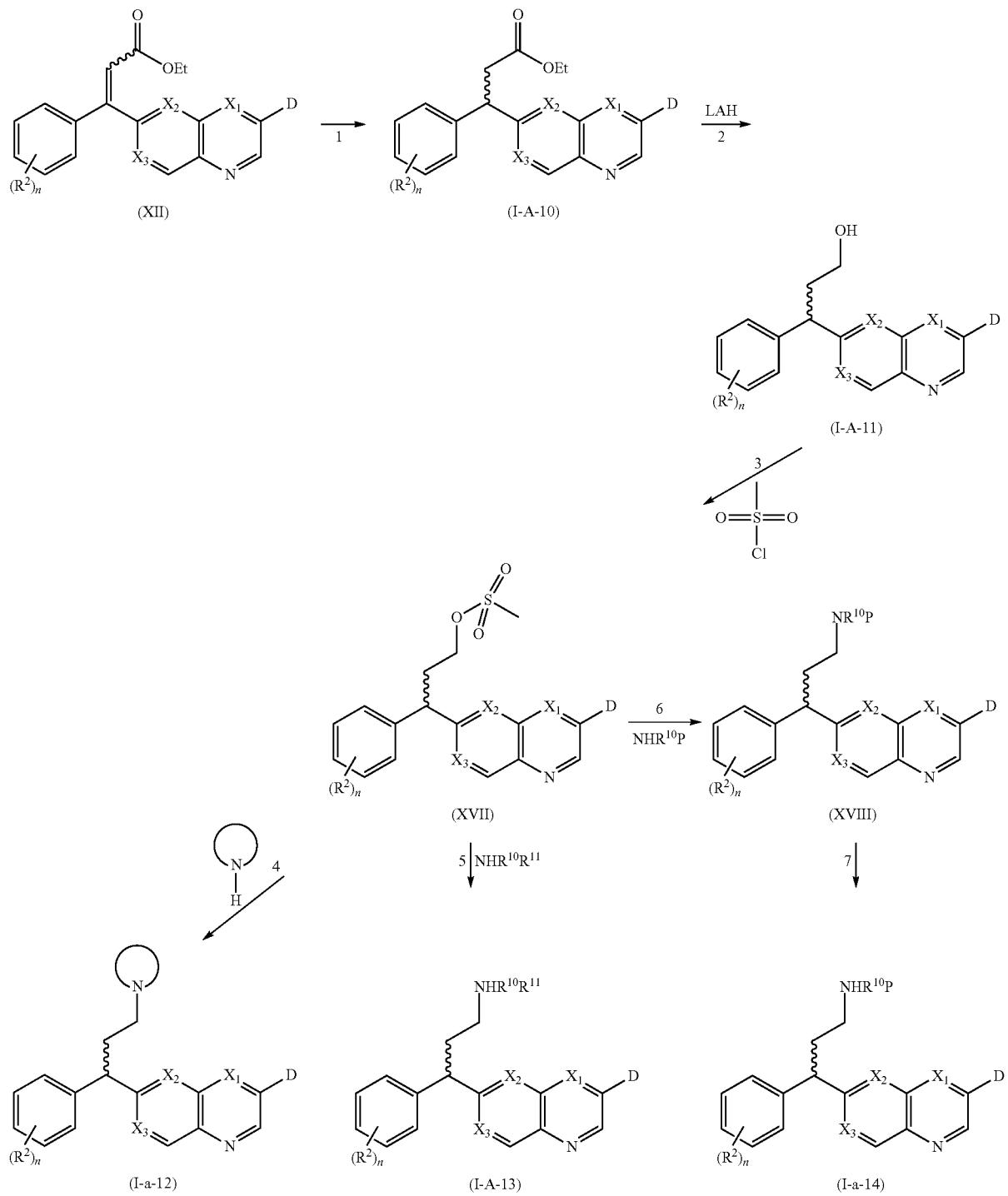

In Scheme 4, the following reaction conditions apply:

1: in the presence of Mg and a suitable solvent, such as for example tetrahydrofuran or a suitable alcohol, e.g. methanol; or in the presence of $H_2$ and a suitable catalyst, such as for example palladium on charcoal, and a suitable solvent, such as for example tetrahydrofuran;

2: in the presence of a suitable reducing agent, such as for example diisobutylaluminium hydride or lithium aluminium hydride, and a suitable solvent, such as for example tetrahydrofuran;

3: in the presence of a suitable base, such as for example triethylamine, diisopropylethanamine or N,N-dimethyl-4-aminopyridine, and a suitable solvent, such as for example dichloromethane or tetrahydrofuran;

4-5-6: optionally in the presence of a suitable base, such as for example triethylamine, potassium carbonate, sodium carbonate or sodium hydride, and optionally a suitable solvent, such as for example acetonitrile, tetrahydrofuran, N,N-dimethylformamide, and wherein P represents a suitable protective group, such as for example —C(=O)—OC(CH$_3$)$_3$. (In step 4

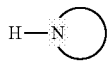

represents a suitable nitrogen containing ring (unsubstituted or substituted) within the definition of R$^9$. The reaction of step 4 can also be performed with a suitable salt of

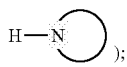;

7: in the presence of a suitable acid, such as for example HCl or trifluoroacetic acid, and a suitable solvent, such as for example an alcohol, e.g. methanol, or dichloromethane.

Compounds of formula (I-A) or (I-B) can also be prepared according to the following reaction Scheme 5.

Scheme 5

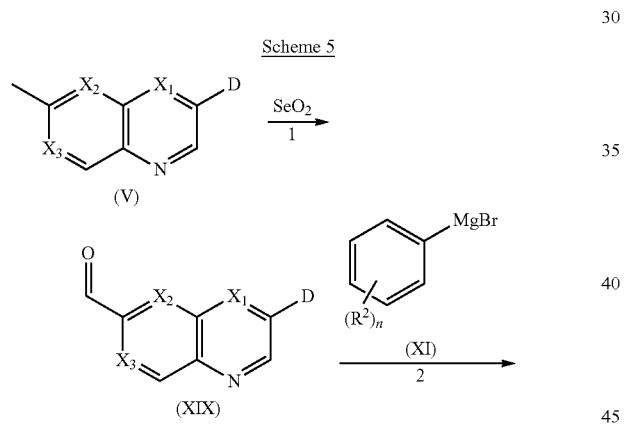

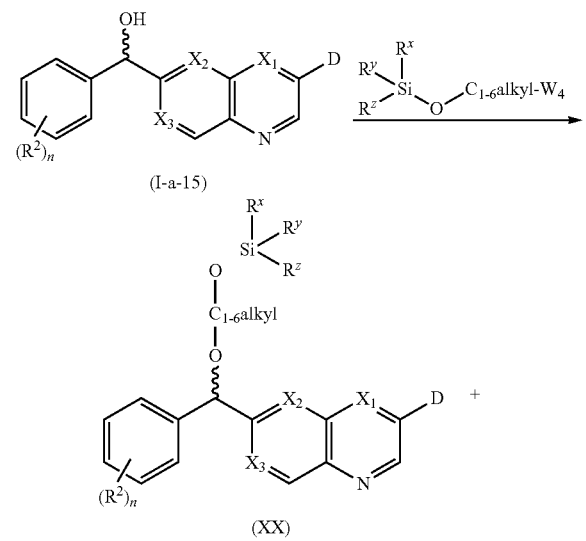

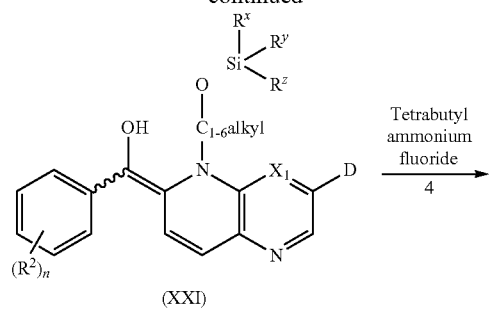

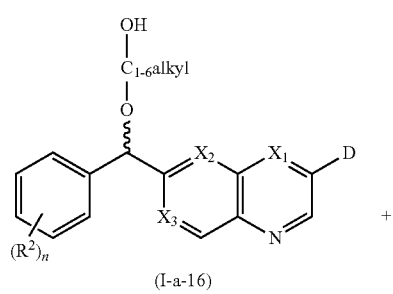

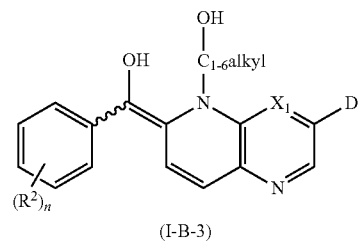

In Scheme 5, the following reaction conditions apply:

1: in the presence of a suitable solvent, such as for example dioxane;

2: in the presence of a suitable solvent, such as for example tetrahydrofuran;

3: in the presence of a suitable base, such as for example sodium hydride or potassium bis(trimethylsilyl)amide, and a suitable solvent, such as for example N,N-dimethylformamide or tetrahydrofuran, and wherein R$^x$ and R$^y$ represents C$_{1-4}$alkyl, and wherein R$^z$ represents C$_{1-4}$alkyl or phenyl, for instance R$^x$ and R$^y$ represent CH$_3$ and R$^z$ represents C(CH$_3$)$_3$ or phenyl, and wherein W$_4$ represents a suitable leaving group, such as for example halo, e.g. bromo;

4: in the presence of a suitable solvent, such as for example tetrahydrofuran.

Intermediates of formula (II-a) can be prepared according to the following reaction Scheme 6.

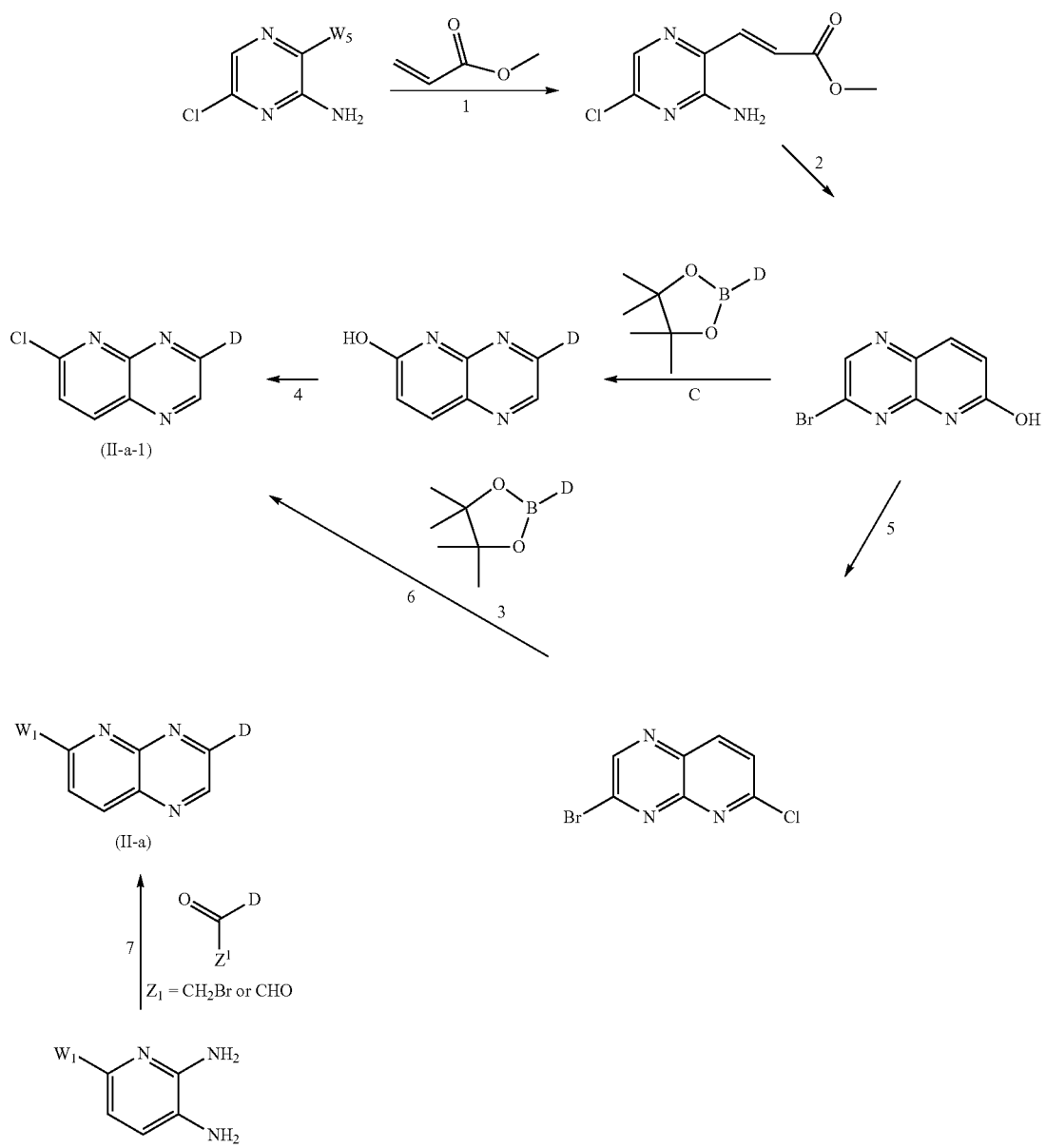

Scheme 6

In Scheme 6, the following reaction conditions apply:
1: in the presence of a suitable catalyst, such as for example tris(dibenzylideneacetone)dipalladium(0), a suitable ligand such as for example tri-tert-butyl-phosphonium tetrafluoroborate, a suitable base, such as for example diisopropylethylamine, and a suitable solvent, such as for example dioxane, and wherein $W_5$ represents a suitable leaving group, such as for example halo, e.g. bromo;
2: in the presence of bromidic acid and a suitable solvent, such as for example acetic acid;
3: in the presence of a suitable catalyst, such as for example Pd(PPh$_3$)$_4$, a suitable base, such as for example sodium carbonate, and a suitable solvent, such as for example ethylene glycol dimethylether and water;
4: in the presence of a suitable chlorinating agent, such as for example POCl$_3$, and a suitable solvents such as for example 1,2-dichloroethane and N,N-dimethylformamide
5: in the presence of a suitable chlorinating agent, such as for example POCl$_3$, and a suitable solvents such as for example 1,2-dichloroethane and N,N-dimethylformamide;
6: in the presence of a suitable catalyst, such as for example Pd(PPh$_3$)$_4$, a suitable base, such as for example sodium carbonate, and a suitable solvent, such as for example ethylene glycol dimethylether and water;
7: in the presence of a suitable base, such as for example N,N-diisopropylethylamine, and a suitable solvent, such as for example acetonitrile and wherein $W_1$ is as defined hereinabove.

Intermediates of formula (II-b) can be prepared according to the following reaction Scheme 7.

Scheme 7

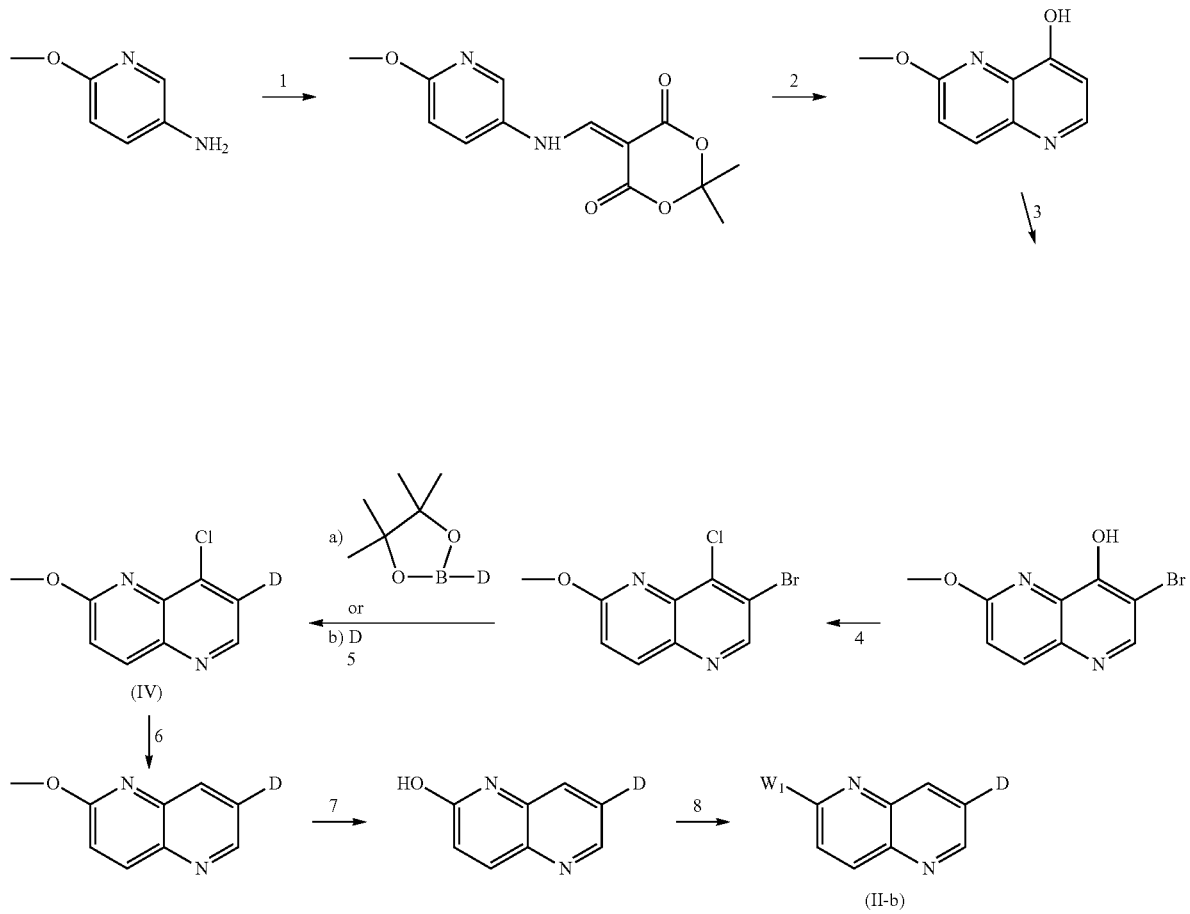

In Scheme 7, the following reaction conditions apply:
1: in the presence of a Meldrum's acid and triethyl orthoformate, and a suitable solvent, such as for example an alcohol, e.g. ethanol;
2: in the presence of diphenyl ether or dowtherm A;
3: in the presence of N-bromo-succinimide, and acetic acid;
4: in the presence of phosphoryl chloride, and a suitable solvent, such as for example chloroform;
5: a) in the presence of

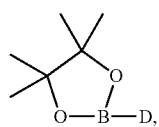

a suitable base, such as for example sodium carbonate, a suitable catalyst, such as for example PdCl$_2$(dppf).CH$_2$Cl$_2$, and a suitable solvent, such as for example dioxane and water;
or
b) alternatively, an intermediate of formula (IV) may be prepared by reacting the bromo-derivative with D in the presence of a suitable base, such as for example cesium carbonate, a ligand, such as for example 2,2'-bis(diphenylphosphino)-1,1'-binaphtalene (BINAP), and a catalyst, such as for example Pd(OAc)$_2$, in a suitable solvent, such as for example toluene.
6:
a) in the presence of a suitable catalyst, such as for example Raney nickel, and H$_2$, a suitable base, such as for example sodium hydroxide, and a suitable solvent, such as for example an alcohol, e.g. ethanol, and tetrahydrofuran;
or
b) in the presence of a suitable catalyst, such as for example PdCl$_2$(dppf).CH$_2$Cl$_2$, and hydrogen generation via catalytic hydrolysis of a suitable metal hydride, such as for example sodium borohydride, in the presence of a bidentate ligand, such as for example 1,2-bis(dimethylamino)ethane, in a suitable solvent, such as for example tetrahydrofuran. Preferably the reaction is performed under inert atmosphere (e.g. Argon atmosphere).
7: In the presence of a suitable acid, such as for example HCl, and a suitable solvent, such as for example, dioxane;
8: in the presence of a suitable leaving group introducing agent, such as for example phosphoryl chloride, and optionally a suitable solvent, such as for example chloroform.

Intermediates of formula (II-c) can be prepared according to the following reaction Scheme 8.

Scheme 8

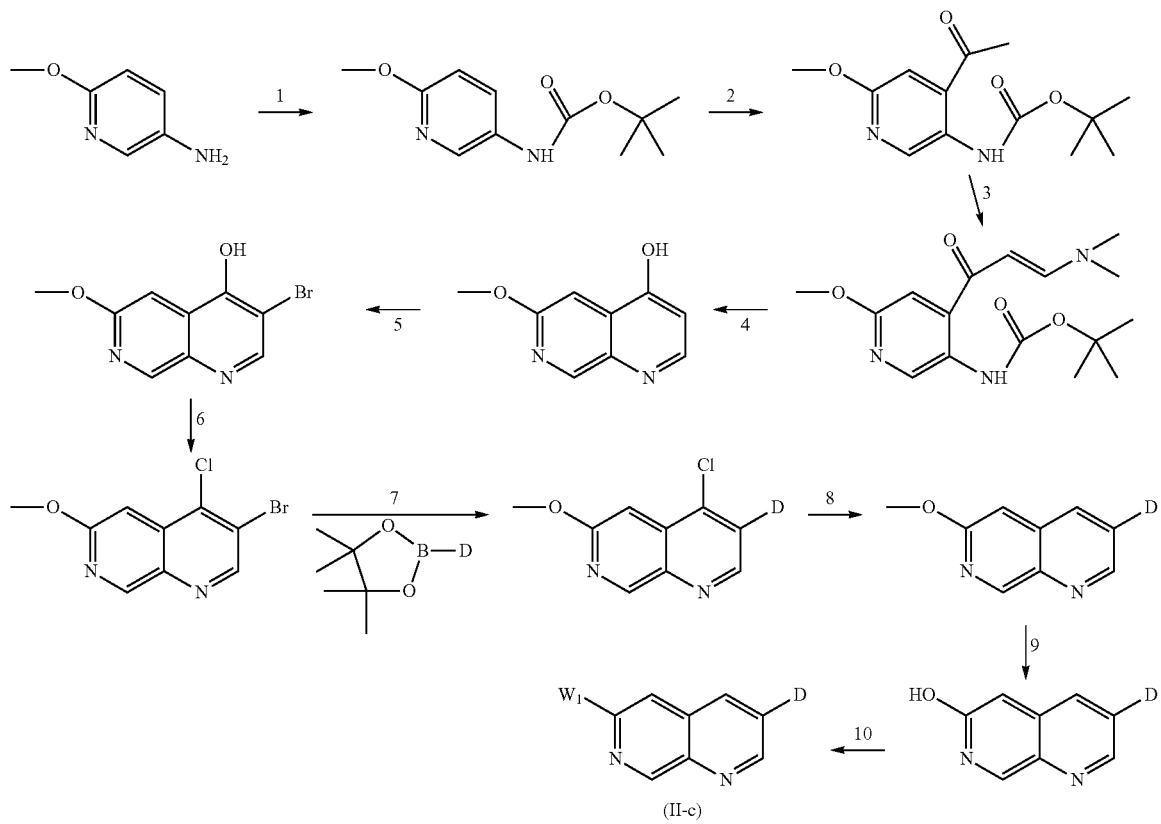

In Scheme 8, the following reaction conditions apply:
1: in the presence of di-tert-butyl dicarbonate, and a suitable solvent, e.g. dioxane;
2: in the presence of N-methoxy-N-methylacetamide, and tetramethylene diamine used as a base in the presence of BuLi;
3: in the presence of N,N-dimethylformamide and N,N-dimethylacetamide in a suitable solvent such as toluene;
4: in the presence of a suitable acid, such as for example trifluoroacetic acid, and a suitable solvent, such as for example dichloromethane;
5: in the presence of N-bromosuccinimide, and a suitable acid, such as for example acetic acid;
6: in the presence of POCl₃ and a suitable solvent, such as for example CHCl₃;
7; in the presence of a suitable base, such as for example sodium carbonate, a suitable catalyst, such as for example PdCl₂(pddf).CH₂Cl₂, and a suitable solvent, such as for example dioxane and water;
8: in the presence of catalyst, such as for example Raney nickel, and H₂, a suitable base, such as for example sodium hydroxide, and a suitable solvent, such as for example an alcohol, e.g. ethanol, and tetrahydrofuran;
9: in the presence of AlCl₃, and a suitable solvent, such as for example dichloroethane
10: in the presence of a leaving group introducing agent, such as for example phenyltriflimide, and a suitable solvent, such as for example toluene; or in the presence of phenyltriflimide and a suitable base, such as for example triethylamine, in a suitable solvent or a mixture of solvents, such as for example a mixture of dichloromethane/N,N-dimethylformamide.

Some of the intermediates are described in R. Morgentin et al., Tetrahedron 64 (2008) 2772-2782.

It is to be considered to be within the knowledge of the person skilled in the art to recognize which of the reactions described above for compounds of (I-A) are also applicable for compounds of formula (I-B).

It is considered to be within the knowledge of the person skilled in the art to recognize in which condition and on which part of the molecule a protective group may be appropriate. For instance, protective group on the R¹ substituent or on the D moiety, or protective group on the R³ᵃ substituent or on the R² substituent or combinations thereof. The skilled person is also considered to be able to recognize the most feasible protective group, such as for example —C(=O)—O—C₁₋₄alkyl or

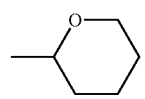

or —Si(CH₃)₂(C(CH₃)₃) or —CH₂—O—CH₂CH₂—O—CH₃. The skilled person is also considered to be able to recognize the most feasible deprotection reaction conditions, such as for example suitable acids, e.g. trifluoroacetic acid, hydrochloric acid, or suitable salts, such as for example tetrabutylammonium fluoride.

The skilled person is also considered to be able to recognize that when R¹ represents C(=O)-morpholinyl, said R¹ can be prepared from —C(=O)—NH—CH₂—

$CH_2$—O—$CH_2$—$CH_2$—O—$SO_2$— 4-methylphenyl, in the presence of sodium hydride, and a suitable solvent, such as for example N,N-dimethylformamide. Or that when $R^1$ represents —NH—C(=O)-morpholinyl, said $R^1$ can be prepared from —NH—C(=O)—O—C($CH_3$)$_3$ in the presence of morpholine, and a suitable solvent, such as for example 1-methyl-2-pyrrolidinone. Or that when $R^1$ represents hydroxyl$C_{1-6}$alkyl, e.g. —$CH_2$—$CH_2$—OH, said $R^1$ can be prepared from the corresponding alkoxycarbonyl intermediate, e.g. —$CH_2$—C(=O)—O—$CH_2$—$CH_3$, in the presence of Dibal-H 1M in hexane, and a suitable solvent, such as for example tetrahydrofuran.

The present invention also comprises deuterated compounds. These deuterated compounds may be prepared by using the appropriate deuterated intermediates during the synthesis process. For instance the below intermediate of formula (VI)

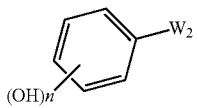

can be converted into the below intermediate of formula (VI)

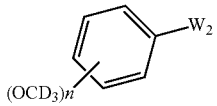

by reaction with iodomethane-D3 in the presence of a suitable base, such as for example cesium carbonate, and a suitable solvent, such as for example acetonitrile.

The compounds of the present invention may also be converted into each other via art-known reactions or functional group transformations.

For instance, compounds of formula (I-A) or (I-B) wherein $R^1$ represents tetrahydropyranyl can be converted into a compound of formula (I-A) or (I-B) wherein $R^1$ represents hydrogen, by reaction with a suitable acid, such as for example HCl or trifluoroacetic acid, in the presence of a suitable solvent, such as for example dichloromethane, dioxane, or an alcohol, e.g. methanol, isopropanol and the like.

Compounds of formula (I-A) or (I-B) wherein $R^1$ or $R^{3a}$ represent monohaloalkyl, can be converted into a compound of formula (I-A) or (I-B) wherein $R^1$ or $R^{3a}$ represent $C_{1-6}$alkyl substituted with a ring moiety as defined hereinabove and linked to the $C_{1-6}$alkyl moiety by the nitrogen atom, by reaction with a suitable ring moiety optionally in the presence of a suitable base, such as for example triethylamine or $K_2CO_3$ or sodium hydride, and optionally in the presence of a suitable solvent, such as for example acetonitrile, N,N-dimethylformamide or 1-methyl-2-pyrrolidinone.

Compounds of formula (I-A) or (I-B) wherein $R^1$ or $R^{3a}$ represents $C_{1-6}$alkyl-OH, can be converted into a compound of formula (I-A) or (I-B) wherein $R^1$ or $R^{3a}$ represent $C_{1-6}$alkyl-F by reaction with diethylaminosulfur trifluoride in the presence of a suitable solvent, such as for example dichloromethane and in the presence of catalytic amounts of an alcohol, such as for example ethanol. Likewise, a compound of formula (I-A) or (I-B) wherein $R^1$ or $R^{3a}$ represent $C_{1-6}$alkyl substituted with $R^6$ or $R^9$ wherein said $R^6$ or $R^9$ is substituted with OH, can be converted into a compound of formula (I-A) or (I-B) wherein $R^1$ or $R^{3a}$ represent $C_{1-6}$alkyl substituted with $R^6$ or $R^9$ wherein said $R^6$ or $R^9$ is substituted with F, by reaction with diethylaminosulfur trifluoride in the presence of a suitable solvent, such as for example dichloromethane.

Compounds of formula (I-A) or (I-B) wherein $R^1$ or $R^{3a}$ represent $C_{1-6}$alkyl substituted with $R^6$ or $R^9$ wherein said $R^6$ or $R^9$ is substituted with —C(=O)—O—$C_{1-6}$alkyl, can be converted into a compound of formula (I-A) or (I-B) wherein $R^1$ or $R^{3a}$ represent $C_{1-6}$alkyl substituted with $R^6$ or $R^9$ wherein said $R^6$ or $R^9$ is substituted with —$CH_2$—OH, by reaction with a suitable reducing agent such as for example $LiAlH_4$, in the presence of a suitable solvent, such as for example tetrahydrofuran.

Compounds of formula (I-A) or (I-B) wherein $R^{3a}$ represents $C_{1-6}$alkyl substituted with 1,3-dioxo-2H-isoindol-2-yl, can be converted into a compound of formula (I-A) or (I-B) wherein $R^{3a}$ represents $C_{1-6}$alkyl substituted with amino, by reaction with hydrazine monohydrate in the presence of a suitable solvent, such as for example an alcohol, e.g. ethanol.

Compounds of formula (I-A) or (I-B) wherein $R^1$ or $R^{3a}$ represent $C_{1-6}$alkyl substituted with amino, can be converted into a compound of formula (I-A) or (I-B) wherein $R^1$ or $R^{3a}$ represents $C_{1-6}$alkyl substituted with —NH—S(=O)$_2$—$C_{1-6}$alkyl, by reaction with Cl—S(=O)$_2$—$C_{1-6}$alkyl in the presence of a suitable base, such as for example triethylamine, and a suitable solvent, such as for example dichloromethane.

Compounds of formula (I-A) or (I-B) wherein $R^1$ or $R^{3a}$ represents $C_{1-6}$alkyl substituted with halo, can be converted into a compound of formula (I-A) or (I-B) wherein $R^1$ or $R^{3a}$ represent $C_{1-6}$alkyl substituted with $NR^4R^5$ or $NR^{10}R^{11}$, by reaction with $NHR^4R^5$ or $NHR^{10}R^{11}$, either using such amino in large excess or in the presence of a suitable base, such as for example $K_2CO_3$, and a suitable solvent, such as for example acetonitrile, N,N-dimethylacetamide or 1-methyl-pyrrolidinone.

Compounds of formula (I-A) or (I-B) wherein $R^1$ represents hydrogen, can be converted into a compound of formula (I-A) or (I-B) wherein $R^1$ represents polyhalo-$C_{1-6}$alkyl or polyhydroxy$C_{1-6}$alkyl or $C_{1-6}$alkyl or —S(=O)$_2$—$NR^{14}R^{15}$ or S(=O)$_2$—$C_{1-6}$alkyl, by reaction with polyhalo$C_{1-6}$alkyl-W or polyhydroxy$C_{1-6}$alkyl-W or $C_{1-6}$alkyl-W or W—S(=O)$_2$—$NR^{14}R^{15}$ or W—S(=O)$_2$—$C_{1-6}$alkyl, wherein W represents a suitable leaving group, such as for example halo, e.g. bromo and the like, in the presence of a suitable base, such as for example sodium hydride or $K_2CO_3$ or triethylamine or 4-dimethylaminopyridine or diisopropylamine, and a suitable solvent, such as for example N,N-dimethylformamide or acetonitrile or dichloromethane.

Compounds of formula (I-A) or (I-B) wherein $R^1$ represents hydrogen can also be converted into a compound of formula (I-A) or (I-B) wherein $R^1$ represents $C_{1-6}$alkyl-OH, by reaction with W—$C_{1-6}$alkyl-O—Si($CH_3$)$_2$(C($CH_3$)$_3$) in the presence of a suitable base, such as for example sodium hydride, and a suitable solvent, such as for example N,N-dimethylformamide. The skilled person will realize that this step is followed by reaction with a suitable acid, such as for example trifluoroacetic acid, in a suitable solvent, such as for example tetrahydrofuran, or by reaction with tetrabutyl ammonium fluoride in the presence of a suitable solvent, such as for example tetrahydrofuran.

Compounds of formula (I-A) or (I-B) wherein $R^1$ represents hydrogen, can also be converted into compound of formula (I-A) or (I-B) wherein $R^1$ represents ethyl substituted with —S(=O)$_2$—C$_{1-6}$alkyl, by reaction with C$_{1-6}$alkyl-vinylsulfone, in the presence of a suitable base, such as for example triethylamine, and a suitable solvent, such as for example an alcohol, e.g. methanol or by reaction with C$_{1-6}$alkyl-2-bromoethylsulfone in the presence of a suitable deprotonating agent, such as for example NaH, and a suitable solvent, such as for example dimethylformamide.

Compounds of formula (I-A) or (I-B) wherein $R^1$ represents hydrogen can also be converted into a compound of formula (I) wherein $R^1$ represents

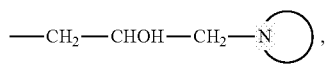

by reaction with

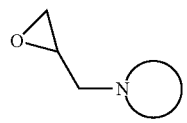

in the presence of a suitable base, such as for example sodium hydride, and a suitable solvent, such as for example N,N-dimethylformamide, wherein

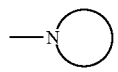

represents a suitable nitrogen containing ring within the definition of $R^6$.

Compounds of formula (I-A) or (I-B) wherein $R^1$ represents C$_{1-6}$alkyl substituted with $R^6$ wherein said $R^6$ is substituted with —C(=O)—O—C$_{1-6}$alkyl or —S(=O)$_2$—NR$^{14}$R$^{15}$ or wherein $R^3$ represents C$_{1-6}$alkyl substituted with $R^9$ wherein said $R^9$ is substituted with —C(=O)—O—C$_{1-6}$alkyl or —S(=O)$_2$—NR$^{14}$R$^{15}$, can be converted into a compound of formula (I) wherein the $R^6$ or $R^9$ is unsubstituted, by reaction with a suitable acid, such as for example HCl and a suitable solvent, such as for example dioxane, acetonitrile or an alcohol, e.g. isopropylalcohol. Compounds of formula (I-A) or (I-B) wherein $R^1$ represents C$_{1-6}$alkyl substituted with $R^6$ wherein said $R^6$ is a ring moiety comprising a nitrogen atom which is substituted with —CH$_2$—OH or wherein $R^{3a}$ represents C$_{1-6}$alkyl substituted with $R^9$ wherein said $R^9$ is a ring moiety comprising a nitrogen atom which is substituted with —CH$_2$—OH, can be converted into a compound of formula (I) wherein the $R^6$ or $R^9$ is unsubstituted, by reaction with sodium hydroxide, in the presence of a suitable solvent, such as for example tetrahydrofuran.

Compounds of formula (I-A) or (I-B) wherein $R^1$ represents C$_{1-6}$alkyl substituted with $R^6$ or $R^{3a}$ represents C$_{1-6}$alkyl substituted with $R^9$, wherein said $R^6$ or said $R^9$ is unsubstituted, can be converted into a compound of formula (I-A) or (I-B) wherein said $R^6$ or said $R^9$ is substituted with C$_{1-6}$alkyl, by reaction with W—C$_{1-6}$alkyl wherein W is as defined above, in the presence of a suitable base. Such as for example sodium hydride, and a suitable solvent, such as for example N,N-dimethylformamide.

Compounds of formula (I-A) or (I-B) wherein $R^1$ or $R^{3a}$ represent hydroxyC$_{1-6}$alkyl, can be converted into the corresponding carbonyl compound, by reaction with dess-Martin-periodinane, in the presence of a suitable solvent, such as for example dichloromethane.

Compounds of formula (I-A) or (I-B) wherein $R^1$ represents C$_{1-6}$alkyl substituted with $R^6$ or $R^{3a}$ represents C$_{1-6}$alkyl substituted with $R^9$, wherein said $R^6$ or said $R^9$ is substituted with C$_{1-6}$alkyl-halo, can be converted into a compound of formula (I-A) or (I-B) wherein said $R^6$ or said $R^9$ is substituted with C$_{1-6}$alkyl-CN, by reaction with sodium cyanide, in the presence of a suitable solvent, such as for example water or an alcohol, e.g. ethanol.

Compounds of formula (I-A) or (I-B) wherein $R^1$ represents C$_{1-6}$alkyl substituted with $R^6$ wherein said $R^6$ is unsubstituted or wherein $R^{3a}$ represents C$_{1-6}$alkyl substituted with $R^9$ wherein said $R^9$ is unsubstituted, can be converted into a compound of formula (I-A) or (I-B) wherein $R^6$ or $R^9$ is substituted with —CH$_3$ or CH(CH$_3$)$_2$, by reaction with formaldehyde or acetone and NaBH$_3$CN, in the presence of a suitable solvent, such as for example tetrahydrofuran or an alcohol, e.g. methanol.

Compounds of formula (I-A) or (I-B) wherein $R^1$ contains a $R^6$ substituent substituted with OH or wherein $R^{3a}$ contains a $R^9$ substituent substituted with OH, can be converted into a compound of formula (I-A) or (I-B) wherein the $R^6$ or $R^9$ substituent is substituted with C$_{1-6}$alkyloxy, by reaction with W—C$_{1-6}$alkyl, in the presence of a suitable base, such as for example sodium hydride, and a suitable solvent, such as for example N,N-dimethylformamide.

Compounds of formula (I-A) or (I-B) wherein $R^1$ contains a $R^6$ substituent substituted with C$_{1-6}$alkyloxy or wherein $R^{3a}$ contains a $R^9$ substituent substituted with C$_{1-6}$alkyloxy, can be converted into a compound of formula (I) wherein the $R^6$ or $R^9$ substituent is substituted with —OH by reaction with a suitable acid, such as for example hydrochloric acid.

Compounds of formula (I-A) or (I-B) wherein $R^1$ contains a $R^6$ substituent substituted with halo or wherein $R^{3a}$ contains a $R^9$ substituent substituted with halo can be converted into a compound of formula (I-A) or (I-B) wherein the $R^6$ or $R^9$ substituent is substituted with NR$^{14}$R$^{15}$ by reaction with NHR$^{14}$R$^{15}$ in a suitable solvent, such as for example 1-methyl-pyrrolidinone.

Compounds of formula (I-A) or (I-B) wherein $R^{3a}$ represents C$_{1-6}$alkyl substituted with C(=O)—O—C$_{1-6}$alkyl, can be converted into a compound of formula (I-A) or (I-B) wherein $R^{3a}$ represents C$_{1-6}$alkyl substituted with COOH, by reaction with LiOH in the presence of a suitable solvent, such as for example tetrahydrofuran. Said compounds of formula (I-A) or (I-B) wherein $R^{3a}$ represents C$_{1-6}$alkyl substituted with COOH, can be converted to a compound of formula (I-A) or (I-B) wherein $R^{3a}$ represents C$_{1-6}$alkyl substituted with —C(=O)—NH$_2$ or —C(=O)—NHCH$_3$ or —C(=O)NR$^{10}$R$^{11}$, by reaction with NH(Si(CH$_3$)$_3$)$_2$ or MeNH$_3^+$Cl$^-$ or NHR$^{10}$R$^{11}$ in the presence of suitable peptide coupling reagents such as for example 1-(3-dimethylaminopropyl)-3-ethylcarbodiimide HCl and 1-hydroxybenzotriazole, a suitable base, such as for example triethylamine and a suitable solvent such as for example dichloromethane or N,N-dimethylformamide. Compounds of formula (I-A) or (I-B) wherein $R^{3a}$ represents C$_{1-6}$alkyl substituted with —C(=O)—O—C$_{1-6}$alkyl, can also be converted into a compound of formula (I-A) or (I-B) wherein $R^{3a}$ represents C$_{1-6}$alkyl substituted with 4,5-dihydro-imidazol-2-yl, by reaction under N2 with ethylenediamine and trimethylaluminium in the presence of a suitable solvent, such as for example toluene and heptane. Compounds of formula (I-A)

or (I-B) wherein $R^{3a}$ represents $C_{1-6}$alkyl substituted with COOH, can also be converted into a compound of formula (I-A) or (I-B) wherein $R^{3a}$ represents $C_{1-6}$alkyl substituted with —C(=O)—N(CH$_3$)(OCH$_3$) by reaction with dimethylhydroxylamine, in the presence of carbonyldiimidazole and a suitable solvent, such as for example dichloromethane.

Compounds of formula (I-A) or (I-B) wherein $R^{3a}$ represents $C_{1-6}$alkyl substituted with

can be converted into a compound of formula (I-A) or (I-B) wherein $R^{3a}$ represents $C_{1-6}$alkyl substituted with 2 OH's, by reaction with a suitable acid, such as for example trifluoroacetic acid, and a suitable solvent, such as for example dioxane or water. These compounds of formula (I-A) or (I-B) wherein $R^{3a}$ represents $C_{1-6}$alkyl substituted with

can also be converted into a compound of formula (I-A) or (I-B) wherein $R^{3a}$ represents $C_{1-6}$alkyl substituted with OH and $NR^{10}R^{11}$, by reaction with $NH_2R^{10}R^{11}$ optionally in salt form, such as for example $NHR^{10}R^{11+}Cl^-$, optionally in the presence of a suitable base, such as for example sodium hydride or $Na_2CO_3$ or triethylamine, a suitable additive such as for example KI, and in the presence of a suitable solvent, such as for example N,N-dimethylformamide or an alcohol, e.g. 1-butanol or ethanol.

Compounds of formula (I-A) or (I-B) wherein $R^{3a}$ represents $C_{1-3}$alkyl substituted with —C(=O)—O—$C_{1-6}$alkyl, can be converted into a compound of formula (I-A) or (I-B) wherein $R^3$ represents $C_{1-3}$alkyl substituted with —C(CH$_3$)$_2$—OH, by reaction with iodomethane and Mg powder, in the presence of a suitable solvent, such as for example diethylether or tetrahydrofuran.

Compounds of formula (I-A) or (I-B) wherein $R^{3a}$ represents $C_{1-5}$alkyl substituted with —C(=O)—O—$C_{1-6}$alkyl, can be converted into a compound of formula (I-A) or (I-B) wherein $R^3$ represents $C_{1-6}$alkyl substituted with —OH, by reaction with a suitable reducing agent such as for example LiAlH$_4$, in a suitable solvent, such as for example tetrahydrofuran. Compounds of formula (I-A) or (I-B) wherein $R^{3a}$ represents $C_{1-5}$alkyl substituted with —OH, can be converted into a compound of formula (I-A) or (I-B) wherein $R^{3a}$ represents $C_{1-5}$alkyl substituted with —O—C(=O)—$C_{1-6}$alkyl by reaction with Cl—C(=O)—$C_{1-6}$alkyl in the presence of a suitable base, such as for example NaH, and a suitable solvent, such as for example tetrahydrofuran.

Compounds of formula (I-A) or (I-B) wherein $R^{3a}$ represents CH$_2$—CH=CH$_2$, can be converted into a compound of formula (I-A) or (I-B) wherein $R^{3a}$ represents CH$_2$—CHOH—CH$_2$—OH, by reaction with potassium permanganate, and a suitable solvent, such as for example acetone or water.

Compounds of formula (I-A) or (I-B) wherein $R^{3a}$ represents $C_{1-6}$alkyl substituted with —C(=O)—$C_{1-4}$alkyl, can be converted into a compound of formula (I-A) or (I-B) wherein $R^{3a}$ represents $C_{1-6}$alkyl substituted with —C($C_{1-4}$alkyl)=N—OH, by reaction with hydroxylamine, in the presence of a suitable base, such as for example pyridine, and a suitable solvent, such as for example an alcohol, e.g. ethanol.

Compounds of formula (I-A) or (I-B) wherein $R^{3a}$ represents $C_{1-6}$alkyl substituted with NH$_2$, can be converted into a compound of formula (I-A) or (I-B) wherein $R^{3a}$ represents $C_{1-6}$alkyl substituted with —NH—C(=O)—$R^6$ or with —NH—C(=O)—$C_{1-6}$alkyl or with —NH—C(=O)-polyhydroxy$C_{1-6}$alkyl or with —NH—C(=O)-polyhalo-$C_{1-6}$alkyl or with —NH—C(=O)-polyhydroxypolyhalo-$C_{1-6}$alkyl, by reaction with the corresponding COOH analogue, e.g. $R^6$—COOH or CF$_3$—C(CH$_3$)(OH)—COOH and the like, in the presence of suitable peptide coupling reagents such as 1-hydroxy-benzotriazole and 1-(3-dimethylamino)propyl)carbodiimide optionally in the presence of a suitable base, such as for example triethylamine. Said compounds of formula (I-A) or (I-B) wherein $R^{3a}$ represents $C_{1-6}$alkyl substituted with NH$_2$, can also be converted into a compound of formula (I-A) or (I-B) wherein $R^{3a}$ represents $C_{1-6}$alkyl substituted with NH—C(=O)—CF$_3$, by reaction with trifluoroacetic anhydride, in the presence of a suitable base, such as for example triethylamine, and a suitable solvent, such as for example tetrahydrofuran. Said compounds of formula (I-A) or (I-B) wherein $R^{3a}$ represents $C_{1-6}$alkyl substituted with NH$_2$, can also be converted into a compound of formula (I) wherein $R^3$ represents $C_{1-6}$alkyl substituted with NH-polyhalo$C_{1-6}$alkyl, e.g. NH—CH$_2$—CH$_2$—F, by reaction with polyhalo$C_{1-6}$ alkyl-W, with W as defined above, e.g. iodo-2-fluoroethane, in the presence of a suitable base, such as for example $K_2CO_3$, and a suitable solvent, such as for example N,N-dimethylformamide or dioxane.

Compounds of formula (I-A) or (I-B) wherein $R^{3a}$ represents $C_{1-6}$alkyl substituted with cyano, can be converted into a compound of formula (I) wherein $R^3$ represents $C_{1-6}$alkyl substituted with tetrazolyl by reaction with sodium azide, and $NH_4^+Cl^-$ in the presence of a suitable solvent, such as for example N,N-dimethylformamide.

Compounds of formula (I) wherein $R^3$ represents —CH$_2$C≡CH, can be converted into a compound of formula (I-A) or (I-B) wherein $R^{3a}$ represents

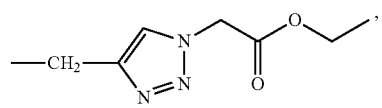

by reaction with ethyl azidoacetate in the presence of CuI and a suitable base, such as for example diisopropylamine, and a suitable solvent, such as for example tetrahydrofuran. Compounds of formula (I-A) or (I-B) wherein $R^{3a}$ represents —CH$_2$C≡CH, can be converted into a compound of formula (I-A) or (I-B) wherein $R^{3a}$ represents

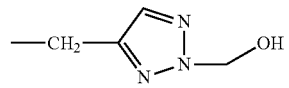

by reaction with sodium azide and formaldehyde, in the presence of a suitable catalyst, such as for example CuSO$_4$ and sodium L ascorbate, a suitable acid, such as for example acetic acid, and a suitable solvent, such as for example dioxane.

Compounds of formula (I-A) or (I-B) wherein $R^{3a}$ represent $C_{2-6}$alkynyl, can be converted into a compound of formula (I-A) or (I-B) wherein $R^{3a}$ represents $C_{2-6}$alkynyl substituted with $R^9$, by reaction with W—$R^9$ wherein W is as defined above, in the presence of a suitable catalyst, such as for example dichlorobis(triphenylphosphine)palladium, a suitable co-catalyst such as CuI, a suitable base, such as for example triethylamine, and a suitable solvent, such as for example dimethylsulfoxide.

Compounds of formula (I-A) or (I-B) wherein $R^{3a}$ comprises $R^9$ substituted with halo, can be converted into a compound of formula (I-A) or (I-B) wherein $R^{3a}$ comprises $R^9$ substituted with —$NR^{14}R^{15}$ by reaction with $NHR^{14}R^{15}$ in the presence of a suitable solvent, such as for example 1-methyl-2-pyrrolidinone.

Compounds of formula (I-A) or (I-B) wherein $R^{3a}$ comprises $C_{2-6}$alkynyl, can be hydrogenated into a compound of formula (I-A) or (I-B) wherein $R^{3a}$ comprises $C_{2-6}$alkyl in the presence of a suitable catalyst, such as for example palladium on charcoal, and a suitable solvent, such as for example ethylacetate.

Compounds of formula (I-A) or (I-B) wherein $R^{3a}$ comprises $C_{2-6}$alkynyl, can be hydrogenated into a compound of formula (I-A) or (I-B) wherein $R^{3a}$ comprises $C_{2-6}$alkenyl in the presence of a suitable catalyst, such as for example Lindlar catalyst, and a suitable solvent, such as for example ethylacetate.

Compounds of formula (I-A) or (I-B) wherein $R^{3a}$ represents $C_{1-6}$alkyl substituted with —P(=O)(OC$_{1-6}$alkyl)$_2$ can be converted into a compound of formula (I-A) or (I-B) wherein $R^{3a}$ represents $C_{1-6}$alkyl substituted with —P(=O)(OH)$_2$ by reaction with bromotrimethylsilane in the presence of a suitable solvent, such as for example dichloromethane.

Compounds of formula (I-A) or (I-B) wherein the $R^9$ substituent is substituted with =O, can be converted into the corresponding reduced $R^9$ substituent by reaction with a suitable reducing agent, such as for example LiAlH$_4$ in a suitable solvent, such as for example tetrahydrofuran.

Compounds of formula (I-A) or (I-B) wherein $R^{3a}$ comprises —$NHR^{10}$ can be converted into a compound of formula (I-A) or (I-B) wherein $R^{3a}$ comprises —$NR^{10}$—(C=O)-optionally substituted $C_{1-6}$alkyl, by reaction with the corresponding W—(C=O)-optionally substituted $C_{1-6}$alkyl wherein W represents a suitable leaving group, such as for example halo, e.g. chloro and the like, in the presence of a suitable base, such as for example triethylamine, and a suitable solvent, such as for example acetonitrile.

Compounds of formula (I-A) or (I-B) wherein $R^{3a}$ represents $C_{1-6}$alkyl substituted with $NR^{10}$(benzyl) can be converted into a compound of formula (I-A) or (I-B) wherein $R^{3a}$ represents $C_{1-6}$alkyl substituted with $NHR^{10}$, by reaction with 1-chloroethylchloroformate in the presence of a suitable solvent, such as for example dichloromethane.

Compounds of formula (I-A) or (I-B) wherein $R^1$ represents unsubstituted piperidine, can be converted into a compound of formula (I-A) or (I-B) wherein $R^1$ represents 1-methyl-piperidine, by reaction with iodomethane in the presence of a suitable base, such as for example potassium carbonate, and a suitable solvent, such as for example acetonitrile. Compounds of formula (I-A) or (I-B) wherein $R^1$ represents hydrogen can be converted into a compound of formula (I-A) or (I-B) wherein $R^1$ represents optionally substituted $C_{1-6}$alkyl, by reaction with optionally substituted $C_{1-6}$alkyl-W wherein W represents a suitable leaving group, such as for example halo, e.g. bromo and the like, in the presence of a suitable base, such as for example potassium carbonate, and a suitable solvent, such as for example acetonitrile.

Compounds of formula (I-A) or (I-B)) wherein $R^2$ represents halo, e.g. bromo, can be converted into a compound of formula (I-A) or (I-B) wherein $R^2$ represents cyano, by reaction with zinc cyanide, in the presence of a suitable catalyst, such as for example Pd$_2$(dba)$_3$ and a suitable ligand, such as for example 1,1-bis(diphenylphosphino)ferrocene, in the presence of a suitable solvent, such as for example N,N-dimethylformamide.

Said $R^2$ substituent being cyano can be converted into —$CH_2$—$NH_2$ by hydrogenation in the presence of $NH_3$ and Nickel.

Compounds of formula (I-A) or (I-B) wherein $R^2$ represents —$OCH_3$ can be converted into a compounds of formula (I-A) or (I-B) wherein $R^2$ represents —OH by reaction with boron tribromide in the presence of a suitable solvent, such as for example dichloromethane.

Compounds of formula (I-A) or (I-B) wherein $R^2$ represents —OH can be converted into a compounds of formula (I-A) or (I-B) wherein $R^2$ represents —$OCH_3$ by reaction with methyl iodine in the presence of a suitable base, such as for example potassium carbonate, and a suitable solvent, such as for example N,N-dimethylformamide.

Compounds of formula (I-A) or (I-B) wherein $R^2$ represents hydrogen, can be converted into a compound of formula (I-A) or (I-B) wherein $R^2$ represents —CHOH—$CF_3$ by reaction with trifluoroacetaldehyde methyl hemiketal.

Compounds of formula (I-A) wherein $R^{3a}$ and $R^{3b}$ are taken together to form =O can be reduced to the corresponding alcohol by using any suitable reduction reaction known to the skilled person, for example in the presence of a reducing agent, such as for example sodium borohydride, in the presence of a suitable solvent or a mixture of solvents, such as for example a mixture of methanol/dichloromethane. Preferably the reaction is performed under inert atmosphere (e.g. Argon atmosphere) at 0° C.

Compounds of formula (I-A) wherein $R^{3a}$ and $R^{3b}$ are taken together to form =O, can be converted to compounds of formula (I-A) wherein $R^{3a}$ and $R^{3b}$ are taken together to form =CH—CN, in the presence of a suitable cyanide source, such as for example diethyl cyanophosphonate, and a suitable base, such as for example sodium hydride, in a suitable solvent, such as for example tetrahydrofuran. Preferably the reaction is performed under inert atmosphere (e.g. Argon atmosphere) at 0° C.

A further aspect of the invention is a process for the preparation of a compound of formula (I-A) or (I-B) as defined herein, which process comprises:
(i) reacting an intermediate of formula

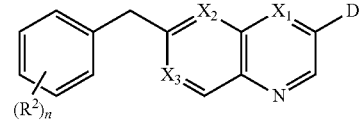

(VIII)

with W$_3$—R$^{3'}$ in the presence of a suitable base, such as for example butyl lithium, and a suitable solvent, such as for example tetyrhydrofuran, and wherein W$_3$ represents a suitable leaving group, such as for example halo, e.g. bromo and the like, and R$^{3'}$ represents optionally substituted $C_{1-6}$alkyl;

(ii) reacting an intermediate of formula

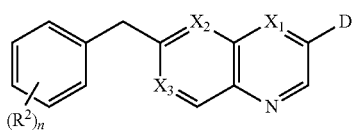
(VIII)

with $R^9$—$C_{1-6}$alkyl-$W_3$ in the presence of a suitable base, such as for example butyl lithium, and a suitable solvent, such as for example tetyrhydrofuran, and wherein $W_3$ represents a suitable leaving group, such as for example halo, e.g. bromo and the like;

(iii) reacting an intermediate of formula

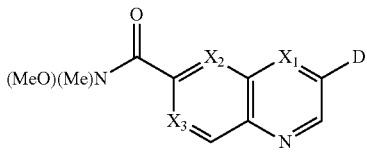
(X)

with an intermediate of formula (XI)

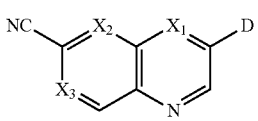
(XI)

in the presence of a suitable solvent, such as for example tetrahydrofuran;

(iv) reacting an intermediate of formula

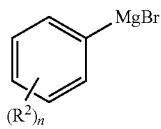
(XIII)

with an intermediate of formula (XI)

in the presence of a suitable solvent, such as for example toluene;

(v) reacting an intermediate of formula

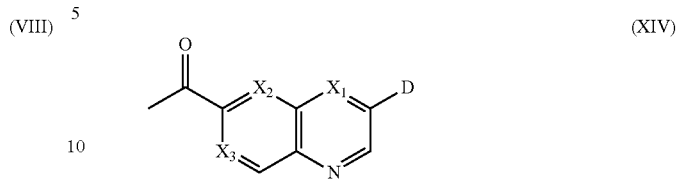
(XIV)

with an intermediate of formula

(XI)

in the presence of a suitable solvent, such as for example tetrahydrofuran;

(vi) reacting an intermediate of formula

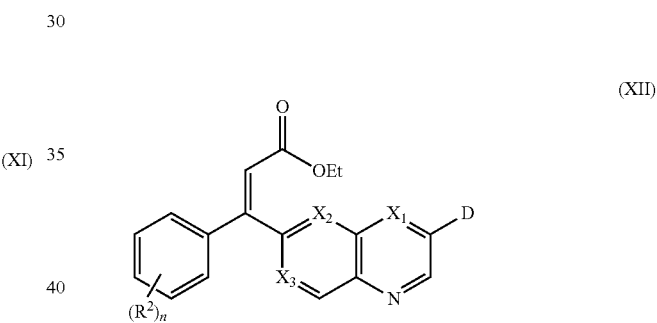
(XII)

with $NHR^{14}R^{15}$ in the presence of a suitable lewis acid, such as for example trimethylaluminium, and a suitable solvent, such as for example toluene;

(vii) deprotecting an intermediate of formula

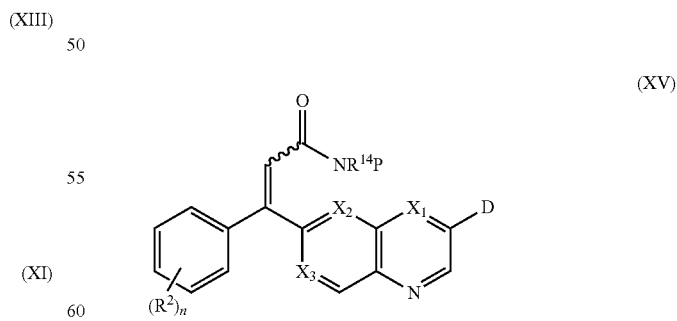
(XV)

wherein P represents a suitable protective group, such as for example —C(=O)—OC(CH$_3$)$_3$ in the presence of a suitable acid, such as for example HCl or trifluoroacetic acid, and a suitable solvent, such as for example an alcohol, e.g. methanol, or dichloromethane;

(viii) deprotecting an intermediate of formula

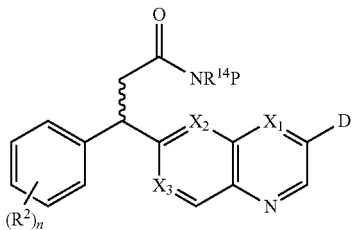
(XVI)

in the presence of a suitable acid, such as for example HCl or trifluoroacetic acid, and a suitable solvent, such as for example an alcohol, e.g. methanol, or dichloromethane;

(ix) converting a compound of formula

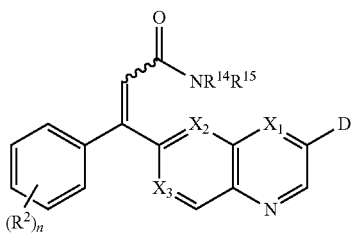
(I-A-5)

with a suitable reducing agent, such as for example $BH_3.Me_2$ or $NaBH_4$ in a suitable solvent such as for example dioxane or tetrahydrofuran;

(x) converting a compound of formula

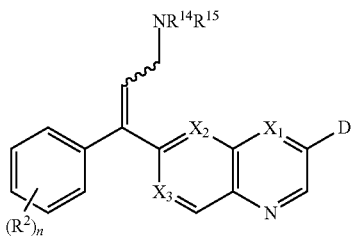
(I-A-6)

with a suitable reducing agent, such as Mg, and a suitable solvent, such as for example tetrahydrofuran or a suitable alcohol, e.g. methanol;

(xi) reacting an intermediate of formula

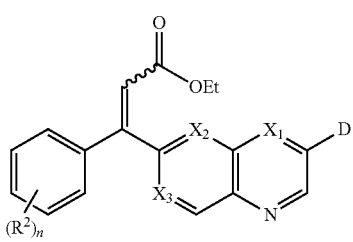
(XII)

in the presence of Mg and a suitable solvent, such as for example tetrahydrofuran or a suitable alcohol, e.g. methanol; or in the presence of $H_2$ and a suitable catalyst, such as for example palladium on charcoal, and a suitable solvent, such as for example tetrahydrofuran;

(xii) converting a compound of formula

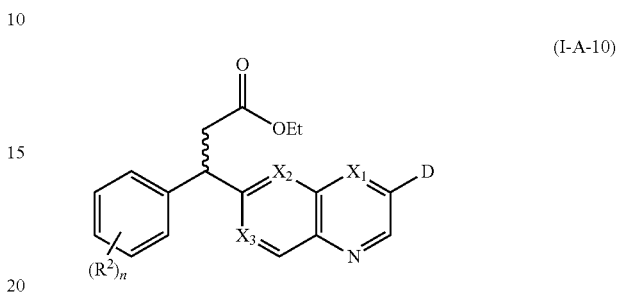
(I-A-10)

with a suitable reducing agent, such as for example lithium aluminium hydride, in the presence of a suitable solvent, such as for example tetrahydrofuran;

(xiii) reacting an intermediate of formula

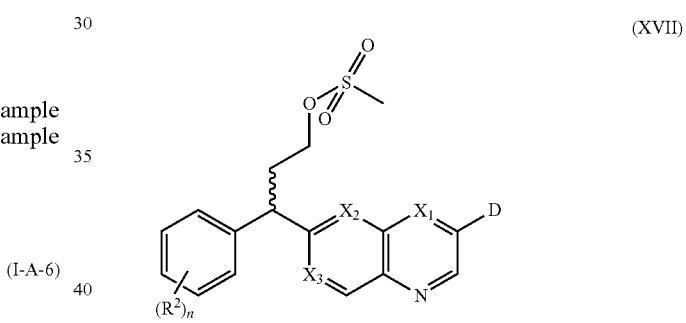
(XVII)

with a suitable base of formula

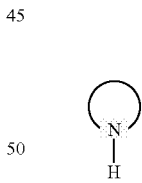

or $NHR^{10}R^{11}$ optionally in the presence of a suitable base, such as for example triethylamine, potassium carbonate, sodium carbonate or sodium hydride, and optionally a suitable solvent, such as for example acetonitrile, tetrahydrofuran, N,N-dimethylformamide. This reaction can also be performed with a suitable salt of

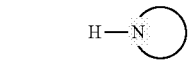

which is a suitable nitrogen containing ring (unsubstituted or substituted) within the definition of $R^9$;

(xiv) deprotecting an intermediate of formula

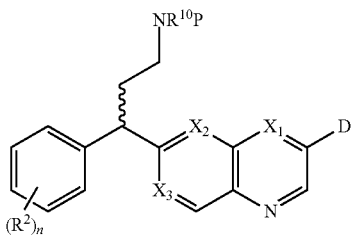

(XVIII)

wherein P represents a suitable protective group, such as for example —C(=O)—OC(CH$_3$)$_3$, in the presence of a suitable acid, such as for example HCl or trifluoroacetic acid, and a suitable solvent, such as for example an alcohol, e.g. methanol, or dichloromethane;

(xv) reacting an intermediate of formula

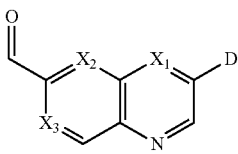

(XIX)

with an intermediate of formula

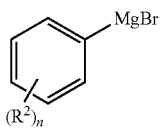

(XI)

in the presence of a suitable solvent, such as for example tetrahydrofuran;

(xvi) reacting an intermediate of formula (XX) or (XXI)

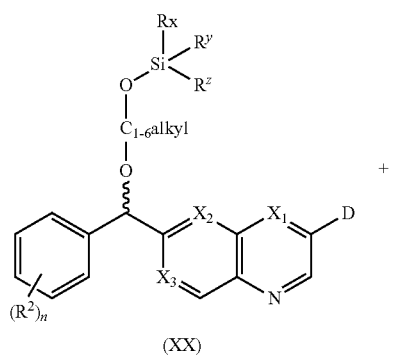

(XX)

+

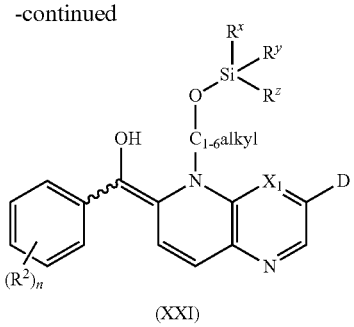

(XXI)

wherein R$^x$ and R$^y$ represent C$_{1-4}$alkyl, and wherein R$^z$ represents C$_{1-4}$alkyl or phenyl, for instance R$^x$ and R$^y$ represent CH$_3$ and R$^z$ represents C(CH$_3$)$_3$ or phenyl, with tetrabutyl ammonium fluoride in the presence of a suitable solvent, such as for example tetrahydrofuran;
wherein the variables are as defined herein; and optionally thereafter converting one compound of the formula (I-A) or (I-B) into another compound of the formula (I-A) or (I-B).

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or tautomers or solvates or protected forms thereof, even more preferably the salts or tautomers or solvates thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof. According to a further aspect of the invention there is provided a compound as defined herein or a salt or solvate thereof. References to compounds of the formula (I) and sub-groups thereof as defined herein include within their scope the salts or solvates or tautomers or N-oxides of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphorsulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g.naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth metal cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide.

Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by formula (I) are any complexes (e.g. inclusion complexes or clathrates with compounds such as cyclodextrins, or complexes with metals) of the compounds.

Furthermore, the compounds of the present invention may have one or more polymorph (crystalline) or amorphous forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

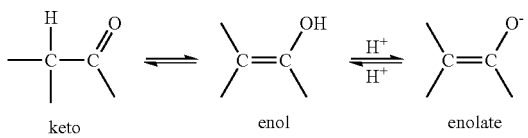

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.*, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer). When a specific isomeric form is identified (e.g. S configuration, or E isomer), this means that said isomeric form is substantially free of the other isomer(s), i.e. said isomeric form is present in at least 55%, 60%, 65%, 70%, 75%, 80%, 85%, 90%, 95%, 99% or more (e.g. substantially all) of the total amount of the compound of the invention.

Hereinbefore or hereinafter, some compounds include the following bond ⦚. This indicates that the compound is a single stereoisomer with unknown configuration or a mixture of stereoisomers.

The compounds of the invention include compounds with one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(═O)OR, wherein R is an ester substituent, for example, a $C_{1-6}$alkyl group, a heterocyclyl group, or a $C_{5-20}$ aryl group, preferably a $C_{1-6}$ alkyl group. Particular examples of ester groups include, but are not limited to, —C(═O)OCH$_3$, —C(═O)OCH$_2$CH$_3$, —C(═O)OC(CH$_3$)$_3$, and —C(═O)OPh. Examples of acyloxy (reverse ester) groups are represented by —OC(═O)R, wherein R is an acyloxy substituent, for example, a $C_{1-7}$alkyl group, a $C_{3-20}$ heterocyclyl group, or a $C_{5-20}$ aryl group, preferably a $C_{1-7}$alkyl group. Particular examples of acyloxy groups include, but are not limited to, —OC(═O)CH$_3$ (acetoxy), —OC(═O)CH$_2$CH$_3$, —OC(═O)C(CH$_3$)$_3$, —OC(═O)Ph, and —OC(═O)CH$_2$Ph.

For example, some prodrugs are esters of the active compound (e.g., a physiologically acceptable metabolically labile ester). By "prodrugs" is meant for example any compound that is converted in vivo into a biologically active compound of the formula (I). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —C(═O)OR wherein R is: $C_{1-6}$alkyl (e.g., -Me, -Et, -nPr, -iPr, -nBu, -sBu, -iBu, -tBu); $C_{1-6}$aminoalkyl [e.g., aminoethyl; 2-(N,N-diethylamino)ethyl; 2-(4-morpholino)ethyl); and acyloxy-$C_{1-7}$alkyl [e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl]. Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in ~50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent.

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis, ocular diseases, arthritis and hemangioma.

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

There is evidence for normalization of glioblastoma blood vessels in patients treated with a pan-VEGF receptor tyrosine kinase inhibitor, AZD2171, in a phase 2 study. MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper-(or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3; or in particular the compounds of formula (I) and sub-groups thereof are inhibitors of FGFR4.

Preferred compounds are compounds that inhibit one or more FGFR selected from FGFR1, FGFR2, FGFR3, and FGFR4. Preferred compounds of the invention are those having $IC_{50}$ values of less than 0.1 µM.

Compounds of the invention also have activity against VEGFR.

In addition many of the compounds of the invention exhibit selectivity for the FGFR 1, 2, and/or 3, and/or 4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or 4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, and/or VEGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

The compound of the invention, having FGFR such as FGFR1 inhibitory activity, may be particularly useful in the treatment or prevention of breast cancer in particular Classic Lobular Carcinomas (CLC).

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4;14) translocation or overexpressing FGFR3), prostate cancer (hormone refractory prostrate carcinomas), endometrial cancer (in particular endometrial tumours with activating mutations in FGFR2) and breast cancer (in particular lobular breast cancer).

In particular the compounds are useful in the treatment of lobular carcinomas such as CLC (Classic lobular carcinoma).

As the compounds have activity against FGFR3 they will be useful in the treatment of multiple myeloma and bladder cancer.

In particular the compounds are useful for the treatment of t(4;14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC, squamous cell carcinoma, liver cancer, kidney cancer, breast cancer, colon cancer, colorectal cancer, prostate cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR or VEGFR signalling may be determined by means of a cell growth assay as set out below or by a method as set out in the section headed "Methods of Diagnosis".

The compounds of the invention, and in particular those compounds having FGFR, or VEGFR inhibitory activity, may be particularly useful in the treatment or prevention of cancers of a type associated with or characterised by the presence of elevated levels of FGFR, or VEGFR, for example the cancers referred to in this context in the introductory section of this application.

The compounds of the present invention may be useful for the treatment of the adult population. The compounds of the present invention may be useful for the treatment of the pediatric population.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR, and VEGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 μM, more preferably less than 0.1 μM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment of FGFR-dependent cancer. In one embodiment, the compound as defined herein is for use in the prophylaxis or treatment of cancer mediated by FGFR kinases. Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

The use of a compound of formula (I) as defined herein for the manufacture of a medicament for the prophylaxis or treatment of a disease state or condition mediated by a FGFR kinase, the compound having the formula (I) as defined herein.

The use of a compound of formula (I) as defined herein for the manufacture of a medicament for the prophylaxis or treatment of a disease state or condition as described herein.

The use of a compound of formula (I) as defined herein for the manufacture of a medicament for the prophylaxis or treatment, in particular the treatment, of cancer.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a compound of the formula (I), a patient may be screened to determine whether a disease or condition from which the patient is or may be suffering is one which would be susceptible to treatment with a compound having activity against FGFR, and/or VEGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, and/or VEGFR or to sensitisation of a pathway to normal FGFR, and/or VEGFR activity, or to upregulation of these growth factor signalling pathways such as growth factor ligand levels or growth factor ligand activity or to upregulation of a biochemical pathway downstream of FGFR, and/or VEGFR activation.

Examples of such abnormalities that result in activation or sensitisation of the FGFR, and/or VEGFR signal include loss of, or inhibition of apoptotic pathways, up-regulation of the receptors or ligands, or presence of mutant variants of the receptors or ligands e.g. PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T6741 of the PDGF receptor has been identified in imatinib-treated patients. In addition, a gene amplification of 8p12-p11.2 was demonstrated in ~50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR or VEGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, and/or VEGFR. The term diagnosis includes screening. By marker we include genetic markers including, for example, the measurement of DNA composition to identify mutations of FGFR, and/or VEGFR. The term marker also includes markers which are characteristic of up regulation of FGFR and/or VEGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, and/or VEGFR may mean that the patient would be particularly suitable for treatment with a FGFR, and/or VEGFR inhibitor. Tumours may preferentially be screened for presence of a FGFR, and/or VEGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), 3$^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105.

Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer.

Therefore in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intra-vaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

- platinum coordination compounds for example cisplatin optionally combined with amifostine, carboplatin or oxaliplatin;
- taxane compounds for example paclitaxel, paclitaxel protein bound particles (Abraxane™) or docetaxel;
- topoisomerase I inhibitors such as camptothecin compounds for example irinotecan, SN-38, topotecan, topotecan hcl;
- topoisomerase II inhibitors such as anti-tumour epipodophyllotoxins or podophyllotoxin derivatives for example etoposide, etoposide phosphate or teniposide;
- anti-tumour vinca alkaloids for example vinblastine, vincristine or vinorelbine;
- anti-tumour nucleoside derivatives for example 5-fluorouracil, leucovorin, gemcitabine, gemcitabine hcl, capecitabine, cladribine, fludarabine, nelarabine;
- alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;
- anti-tumour anthracycline derivatives for example daunorubicin, doxorubicin optionally in combination with dexrazoxane, doxil, idarubicin, mitoxantrone, epirubicin, epirubicin hcl, valrubicin;
- molecules that target the IGF-1 receptor for example picropodophilin;
- tetracarcin derivatives for example tetrocarcin A;
- glucocorticoIden for example prednisone;
- antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, ONTO 328;
- estrogen receptor antagonists or selective estrogen receptor modulators or inhibitors of estrogen synthesis for example tamoxifen, fulvestrant, toremifene, droloxifene, faslodex, raloxifene or letrozole;
- aromatase inhibitors such as exemestane, anastrozole, letrazole, testolactone and vorozole;
- differentiating agents such as retinoids, vitamin D or retinoic acid and retinoic acid metabolism blocking agents (RAMBA) for example accutane;
- DNA methyl transferase inhibitors for example azacytidine or decitabine;
- antifolates for example premetrexed disodium;
- antibiotics for example antinomycin D, bleomycin, mitomycin C, dactinomycin, carminomycin, daunomycin, levamisole, plicamycin, mithramycin;
- antimetabolites for example clofarabine, aminopterin, cytosine arabinoside or methotrexate, azacitidine, cytarabine, floxuridine, pentostatin, thioguanine;
- apoptosis inducing agents and antiangiogenic agents such as Bcl-2 inhibitors for example YC 137, BH 312, ABT 737, gossypol, HA 14-1, TW 37 or decanoic acid;
- tubuline-binding agents for example combrestatin, colchicines or nocodazole;
- kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;
- farnesyltransferase inhibitors for example tipifarnib;
- histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;
- Inhibitors of the ubiquitin-proteasome pathway for example PS-341, MLN 41 or bortezomib;
- Yondelis;
- Telomerase inhibitors for example telomestatin;
- Matrix metalloproteinase inhibitors for example batimastat, marimastat, prinostat or metastat.
- Recombinant interleukins for example aldesleukin, denileukin diftitox, interferon alfa 2a, interferon alfa 2b, peginterferon alfa 2b
- MAPK inhibitors
- Retinoids for example alitretinoin, bexarotene, tretinoin
- Arsenic trioxide
- Asparaginase
- Steroids for example dromostanolone propionate, megestrol acetate, nandrolone (decanoate, phenpropionate), dexamethasone
- Gonadotropin releasing hormone agonists or antagonists for example abarelix, goserelin acetate, histrelin acetate, leuprolide acetate
- Thalidomide, lenalidomide
- Mercaptopurine, mitotane, pamidronate, pegademase, pegaspargase, rasburicase
- BH3 mimetics for example ABT-737
- MEK inhibitors for example PD98059, AZD6244, CI-1040
- colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.
- a steroidal cytochrome P450 17alpha-hydroxylase-17,20-lyase inhibitor (CYP17), e.g. abiraterone, abiraterone acetate.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogoues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same. Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter (mg/m$^2$) of body surface area, for example 50 to 400 mg/m$^2$, particularly for cisplatin in a dosage of about 75 mg/m$^2$ and for carboplatin in about 300 mg/m$^2$ per course of treatment.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m², and for vinorelbine in dosage of about 10 to 30 mg/m² per course of treatment.

The anti-tumour nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}$I, $^{131}$I, $^{3}$H and $^{14}$C. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

General Synthetic Routes

The following examples illustrate the present invention but are examples only and are not intended to limit the scope of the claims in any way.

Hereinafter, the term
'brine' means saturaded aqueous sodium chloride solution
'CH$_3$CN' means acetonitrile, 'CHCl$_3$' means chloroform, 'CO' means carbon monoxide, 'Cs$_2$CO$_3$' means cesium carbonate, 'DCM' means dichloromethane, 'DiPEA' means N,N-diisopropylethylamine, 'DME' means ethylene glycol dimethylether, 'DMF' means N,N-dimethylformamide, 'DMSO' means dimethyl sulfoxide, 'EtOAc' means ethyl acetate, 'EtOH' means ethanol, 'Et$_2$O' means diethyl ether, 'Et$_3$N' means triethylamine, 'HCl' means hydrochloric acid, 'i-PrOH' means 2-propanol, 'KOAc' means potassium acetate, 'K$_2$CO$_3$' means potassium carbonate, 'MeOH' means methanol, 'MgSO$_4$' means magnesium sulphate, 'MP' means melting point 'MnO$_2$' means manganese (IV) oxide, 'NaCl' means sodium chloride, 'NaOH' means sodium hydroxide, 'Na$_2$CO$_3$' means sodium carbonate, 'Na$_2$SO$_4$' means sodium sulfate, 'NaH' means sodium hydride, 'NH$_4$OH' means ammonium hydroxide, 'NH$_4$Cl' means ammonium chloride, 'N$_2$' means nitrogen, 'SiO$_2$' or 'SiOH' means silica, 'THF' means tetrahydrofuran, 'Pd(PPh$_3$)$_4$' means tetrakis(triphenylphosphine)palladium, 'Pd(OAc)$_2$' means palladium(II) acetate (47% Pd), 'PdCl$_2$(dppf).CH$_2$Cl$_2$' means 1,1'-Bis(diphenylphosphino)ferrocene-palladium(II)dichloride dichloromethane complex, 'Pd(3,5,3'5'-OMe-dba)$_2$' means bis(3,5,3',5'-dimethoxydibenzylideneacetone)palladium, 'PPh$_3$O' means triphenylphosphine oxide, 'POCl$_3$' means phosphorus oxychloride, "r.t." means retention time., 'M.P.' means melting point, 'H$_2$' means hydrogen; 'atm' means atmosphere, 'tlc' means thin layer chromatography; 'Pd/C' means palladium on charcoal; 'BINAP' means 2,2'-bis(diphenylphosphino)-1,1'-binaphtalene, 'min' means minute(s).

A. Preparation of the Intermediate Compounds

Example A1 a) Preparation of Intermediate 1

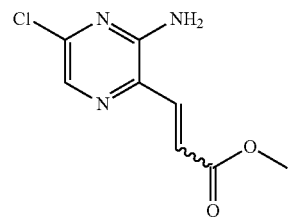

2-Amino-3-bromo-6-chloropyrazine (212779-21-0) (39.78 g; 191 mmol) was diluted in dry dioxane (400 mL) and DiPEA (53.3 mL; 305 mmol). The solution was degassed with N2. Then, tris(dibenzylideneacetone)dipalladium(0) (3.50 g; 3.82 mmol), tri-tert-butyl-phosphonium tetrafluoroborate (2.77 g; 9.54 mmol) and methyl acrylate (34.23 mL; 382 mmol) were added. The mixture was heated at 120° C. for 5 h30. The reaction mixture was cooled down to room temperature, a saturated aqueous solution of NaHCO$_3$ and EtOAc were added, then the mixture was decanted. The organic layer was dried over MgSO$_4$, filtered and concentrated to dryness. The residue was taken up with diisopropylether. The precipitate was filtered off to give 35.67 g (87%, brown solid) of intermediate 1.

b) Preparation of Intermediate 2

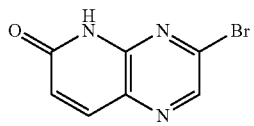

In a round bottom flask, intermediate 1 (35.69 g; 167.07 mmol) was diluted in a solution of bromidic acid in acetic acid 33% (240 mL). The mixture was stirred at 40-50° C. for 2 hours. The reaction mixture was cooled to room temperature and diisopropylether was added. The precipitate was filtered off, washed with diisopropylether and dried under vacuum, yielding 43.59 g (85%, brown solid) of intermediate 2, which was used without further purification in the next step.

c) Preparation of Intermediate 3

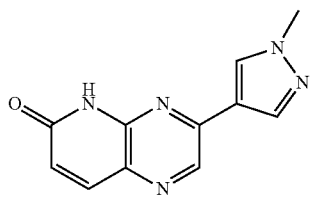 [SMILES: Cn1cc(-c2cnc3ccc(=O)[nH]c3n2)cn1]

Under N$_2$ flow, Pd(PPh$_3$)$_4$ (0.9 g; 0.75 mmol) was added to a mixture of the intermediate 2 (1.7 g; 7.4 mmol), 1-methylpyrazole-4-boronic acid pinacol ester (1.7 g; 8.1 mmol), sodium carbonate (1.6 g; 14.7 mmol) in DME (40 mL) and water (10 mL). The mixture was heated at 100° C. overnight. The solvent was evaporated then the residue was triturated with methyl-tert-butyl ether, filtered and dried to give 1.45 g (87%) of intermediate 3, which was used without further purification in the next step.

d.) Preparation of Intermediate 4

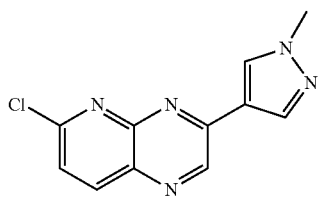 [SMILES: Cn1cc(-c2cnc3ccc(Cl)nc3n2)cn1]

POCl$_3$ (6.4 mL; 68.65 mmol) was added drop wise over a 10 minute period to a suspension of intermediate 3 (3.9 g; 17.16 mmol) and DMF (2.66 mL; 34.33 mmol) in 1,2-dichloroethane (75 mL) at 80° C. The reaction mixture was heated at 80° C. for 3 hours and cooled to room temperature. The reaction mixture was slowly poured onto a 10% aqueous solution of K$_2$CO$_3$ and extracted with DCM/MeOH. The organic layer was decanted, washed with water, dried over MgSO$_4$, filtered and dried to dryness yielding 3.1 g (73%) of intermediate 4.

This intermediate 4 was alternatively also prepared using the following procedure:

A mixture of 6-chloropyridine-2,3-diamine (CAS 40851-95-4) (10 g; 69.65 mmol), 2-bromo-1-(1-methyl-1H-pyrazol-4-yl)ethan-1-one (CAS 706819-66-1) (14.1 g; 69.65 mmol) and DiPEA (24 mL; 139.3 mmol) in CH$_3$CN (280 mL) was heated at 90° C. for 18 hours. The heating was stopped and MnO$_2$ (18.2 g; 208.95 mmol) was added portion wise (carefully) and the reaction mixture was stirred at room temperature for 15 minutes. MnO$_2$ was removed by filtration over a pad of Celite® and the filtrate was concentrated.

The precipitate was filtered, washed with Et$_2$O and dried to give 10.4 g (61%) of intermediate 4.

This intermediate 4 was alternatively also prepared using the following procedure:

a) Preparation of Intermediate 4a

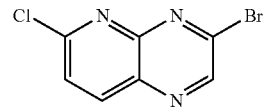 [SMILES: Clc1ccc2ncc(Br)nc2n1]

POCl$_3$ (12 mL; 130.3 mmol) was added drop wise to a suspension of intermediate 2 (10 g; 32.6 mmol) and DMF (5 mL; 65.16 mmol) in 1,2-dichloroethane (300 mL) previously heated at 80° C. The reaction mixture was heated at 80° C. for 3 hours and cooled to room temperature. The reaction mixture was slowly poured onto a saturated aqueous solution of NaHCO$_3$. DCM/MeOH (9/1) was added and the 2 layers were separated. The aqueous layer was extracted with CH$_2$Cl$_2$/MeOH (9/1). The organic layer was decanted, washed with water, dried over MgSO$_4$, filtered and evaporated to dryness to afford 6.36 g (black solid) of intermediate 4a which was directly used in the next step without any further purification.

b) A solution of intermediate 4a (20 g; 81.81 mmol), 1-methylpyrazole-4-boronic acid pinacol ester (13.6 g; 65.45 mmol), Na$_2$CO$_3$ 2M (205 mL) in DME (798 mL) were degassed under N$_2$. Pd(PPh$_3$)$_4$ (4.73 g; 4.09 mmol) was added and the reaction mixture was heated at reflux for 2 hours. The mixture was poured into ice and extracted with EtOAc. The mixture was filtered over Celite®, Celite® was washed with CH$_2$Cl$_2$. The organic layers were dried over MgSO$_4$, filtered and the solvent was evaporated. The residue was taken up with CH$_3$CN, filtered and dried to give 15.32 g (76%) of intermediate 4.

e) Preparation of Intermediate 5

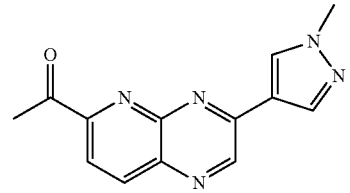 [SMILES: CC(=O)c1ccc2ncc(-c3cnn(C)c3)nc2n1]

A mixture of intermediate 4 (1 g; 4.07 mmol), tributyl(1-ethoxyninyl)tin (1.7 mL; 5.09 mmol) and Pd(PPh$_3$)$_4$ (0.14 g; 0.12 mmol) in toluene (60 mL) was heated at 110° C. for 3 hours. Then, the mixture was cooled to room temperature, an aqueous solution of HCl 2N (60 mL) was added and the reaction mixture was stirred for 1 hour at room temperature. The mixture was poured out into iced water, neutralized with K$_2$CO$_3$ powder. EtOAc was added and the solution was filtered through a pad of Celite®. The filtrate was extracted with EtOAc. The combined organic layers were dried over MgSO$_4$, filtered and the solvent was evaporated. The residue (2.65 g) was purified by chromatography over silica gel (15-40 μm, 50 g: mobile phase: 98% DCM, 2% MeOH, 0.1% NH$_4$OH). The fractions containing the product were collected and evaporated. The residue (0.6 g) was purified by chromatography over silica gel (irregular 15-40 μm 30 g; mobile phase: gradient from 0.1% NH$_4$OH, 99% DCM, 1% iPrOH to 0.1% NH$_4$OH, 97% DCM, 3% iPrOH). The pure fractions were collected and the solvent was evaporated to give 164 mg of intermediate 4, 28 mg of mixture and 105 mg (10%) of intermediate 5.

$^1$H NMR (500 MHz, DMSO-d$_6$) δ 9.51 (s, 1H), 8.81 (s, 1H), 8.62 (d, J=8.51 Hz, 1H), 8.42 (s, 1H), 8.23 (d, J=8.51 Hz, 1H), 3.98 (s, 3H), 2.80 (s, 3H);

MS (ESI$^+$) m/z (%) (r.t. 1.96) 254 (100) [M+H]$^+$ method A1

M.P.: 202° C. (Kofler).

Example A2

Preparation of Intermediate 6

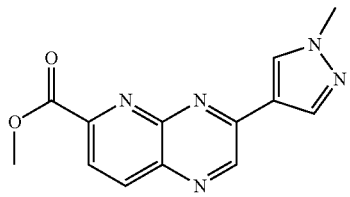 [SMILES: COC(=O)c1ccc2ncc(-c3cnn(C)c3)nc2n1]

The reaction was performed on 2 batches of intermediate 4 (3 g; 12.21 mmol) and (2 g; 8.14 mmol):

Intermediate 4 (3 g; 12.21 mmol), Pd(OAc)$_2$ (0.58 g; 1.22 mmol), 1,3-bis(diphenylphosphino)propane (0.51 g; 1.22 mmol), KOAc (2.40 g; 24.42 mmol), and MeOH (150 mL) were heated in an autoclave at 120° C. under an atmosphere of CO-gas (5 bars) for 3 hours. The reaction mixture was cooled to room temperature, poured onto iced water and a saturated solution of NaCl. DCM was added and the mixture was filtered through a pad of Celite®. The filtrate was extracted with DCM (twice). The organic layer was dried over MgSO$_4$, filtered and evaporated to dryness. The residue was crystallized from Et$_2$O.

The reaction was also performed with 2 g (8.14 mmol) of intermediate 4.

The 2 batches obtained were combined for the purification. The resulting residue (6 g+1.2 g) was purified by chromatography over silica gel (Irregular SiOH 20-45 μm 450 g, mobile phase: 0.1% NH$_4$OH, 97% DCM, 3% MeOH). The pure fractions were collected and the solvent was evaporated to give 2.6 g (68% overall yield) of intermediate 6.

$^1$H NMR (400 MHz, DMSO-d$_6$) δ 9.50 (s, 1H), 8.76 (s, 1H), 8.64 (d, J=8.59 Hz, 1H), 8.39 (s, 1H), 8.30 (d, J=8.59 Hz, 1H), 3.94-4.00 (m, 6H);

MS (ESI$^+$) m/z (%) (r.t. 1.81) 270 (100) [M+H]$^+$ method A1

M.P.: 224° C. (Kofler).

Example A3 a) Preparation of Intermediate 7

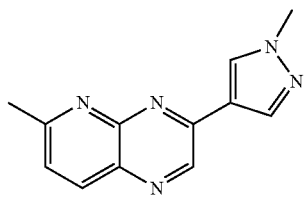

A mixture of intermediate 4 (5 g; 20.35 mmol), tri-n-butylmethyltin (11.4 mL; 40.71 mmol) and Pd(PPh$_3$)$_4$ (1.18 g; 1.02 mmol) in DMF (200 mL) was heated at 80° C. overnight. Then, additional, tri-n-butylmethyltin (5.7 mL; 20.36 mmol) and Pd(PPh$_3$)$_4$ (0.59 g; 0.51 mmol) were added and the solution was heated for 48 hours. The mixture was cooled, poured onto iced water and EtOAc was added. The mixture was filtered through a pad of Celite® and the filtrate was extracted with EtOAc. The organic layers were dried over MgSO$_4$, filtered and the solvent was evaporated. Et$_2$O was added to the residue (19 g). The precipitate was filtered (PPh$_3$O) and the filtrate was evaporated. The residue (13 g) was purified by flash chromatography over silica gel (15-40 μm, 80 g: 98% DCM, 2% MeOH, 0.1% NH$_4$OH). The pure fractions were collected and the solvent was evaporated to give 3 g (65%) of intermediate 7.

Intermediate 7 was alternatively also prepared using the following procedure: A mixture of 6-methylpyridine-2,3-diamine (CAS 33259-72-2) (804 mg; 6.53 mmol), 2-bromo-1-(1-methyl-1H-pyrazol-4-yl)-ethanone (CAS 706819-66-1) (1.32 g; 6.53 mmol) and DiPEA (2.3 mL; 13.06 mmol) in CH$_3$CN (25 mL) was heated at 90° C. for 18 hours. The reaction mixture was cooled to room temperature, diluted with DCM and water. The organic layer was decanted, dried over MgSO$_4$, filtered and evaporated to dryness. The residue (1.55 g) was purified by chromatography over silica gel (irregular SiOH 15-40 μm, 300 g, mobile phase: 0.4% NH$_4$OH, 96% DCM, 4% iPrOH). The pure fractions were collected and evaporated to dryness yielding 820 mg (56%) of intermediate 7.

$^1$H NMR (500 MHz, DMSO-d$_6$) δ 9.09 (s, 1H), 8.43 (s, 1H), 7.92-8.22 (m, 2H), 7.42 (d, J=8.20 Hz, 1H), 3.74 (s, 3H), 2.50 (s, 3H);

MS (ESI$^+$) m/z (%) (r.t. 1.68) 226 (100) [M+H]$^+$; method A1

M.P.: 179° C., Kofler.

b) Preparation of Intermediate 8

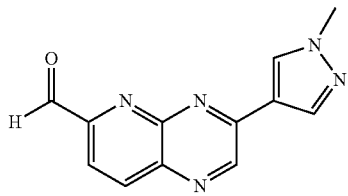 [SMILES: Cn1cc(-c2cnc3ccc(C=O)nc3n2)cn1]

A mixture of intermediate 7 (0.42 g; 1.87 mmol) and selenium dioxide (0.2 g; 1.87 mmol) in dioxane (30 mL) was heated at 80° C. for 2 hours. The solution was cooled to room temperature and DCM was added. The organic layer was filtered through a pad of Celite®. The filtrate was evaporated to give 440 mg (99%) of intermediate 8.

$^1$H NMR (500 MHz, DMSO-d$_6$) δ 10.16 (s, 1H), 9.53 (s, 1H), 8.78 (s, 1H), 8.67 (d, J=8.20 Hz, 1H), 8.41 (s, 1H), 8.18 (d, J=8.20 Hz, 1H), 3.98 (s, 3H);

MS (ESI$^+$) m/z (%) (tr 2.55) 240 (100) [M+H]$^+$ method B1.

c) Preparation of Intermediate 18

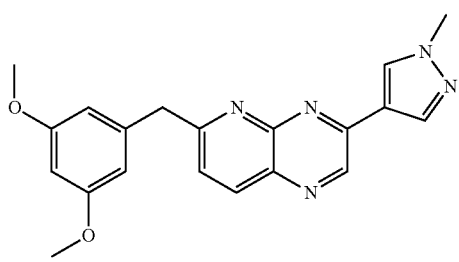 [SMILES: COc1cc(Cc2ccc3ncc(-c4cnn(C)c4)nc3n2)cc(OC)c1]

A mixture of intermediate 7 (366 mg; 1.63 mmol), 1-bromo-3,5-dimethoxybenzene (0.35 g; 1.63 mmol), Cs$_2$CO$_3$ (1.06 g; 3.25 mmol), Pd(3,5,3'5'-OMe-dba)$_2$ (0.13 g; 0.16 mmol) and 9,9-dimethyl-4,5-bis(diphenylphosphino)xanthene (94 mg; 0.16 mmol) in dioxane (29 mL) was heated at 100° C. for 4 hours. The solution was cooled and the mixture was poured onto cooled water. The mixture was extracted with DCM. The organic layer was dried over MgSO$_4$, filtered and evaporated to dryness. The residue (1.1 g) was purified by chromatography over silica gel (15-40 μm, 50 g; mobile phase: 99% DCM, 1% MeOH, 0.1% NH$_4$OH). The pure fractions were collected and the solvent was evaporated. The residue (574 mg) was purified by column chromatography over silica gel (Silica 5 μm 150× 30.0 mm; mobile phase: gradient from 0.2% NH$_4$OH, 98% DCM, 2% MeOH to 1% NH$_4$OH, 90% DCM, 10% MeOH). The pure fractions were collected and the solvent was evaporated to give 181 mg (31%) of intermediate 18.

$^1$H NMR (400 MHz, DMSO-d$_6$) δ 9.33 (s, 1H), 8.69 (s, 1H), 8.36 (d, J=8.59 Hz, 1H), 8.33 (s, 1H), 7.67 (d, J=8.59 Hz, 1H), 6.53 (d, J=2.02 Hz, 2H), 6.37 (t, J=2.02 Hz, 1H), 4.25 (s, 2H), 3.96 (s, 3H), 3.70 (s, 6H);

MS (ESI$^+$) m/z (%) (r.t. 1.51) 362 (100) [M+H]$^+$, 723 (25) [2M+H]$^+$ method A1.

Example A4

Preparation of Intermediate 9

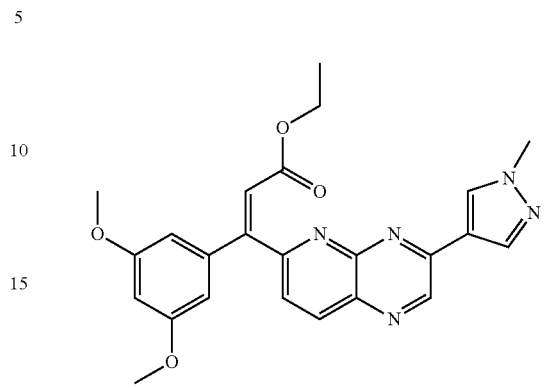

Triethyl phosphonoacetate (0.92 mL; 4.64 mmol) was added drop wise to a suspension of NaH (0.232 g; 5.79 mmol) in DMF (100 mL) at 0° C. and under N2. After 30 minutes, compound 1 (1.45 g; 3.86 mmol) was added at 0° C. and the mixture was stirred at room temperature for 2 hours. The mixture was treated with a saturated solution of NaCl and extracted with EtOAc. The organic layer was separated, dried over MgSO$_4$, filtered and the solvents were evaporated. The residue (2.3 g) was purified by column chromatography over silica gel (15-40 μm: 50 g; mobile phase: 98% DCM, 2% MeOH). The fractions containing the product were collected and the solvent was evaporated to give 2 fractions of intermediate 9: 940 mg (55%,) and 490 mg (29%,).

$^1$H NMR (500 MHz, DMSO-d$_6$) δ 9.43 (s, 1H), 8.70 (s, 1H), 8.47 (d, J=8.51 Hz, 1H), 8.34 (s, 1H), 7.65 (d, J=8.51 Hz, 1H), 6.76 (s, 1H), 6.59 (s, 1H), 6.49 (d, J=1.89 Hz, 2H), 3.97 (s, 3H), 3.92 (q, J=7.09 Hz, 2H), 3.72 (s, 6H), 0.94 (t, J=7.09 Hz, 3H);

MS (ESI$^+$) m/z (%) (r.t. 1.60) 446 (100) [M+H]$^+$, 892 (75) [2M+H]+ method C1.

Example A5

Preparation of Intermediate 10 and 11

Intermediate 10

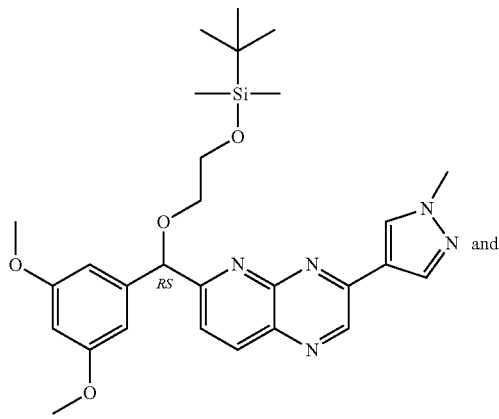

and

-continued intermediate 11

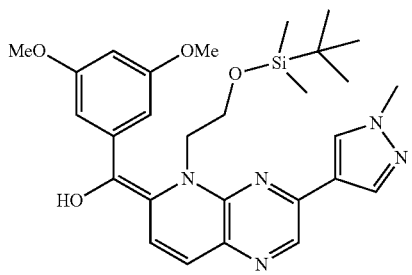

NaH (70 mg; 1.75 mmol) was added at room temperature to a solution of compound 2 (0.22 g; 0.58 mmol) in DMF (4 mL) under N2 flow. The mixture was stirred for 30 minutes. (2-bromoethoxy)-tert-butyldimethylsilane (0.25 mL; 1.17 mmol) was added. The mixture was stirred at room temperature for 2 days. The solution was poured onto cooled water and the product was extracted with EtOAc. The organic layer was washed with water and dried over MgSO$_4$, filtered and evaporated to dryness yielding 315 mg of a mixture of intermediate 10 and intermediate 11, which was used without any further purification in the next step.

Example A6 a) Preparation of Intermediate 12

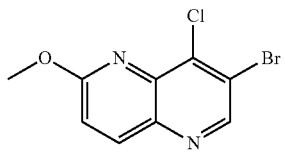

POCl$_3$ (213 mL; 2.28 mol) was added to a mixture of 3-bromo-6-methoxy-1,5-naphthyridin-4-ol (1075259-68-5) (58.2 g; 228 mmol) in CHCl$_3$ (213 mL). The solution was refluxed for 3 hours, concentrated till dryness and dried under vacuum. The residual solid was carefully basified with an aqueous solution of NaOH 1M (300 mL), diluted with water (300 mL) and extracted with EtOAc (6×500 mL). The combined organic layers were dried over Na$_2$SO$_4$, filtered and concentrated, yielding 54.0 g (87%) of intermediate 12, which was used without further purification for the next step.

b) Preparation of Intermediate 13

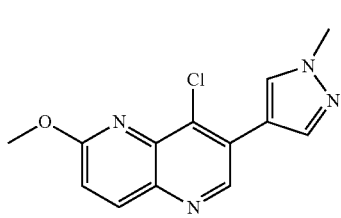 [SMILES: COc1ccc2ncc(-c3cnn(C)c3)c(Cl)c2n1]

A solution of intermediate 12 (31.4 g; 115 mmol), 1-methylpyrazole-4-boronic acid pinacol ester (25.1 g; 121 mmol), sodium carbonate (36.5 g; 344 mmol) in a mixture of 1,4-dioxane (400 mL) and water (120 mL) was degassed and filled with argon (operation repeated 3 times). PdCl$_2$(dppf).CH$_2$Cl$_2$ (4.68 g; 5.74 mmol) was added and the resulting mixture was degassed and filled with argon (operation repeated twice) and stirred at 110° C. for 16 hours. After cooling to room temperature, EtOAc (500 mL) and water (500 mL) were added to the reaction mixture. The layers were separated and the aqueous layer was extracted with EtOAc (2×400 mL). The combined organic layers were dried over Na$_2$SO$_4$, filtered and evaporated to dryness. The residue was sonicated in Et$_2$O (500 mL), filtered on glass-frit, washed with Et$_2$O (2×200 mL) and dried under vacuum, yielding 29.2 g (93%) of intermediate 13.

c) Preparation of Intermediate 14

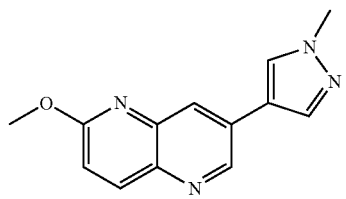 [SMILES: COc1ccc2ncc(-c3cnn(C)c3)cc2n1]

A catalytic amount of Raney Nickel (50% slurry in water, 1.68 g; 28.6 mmol) was washed twice with EtOH and collected after decantation. This catalytic amount was added to a solution of intermediate 13 (26.2 g; 95.4 mmol) in a mixture of EtOH (700 mL), THF (500 mL) and 1M in NaOH (114 mL; 114 mmol). The mixture was purged and stirred under hydrogen atmosphere (1 bar) at 50° C. for 16 hours. An additional amount of Raney Nickel (50% slurry in water, 1.68 g; 28.6 mmol) was added and the reaction mixture was purged and stirred under hydrogen atmosphere (1 bar) at 50° C. for 24 hours. The mixture was cooled to room temperature, filtered through a pad of Celite®, washed with THF (500 mL) and concentrated. The residue was triturated in Et$_2$O (500 mL), the precipitate was filtered off and washed with Et$_2$O (100 mL). The obtained product was adsorbed on silica gel and purified by chromatography over silica gel (mobile phase; gradient from 96% DCM, 4% MeOH to 94% DCM, 6% MeOH). The product fractions were collected and the solvent was evaporated, yielding 9.05 g (39%) of intermediate 14.

d) Preparation of Intermediate 15

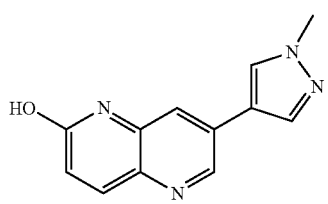 [SMILES: Cn1cc(-c2cnc3ccc(O)nc3c2)cn1]

6M aqueous HCl (94 mL; 564 mmol) was added to a solution of intermediate 14 (9.0 g; 37.6 mmol) in 1,4-dioxane (200 mL). The mixture was stirred at 80° C. for 3 hours, cooled down to room temperature and concentrated. The residue was suspended in a mixture of water, DCM/MeOH (300 mL; 3/2/1). The mixture was basified with a 3N aqueous solution of NaOH until pH=9 and the resulting solution was concentrated, yielding 13.7 g (quantitative) of intermediate 15, which was used without further purification for the next step.

e) Preparation of Intermediate 16

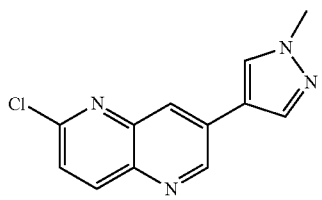 [SMILES: Cn1cc(-c2cnc3ccc(Cl)nc3c2)cn1]

The reaction was performed under argon.

POCl₃ (200 mL; 2.15 mol) was added to a suspension of intermediate 15 (13.7 g; 37.6 mmol) in CHCl₃ (200 mL). The reaction mixture was refluxed for 16 hours, cooled to room temperature and concentrated. The residual solid was taken up in a mixture of DCM/MeOH 95/5 (300 mL), slowly basified at 0° C. with an aqueous solution of sodium hydroxide 3M (60 mL) and diluted with water (100 mL). The aqueous layer was extracted with a mixture of DCM/MeOH 95/5 (2×150 mL). The combined organic layers were dried over Na₂SO₄, filtered and concentrated. The obtained residue was dissolved in a mixture of DCM/MeOH 3/1 (400 mL), adsorbed on silica gel and purified by column chromatography over silica gel (mobile phase; gradient from 97% DCM, 3% MeOH to 95% DCM, 5% MeOH). The product fractions were collected and the solvent was evaporated, yielding 6.15 g (67%) of intermediate 16, which was used without further purification for the next step.

f) Preparation of Intermediate 17

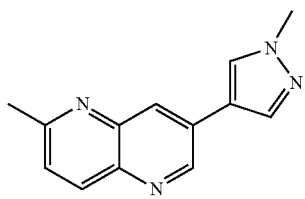 [SMILES: Cc1ccc2ncc(-c3cnn(C)c3)cc2n1]

The reaction was performed from 2 batches of intermediate 16 (500 mg; 2.04 mmol) and (30 mg; 0.12 mmol):

PdCl₂(dppf).CH₂Cl₂ (0.167 g; 0.20 mmol) was added to a mixture of intermediate 16 (0.500 g; 2.04 mmol), trimethylboroxine (0.343 mL; 2.45 mmol) and K₂CO₃ (0.846 g; 6.12 mmol) in dioxane (8 mL) and water (0.8 mL). The reaction mixture was heated at 105° C. overnight. The mixture was cooled to room temperature and the other batch coming from 30 mg of intermediate 16 was added. The mixture was filtered through a pad of Celite®, washed with EtOAc and concentrated. The residue (640 mg, brown solid) was purified by column chromatography over silica gel (eluent: DCM/MeOH 99/1 to 96/4). The product fractions were collected and the solvent was evaporated. The resulting solid was triturated in Et₂O, filtered off and dried under vacuum to give 290 mg (59%, off-white solid) of intermediate 17, M.P.: 149° C. (DSC).

Example A7

Preparation of Intermediate 19

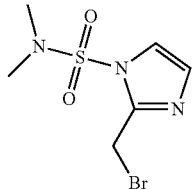

Under N2, Et₃N (1.4 mL; 9.7 mmol) was added to a solution of 2-(hydroxymethyl)-N,N-dimethyl-1H-Imidazole-1-sulfonamide (CAS 935862-80-9) (1 g; 4.87 mmol) in THF (25 mL). The reaction mixture was cooled down to 5° C. and methanesulfonyl chloride (0.45 mL; 5.85 mmol) followed by lithium bromide (1.27 g; 14.62 mmol) were added. The reaction mixture was stirred at room temperature for 2 hour. The reaction mixture was poured into ice water and extracted with EtOAc. The organic layer was washed with brine, dried over MgSO₄, filtered and concentrated under reduced pressure. The residue (1.43 g) was purified by chromatography over silica gel (15-40 µm, 24 g; mobile phase: 99% CH₂Cl₂, 1% CH₃OH). The pure fractions were collected and evaporated to give 0.92 g (70%) intermediate 19. ¹H NMR (400 MHz, DMSO-d₆) δ 7.66 (s, 1H), 7.15 (s, 1H), 4.82 (s, 2H), 2.91 (s, 6H).

Example A8

Preparation of Intermediate 20

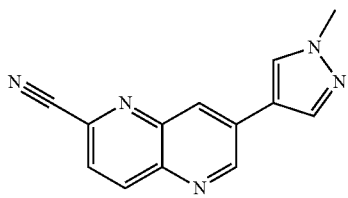 [SMILES: Cn1cc(-c2cnc3ccc(C#N)nc3c2)cn1]

The reaction was performed on 2 batches of intermediate 16 (1 g; 4.09 mmol) and (50 mg; 0.20 mmol):

Pd(PPh₃)₄ (0.473 g; 0.41 mmol) was added to a mixture of intermediate 16 (1 g; 4.09 mmol) and zinc cyanide (0.480 g; 4.09 mmol) in DMF (14 mL) and the mixture was heated to 100° C. for 1.5 hour. The other batch from intermediate 16 (50 mg) was combined with the reaction mixture for the work-up. The mixture was filtered through a pad of Celite® and rinsed with EtOAc (400 mL). The filtrate was washed with a mixture of water (200 mL) and brine (200 mL). The aqueous layer was extracted with EtOAc (2×150 mL). The combined organic layers were dried over Na₂SO₄, filtered and concentrated. The residue (2.29 g, brown oil) was triturated in Et₂O (4×50 mL). The precipitate was filtered and dried under vacuum. The resulting residue (0.272 g, brown solid) was purified by column chromatography over silica gel (eluent: from DCM/MeOH 99/1 to 97/3). The product fractions were collected and the solvent was evaporated to give 2 fractions of intermediate 20: 226 mg (23%, yellow solid) M.P.: 260° C. (DSC).

Example A9 a) Preparation of Intermediate 21

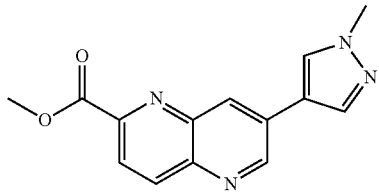 [SMILES: COC(=O)c1ccc2ncc(-c3cnn(C)c3)cc2n1]

The reaction was performed from 2 batches of intermediate 16 (1 g; 4.09 mmol) and (100 mg; 0.41 mmol):

A mixture of intermediate 16 (1 g; 4.09 mmol), Et$_3$N (2.85 mL; 20.5 mmol) and PdCl$_2$(dppf).CH$_2$Cl$_2$ (0.334 g; 0.41 mmol) in MeOH (40 mL) was purged with CO (gas) (three times) and the mixture was heated to reflux under CO atmosphere (1 bar) overnight. Et$_3$N (2.85 mL; 20.5 mmol) and PdCl$_2$(dppf).CH$_2$Cl$_2$ (0.334 g; 0.41 mmol) were added. The mixture was purged with CO (gas) (three times). The mixture was heated to reflux under CO atmosphere (1 bar) overnight. The other batch (from 100 mg) was combined with the reaction mixture for the work-up. Water (400 mL) was added and the mixture was extracted with EtOAc (3×300 mL). The combined organic layers were dried over Na$_2$SO$_4$, filtered and concentrated. The residue (3.2 g, brown solid) was purified by chromatography over silica gel (15-40 μm; mobile phase: from 99% EtOAc, 1% MeOH to 97% EtOAc, 3% MeOH). The pure fractions were collected and the solvent was evaporated to give 600 mg (pale brown solid) of 6-methoxy-3-(1-methyl-pyrazolyl)-1,5-naphthyridine and 587 mg (pale brown solid) of an intermediate fraction of intermediate 21 which was dissolved in DCM (10 mL). Et$_2$O (100 mL) was added and the resulting solid obtained after sonication was filtered off, washed with Et$_2$O (10 mL) and dried under vacuum at 80° C. for 3 hours to give 500 mg (overall yield 41%, beige solid) of intermediate 21, M.P.: 194° C. (DSC).

b) Preparation of Intermediate 22

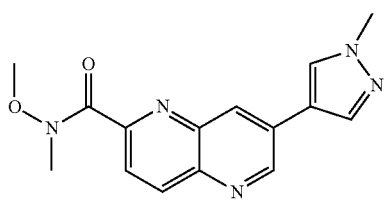 [SMILES: CON(C)C(=O)c1ccc2ncc(-c3cnn(C)c3)cc2n1]

Trimethylaluminium solution 2M in heptane (0.452 mL; 0.90 mmol) was added drop wise to a suspension of N,O-dimethylhydroxylamine hydrochloride (0.166 g; 1.70 mmol) in THF (1.9 mL). The solution was stirred at 0° C. until gas evolution ceased and at room temperature for 30 minutes. This solution was added drop wise to a suspension of intermediate 21 (0.302 g; 1.13 mmol) in THF (4.8 mL) at 0° C. The mixture was stirred at 0° C. for 15 minutes and at room temperature for 5 hours. As the conversion was not complete, trimethylaluminium solution 2M in heptane (0.452 mL; 0.90 mmol) was added drop wise to a suspension of N,O-dimethylhydroxylamine hydrochloride (0.166 g; 1.70 mmol) in THF (1.9 mL). The solution was stirred at 0° C. until gas evolution ceased and at room temperature for 30 minutes. This solution was added drop wise to the reaction mixture at 0° C. The mixture was stirred at 0° C. for 15 minutes and at room temperature overnight. The mixture was cooled to 0° C., brine (100 mL), then a saturated solution of Na$_2$CO$_3$ (10 mL) were slowly added (pH=12). The mixture was extracted with EtOAc (3×50 mL), filtered, concentrated and co-evaporated with Et$_2$O to give 0.322 g (96%, off white solid) of intermediate 22.

Example A10 a) Preparation of Intermediate 23, 23a, 23b

Intermediate 23a

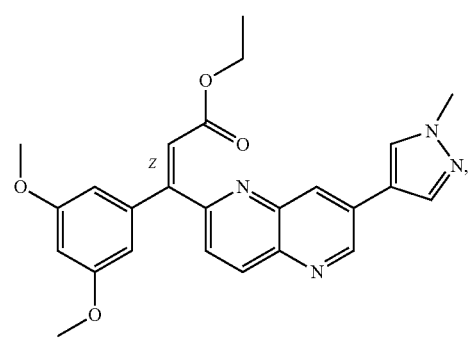

intermediate 23b

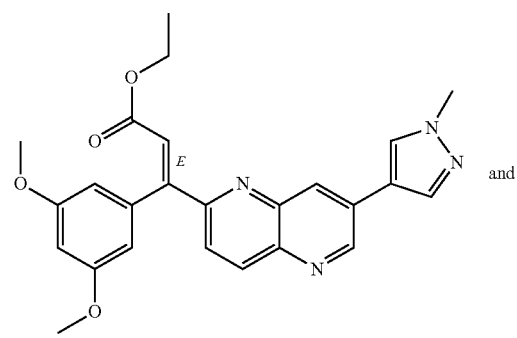

and intermediate 23

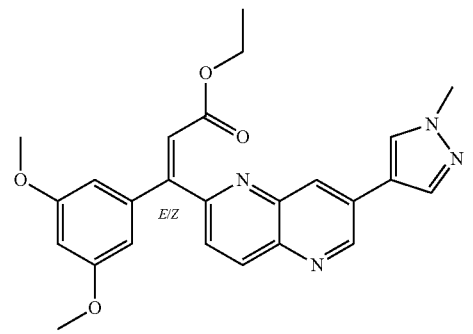

Triethyl phosphonoacetate (0.607 mL; 3.06 mmol) was added at 0° C. to a suspension of NaH (0.122 g; 3.06 mmol) in THF (4 mL). The reaction mixture was stirred at 0° C. for 2 hours and at room temperature for 1 hour. Then, a solution of compound 8 (0.382 g; 1.02 mmol) in THF (12 mL) was added drop wise at 0° C. The reaction mixture was stirred at 0° C. for 30 minutes, then reflux for 2 hours. Water (150 mL) was added and the mixture was extracted with DCM (3×80 mL). The combined organic layers were dried over Na₂SO₄, filtered and concentrated. The residue (0.800 g, brown solid) was purified by chromatography over silica gel (15-40 μm, mobile phase: gradient from 99% DCM, 1% MeOH to 97% DCM, 3% MeOH). The pure fractions were collected and the solvent was evaporated. Each fraction was triturated with Et₂O and dried under vacuum to give: 56 mg (12%, white solid) of intermediate 23b;

¹H NMR (400 MHz, CDCl₃): δ 9.13 (s, 1H), 8.44 (s, 1H), 8.25 (d, J=9.0 Hz, 1H), 7.99 (s, 1H), 7.87 (s, 1H), 7.38 (d, J=9.0 Hz, 1H), 7.29 (s, 1H), 6.54 (s, 1H), 6.46 (s, 2H), 4.13 (q, J=7.0 Hz, 2H), 4.04 (s, 3H), 3.80 (s, 6H), 1.17 (t, J=7.0 Hz, 3H);

MS (ESI⁺) m/z (%) (r.t. 13.05) 445 [M+H]⁺ method D1.

M.P.: 134° C. (DSC).

101 mg (white foam) of a Z/E mixture, intermediate 23.

222 mg (49%, yellow foam) of intermediate 23a;

¹H NMR (400 MHz, CDCl₃): δ 9.12 (s, 1H), 8.40 (s, 1H), 8.36 (d, J=8.4 Hz, 1H), 7.92 (s, 1H), 7.80 (s, 1H), 7.51 (d, J=8.4 Hz, 1H), 6.57 (s, 1H), 6.46 (s, 3H), 3.96-4.03 (m, 5H), 3.72 (s, 6H), 1.02 (t, J=7.0 Hz, 3H);

MS (ESI⁺) m/z (%) (r.t. 12.34) 445 [M+H]⁺ method D1.

M.P.: 139-141° C. (Büchi M-560, 1° C./min).

Example A11

Preparation of Intermediate 24

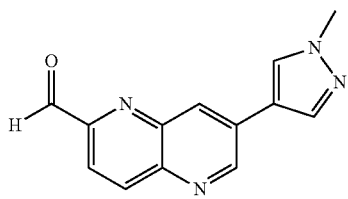

The reaction was performed from 2 batches of intermediate 17 (230 mg; 1.03 mmol) and (30 mg; 0.13 mmol):

A suspension of selenium oxide (0.149 g; 1.34 mmol) in dioxane (5 mL) was heated at 60° C. and intermediate 17 (0.230 g; 1.03 mmol) was added. The mixture was heated at 80° C. for 2 hours. The other batch (from 30 mg) was combined with the reaction mixture for the work-up. The mixture was filtered through a pad of Celite®, washed with dioxane (200 mL) and concentrated. The residue (0.295 g) was purified by chromatography over silica gel (mobile phase: 100% EtOAc). The pure fractions were collected and the solvent was evaporated to give 0.167 g (60%, yellow solid) of intermediate 24, M.P.: 206° C. (DSC).

Example A12

Preparation of Intermediate 25a and 25b

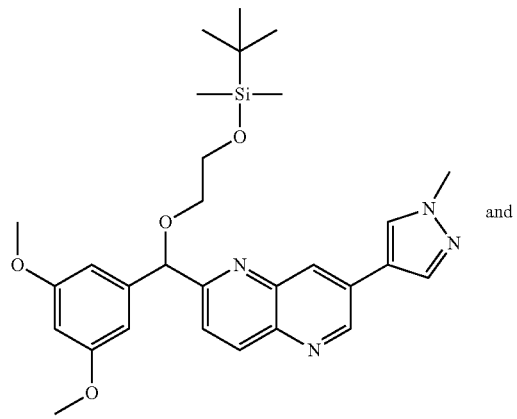

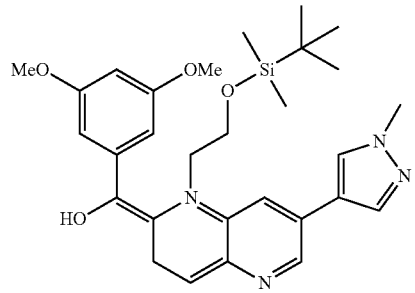

NaH (0.043 g; 1.08 mmol) was added to a suspension of compound 10 (0.270 g; 0.72 mmol) in DMF (5.5 mL) at 0° C. The mixture was stirred at 0° C. for 40 minutes, then 2-(bromoethoxy)-tert-butyl-dimethylsilane (CAS 86864-60-0) (0.23 mL; 1.08 mmol) was added at 0° C. The mixture was stirred at 0° C. for 1 hour and at room temperature for 120 hours. Water (100 mL) and brine (50 mL) were added and the mixture was extracted with EtOAc (3×70 mL). The combined organic layers were dried over Na₂SO₄, filtered and concentrated to give 0.910 g (yellow oil) of a mixture 6/4 of intermediate 25a and intermediate 25b. This fraction was used without purification for the next step.

Example A13

Preparation of Intermediate 25b

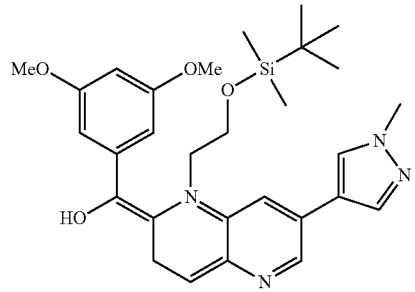

Potassium bis(trimethylsilyl)amide 1M in THF (0.12 mL; 0.12 mmol) was added to a suspension of compound 10 (0.030 g; 0.08 mmol) in THF (0.6 mL) at 0° C. The mixture was stirred at 0° C. for 1 hour, then 2-(bromoethoxy)-tert-butyl-dimethylsilane (CAS 86864-60-0) (0.026 mL; 0.12 mmol) was added at 0° C. The mixture was stirred at 0° C. for 1 hour and at room temperature overnight. Brine (50 mL) was added and the mixture was extracted with EtOAc(3×25 mL). The combined organic layers were dried over Na$_2$SO$_4$, filtered and concentrated to give 0.082 g of intermediate 25b.

Example A14 a) Preparation of Intermediate 26

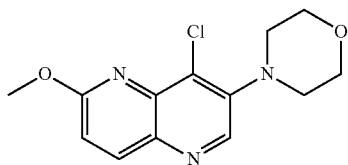 [SMILES: COc1ccc2ncc(N3CCOCC3)c(Cl)c2n1]

The reaction was performed on 2 batches of intermediate 12 (3 g; 11.0 mmol, and 100 mg; 0.366 mmol):

Under an argon atmosphere; cesium carbonate (10.8 g; 33 mmol) and BINAP (1.37 g; 2.20 mmol) were added to a solution of intermediate 12 (3 g; 11.0 mmol) in toluene (90 mL). The mixture was purged 3 times with argon and Pd(OAc)$_2$ (0.247 g; 1.1 mmol) was added. The mixture was purged again 3 times with argon, and morpholine (1.05 ml; 12.1 mmol) was added. The reaction mixture was heated at 100° C. for 16 hours and cooled down to room temperature. The other batch coming from intermediate 12 (100 mg) was combined and the resulting mixture was concentrated to dryness.

The resulting residue was purified by column chromatography over silica gel (eluent: gradient from 99% DCM, 1% MeOH to 98% DCM, 2% MeOH). The fractions containing the product were collected and the solvent was evaporated affording 3.5 g of a yellow solid which was purified again by column chromatography over silica gel (eluent: gradient from 50% cyclohexane, 50% EtOAc to 0% cyclohexane, 100% EtOAc). The fractions containing the product were collected and the solvent was evaporated affording 3.04 g (99%; yellow solid) of intermediate 26, M.P.: 161° C. (DSC).

b) Preparation of Intermediate 27

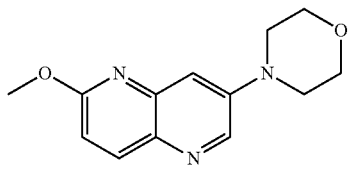 [SMILES: COc1ccc2ncc(N3CCOCC3)cc2n1]

The reaction was performed on 2 batches of intermediate 26 (1.6 g; 5.72 mmol, and 500 mg; 1.79 mmol):

Under an argon atmosphere, PdCl$_2$(dppf).CH$_2$Cl$_2$ (187 mg; 0.23 mmol) was added to a solution of intermediate 26 (1.6 g, 5.72 mmol), 1,2-bis(dimethylamino)ethane (1.46 mL; 9.72 mmol) and sodium borohydride (0.368 g; 9.72 mmol) in THF (55 mL). The resulting mixture was heated at 50° C. for 72 hours. Subsequently, 3 Å molecular sieves (about 100 mg) and additional 1,2-bis(dimethylamino)ethane (2.58 mL; 17.2 mmol), sodium borohydride (0.651 g; 17.2 mmol) and PdCl$_2$(dppf).CH$_2$Cl$_2$ (280 mg; 0.343 mmol) were added and the mixture was heating at 50° C. for 16 more hours.

Then, the other batch coming from intermediate 26 (500 mg) was combined and a saturated aqueous solution of NaCl (400 mL) was added. The aqueous layer was extracted with a 95/5 mixture of EtOAc/MeOH (3×200 mL). The combined organic layers were dried over Na$_2$SO$_4$, filtered and concentrated.

The resulting residue (3.16 g; brown solid) was purified by column chromatography over silica gel (eluent: gradient from 100% DCM, 0% MeOH to 98% DCM, 2% MeOH). The fractions containing the product were collected and the solvent was evaporated affording 1.33 g (72%) of intermediate 27, M.P.: 169° C. (DSC).

c) Preparation of Intermediate 28

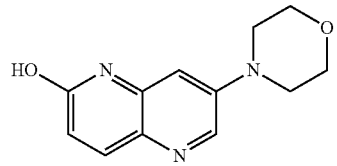 [SMILES: Oc1ccc2ncc(N3CCOCC3)cc2n1]

6 M aqueous HCl (17.7 mL; 106 mmol) was added to a solution of intermediate 27 (1.3 g; 5.30 mmol) in dioxane (26 mL). The resulting mixture was stirred at 80° C. for 16 hours, and was then cooled down to room temperature and concentrated. The residue was suspended in a mixture of water, DCM and MeOH (3/2/1; 100 mL). The resulting mixture was basified with 3 N NaOH (50 mL) until pH 12. The mixture was then adsorbed on silica gel and purified by column chromatography over silica gel (eluent: 85% DCM, 15% MeOH). The fractions containing the product were collected and the solvent was evaporated affording 1.22 g (99%) of intermediate 28.

d) Preparation of Intermediate 29

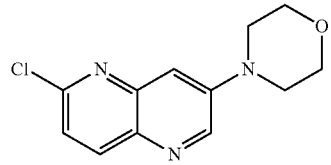 [SMILES: Clc1ccc2ncc(N3CCOCC3)cc2n1]

Under an argon atmosphere, POCl$_3$ (39.3 mL; 422 mmol) was added to intermediate 28 (1.22 g; 5.28 mmol) at 0° C. The reaction mixture was then refluxed for 16 hours and the solvent was concentrated. The resulting residue was dissolved in a mixture of DCM/MeOH (9/1; 100 mL) and the solution was slowly basified at 0° C. with 3 M NaOH (100 mL). Water (200 mL) was added and the layers were separated. The aqueous layer was extracted with a mixture of DCM/MeOH (9/1; 3×100 mL). The combined organic layers were dried over Na$_2$SO$_4$, filtered and concentrated.

The residue (1.5 g; black solid) was purified by column chromatography over silica gel (eluent: 99% DCM, 1% MeOH). The fractions containing the product were collected and the solvent was evaporated affording 1.19 g (90%) of intermediate 29.

e) Preparation of Intermediate 30

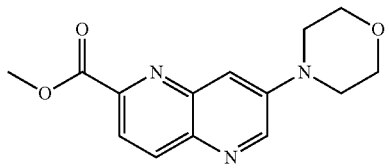 [SMILES: COC(=O)c1ccc2ncc(N3CCOCC3)cc2n1]

The reaction was performed on 2 batches of intermediate 29 (1.19 g; 4.77 mmol, and 176 mg; 0.705 mmol):

A mixture of intermediate 29 (1.19 g; 4.77 mmol), triethylamine (3.33 mL; 23.9 mmol) and PdCl$_2$(dppf).CH$_2$Cl$_2$ (390 mg; 0.477 mmol) in MeOH (45 mL) was purged 3 times with CO and the reaction was refluxed for 72 hours under a CO atmosphere (1 bar). The mixture was concentrated and combined with the 2$^{nd}$ batch coming from intermediate 29 (176 mg). The resulting residue was adsorbed on silica gel and purified by column chromatography over silica gel (eluent: gradient from 100% DCM, 0% EtOAc to 0% DCM, 100% EtOAc). The fractions containing the product were collected and the solvent was evaporated affording 1.30 g of a yellow solid which was purified again by column chromatography over silica gel (eluent: gradient from 50% cyclohexane, 50% EtOAc to 0% cyclohexane, 100% EtOAc). The fractions containing the product were collected and the solvent was evaporated affording 1.08 g (72%, brown solid) of intermediate 30.

f) Preparation of Intermediate 31

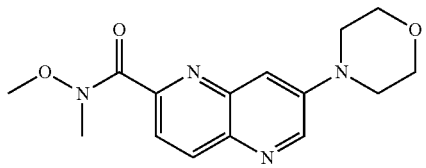 [SMILES: CON(C)C(=O)c1ccc2ncc(N3CCOCC3)cc2n1]

Under an argon atmosphere, a solution of trimethylaluminium 2 M in heptane (1.89 mL; 3.77 mmol) was added drop wise at 0° C. to a suspension of N,O-dimethylhydroxylamine hydrochloride (0.552 g; 5.66 mmol) in THF (6 mL). The resulting solution was stirred at 0° C. until the gas development ended and then at room temperature for 30 min. Then, at 0° C., this solution was added dropwise to a suspension of intermediate 30 (1.03 g; 3.77 mmol) in THF (12 mL). The resulting mixture was stirred at 0° C. for 30 min, at room temperature for 16 hours and was then cooled again to 0° C. A saturated aqueous solution of NaCl (200 mL) and a saturated aqueous solution of Na$_2$CO$_3$ (50 mL) were slowly added to reach pH 12. The aqueous layer was extracted with EtOAc (3×100 mL). The combined organic layers were dried over Na$_2$SO$_4$, filtered and concentrated.

The residue (1.5 g; brown solid) was purified by column chromatography over silica gel (eluent: gradient from 100% DCM, 0% MeOH to 95% DCM, 5% MeOH). The fractions containing the product were collected and the solvent was evaporated affording 992 mg (87%; brown solid) of intermediate 31, M.P.: 119° C. (DSC).

Example A15

Preparation of Intermediate 32

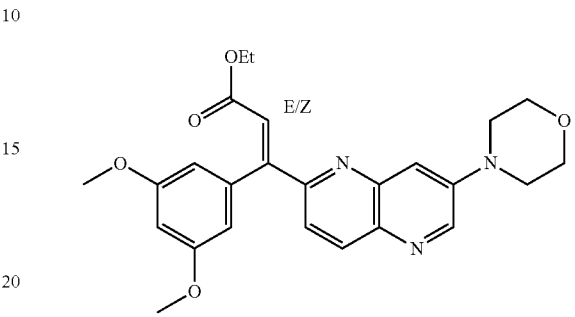

Triethyl phosphonoacetate (1.26 mL; 6.33 mmol) was added at 0° C. to a suspension of sodium hydride (253 mg; 6.33 mmol; 60% in mineral oil) in THF (10 mL). The resulting mixture was stirred for 30 min at 0° C. and for 30 min at room temperature. Then, a solution of compound 20 (800 mg; 2.11 mmol) in THF (26 mL) was added drop wise at 0° C. The reaction mixture was stirred at 0° C. for 30 min then, refluxed for 16 hours and cooled down to room temperature. Water (200 mL) and a saturated aqueous solution of NaCl (100 mL) were added. The mixture was extracted with EtOAc (3×100 mL). The combined organic layers were dried over Na$_2$SO$_4$, filtered and concentrated.

The residue (2.1 g; brown oil) was purified by column chromatography over silica gel (eluent: gradient from 50% cyclohexane, 50% EtOAc to 0% cyclohexane, 100% EtOAc). The fractions containing the product were collected and the solvent was evaporated affording 1.48 g of intermediate 32 as a undetermined E/Z mixture which was directly used as such in the next step.

Example A16 a) Preparation of Intermediate 33

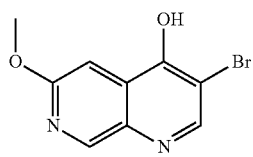

6-methoxy-1,7-naphthyridin-4(1H)-one (CAS 952059-64-2; Morgentin, R. et al. *Tetrahedron*. 2008, 64, 2772-2782) (19.2 g; 66.2 mmol) was solubilized by heating in acetic acid (300 mL) and N-bromosuccinimide (17.7 g; 99.2 mmol) was added. The mixture was stirred at room temperature for 1 hour. The resulting yellow precipitate was filtered off and successively washed with acetic acid (2×100 mL) and Et$_2$O (2×200 mL) to give 16.3 g (96%, pale yellow solid) of intermediate 33 which was used as such in the next step.

b) Preparation of Intermediate 34

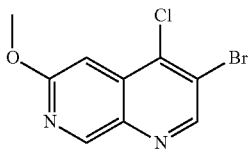

The reaction was performed on 2 batches of intermediate 33 (16.3 g; 63.9 mmol) and (10.1 g; 39.6 mmol):

POCl$_3$ (160 mL; 1.72 mol) was added to a mixture of intermediate 33 (16.3 g; 63.9 mmol) in chloroform (160 mL). The solution was stirred at reflux for 2 hours, concentrated and dried under vacuum. The residual solid was taken up with EtOAc (300 mL), cooled to 0° C. and carefully basified with a 3 M aqueous solution of NaOH (250 mL). Then, the resulting mixture was diluted with water (200 mL) and extracted with EtOAc (3×400 mL). The combined organic layers were dried over Na$_2$SO$_4$, filtered, combined with the other batch (from 10.1 g of intermediate 33) and concentrated to give 26.5 g (overall yield 94%, pale yellow solid) of intermediate 34 which was used as such in the next step.

c) Preparation of Intermediate 35

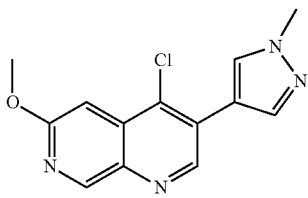 [SMILES: COc1cc2c(Cl)c(-c3cnn(C)c3)cnc2cn1]

The reaction was performed on 2 batches of intermediate 34 (21.5 g; 78.6 mmol) and (9.8 g; 358 mmol): A solution of intermediate 34 (21.5 g; 78.6 mmol), 1-methylpyrazole-4-boronic acid pinacol ester (17.2 g; 82.5 mmol), Na$_2$CO$_3$ (25 g; 236 mmol) in a mixture of dioxane (510 mL) and water (210 mL) was degassed and backfilled with argon (operation repeated 3 times). PdCl$_2$(dppf).CH$_2$Cl$_2$ (3.21 g; 3.93 mmol) was added and the resulting mixture was degassed and backfilled with argon (operation repeated twice) and stirred at 110° C. for 16 hours. After cooling to room temperature and concentration of the solution, the residue was combined with the other batch (coming from 9.8 g of intermediate 34). A mixture of EtOAc (800 mL) and MeOH (100 mL) was added. The organic layer was washed with a saturated aqueous solution of NaHCO$_3$ (500 mL) and water (300 mL). The layers were separated and the aqueous layer was extracted with a mixture of EtOAc and MeOH (9/1; 3×300 mL). The combined organic layers were dried over Na$_2$SO$_4$, filtered and evaporated to dryness. The resulting solid was triturated in Et$_2$O (500 mL), filtered off and rinsed with Et$_2$O (200 mL) to give 29.3 g (overall yield 93%, red-brown solid) of intermediate 35, M.P.: 180° C. (DSC).

d) Preparation of Intermediate 36

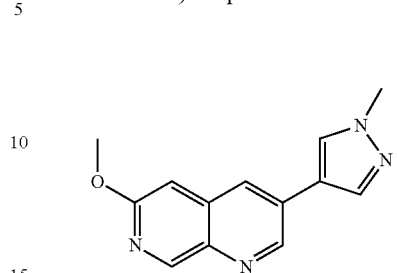

A catalytic amount of Raney Nickel, 50% slurry in water (1.88 g; 32.0 mmol) was washed twice with EtOH and collected after decantation. This catalytic amount was added to a solution of intermediate 35 (29.3 g; 107 mmol) in a mixture of EtOH (500 mL), THF (500 mL) and NaOH 1 N (112 mL; 112 mmol). The mixture was purged and stirred under hydrogen atmosphere (1 bar) at 50° C. for 65 hours. The mixture was cooled to room temperature, filtered through a pad of Celite® which was washed with a mixture of THF and EtOH (1/1; 400 mL) and concentrated. The residue (brown solid) was adsorbed on silica gel and purified by column chromatography over silica gel (eluent: from 98% DCM, 2% MeOH to 95% DCM, 5% MeOH). The pure fractions were collected and the solvent was evaporated. The resulting solid (16.5 g, orange solid) was triturated in Et$_2$O (300 mL), filtered off and washed with Et$_2$O (100 mL) to give 13.15 g (51%, beige solid) of intermediate 36, M.P.: 161° C. (DSC).

e) Preparation of Intermediate 37

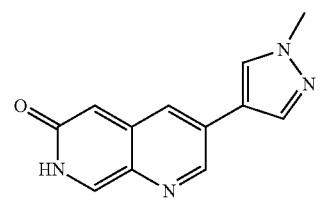 [SMILES: Cn1cc(-c2cnc3c[nH]c(=O)cc3c2)cn1]

AlCl$_3$ (16.6 g; 125 mmol) was added in one portion to a solution of intermediate 36 (5 g; 20.8 mmol) in 1,2-dichloroethane (300 mL) at room temperature. The reaction mixture was stirred at reflux for 1 hour and cooled again to room temperature. MeOH (500 mL) was added. The mixture was concentrated under reduced pressure, taken up in a mixture of MeOH and DCM (8/2; 1 L), adsorbed on silica gel and purified by column chromatography over silica gel (eluent: from 95% DCM, 5% MeOH to 80% DCM, 20% MeOH). The pure fractions were collected and the solvent was evaporated to give 13.8 g (brown solid) of intermediate 37 which was used as such in the next step.

f) Preparation of Intermediate 38

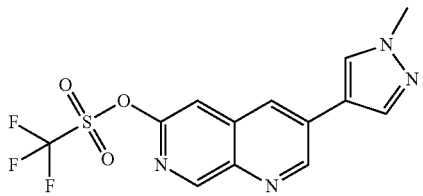 [SMILES: Cn1cc(-c2cnc3cnc(OS(=O)(=O)C(F)(F)F)cc3c2)cn1]

N-Phenyl-bis(trifluoromethanesulfonimide) (14.9 g; 41.6 mmol) was added portion wise to a suspension of intermediate 37 (13.8 g; 20.8 mmol) and Et₃N (43.5 mL; 312 mmol) in a mixture of DCM (400 mL) and DMF (100 mL) at room temperature. The reaction mixture was stirred at room temperature for 65 hours and concentrated under reduced pressure. The residue was taken up in a mixture of EtOAc (500 mL) and brine (500 mL), filtered through a pad of Celite® which was rinsed with EtOAc (200 mL) and brine (200 mL). The layers were separated and the aqueous layer was extracted with EtOAc (2×200 mL). The combined organic layers were dried over Na₂SO₄, filtered and concentrated. The residue (25.2 g, brown oil) was purified by column chromatography over silica gel (eluent: from 100% DCM to 96% DCM, 4% MeOH). The fractions containing the product were collected and the solvent was evaporated. The resulting residue (3.5 g, pale brown oil) was purified by column chromatography over silica gel (eluent: from 100% DCM to 98% DCM, 2% MeOH). The pure fractions were collected and the solvent was evaporated to give 1.02 g (14% over 2 steps from intermediate 36, beige solid) of intermediate 38.

g) Preparation of Intermediate 39

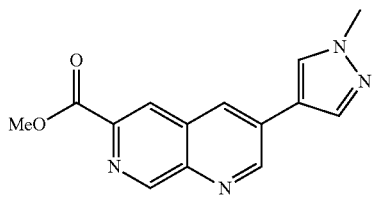 [SMILES: COC(=O)c1cc2cc(-c3cnn(C)c3)cnc2cn1]

A mixture of intermediate 38 (2.18 g; 6.08 mmol), triethylamine (4.24 mL; 30.4 mmol) and PdCl₂(dppf).CH₂Cl₂ (497 mg; 0.608 mmol) in MeOH (60 mL) was purged 3× with CO. The mixture was refluxed for 16 hours under CO atmosphere (1 bar), cooled down to room temperature and concentrated. The residue was adsorbed on silica gel and purified by column chromatography over silica gel (eluent: gradient from 100% DCM, 0% MeOH to 97% DCM, 3% MeOH). The fractions containing the product were collected and the solvent was evaporated affording, after trituration in Et₂O, 2 intermediate product fractions. Both fractions were mixed, dissolved in DCM (200 mL) and washed successively by water (200 mL) and a saturated solution of NaCl (50 mL). The aqueous layer was extracted with DCM (2×100 mL). The combined organic layers were dried over Na₂SO₄, filtered and concentrated to give 1.59 g (98%; brown solid) of intermediate 39.

h) Preparation of Intermediate 40

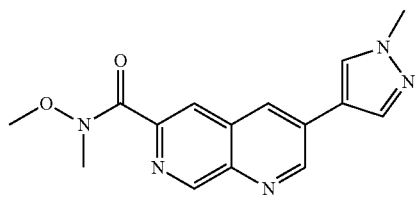 [SMILES: CON(C)C(=O)c1cc2cc(-c3cnn(C)c3)cnc2cn1]

The reaction was performed on 2 batches of intermediate 39 (1.59 g; 5.93 mmol, and 522 mg; 1.95 mmol).

Under an argon atmosphere, trimethylaluminium solution 2 M in heptane (2.97 mL; 5.93 mmol) was added drop wise at 0° C. to a suspension of N,O-dimethylhydroxylamine hydrochloride (0.868 g; 8.9 mmol) in THF (10 mL). The solution was stirred at 0° C. until gas evolution ceased and, at room temperature for 30 min. This solution was added drop wise, at 0° C., to a suspension of intermediate 39 (1.59 g; 5.93 mmol) in THF (20 mL). The resulting mixture was stirred at 0° C. for 15 min, at room temperature for 16 hours and was then cooled to 0° C. A saturated solution of NaCl (400 mL) followed by a saturated solution of Na₂CO₃ were slowly added to reach pH 12. The mixture was extracted with EtOAc (3×150 mL). The combined organic layers were dried over Na₂SO₄, filtered and concentrated to give a residue (1.76 g; brown solid) which was combined with the other batch coming from intermediate 39 (522 mg).

The resulting crude was purified by column chromatography over silica gel (eluent: gradient from 100% DCM, 0% MeOH to 95% DCM, 5% MeOH). The fractions containing the product were collected and the solvent was evaporated affording, after trituration in Et₂O and filtration, 1.80 g (77%) of intermediate 40, M.P.: 171° C. (DSC)

Example A17

Preparation of Intermediate 41

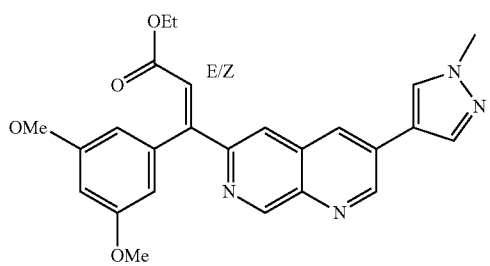 [SMILES: CCOC(=O)/C=C(\c1cc(OC)cc(OC)c1)c1cc2cc(-c3cnn(C)c3)cnc2cn1]

107 and Intermediate 41a

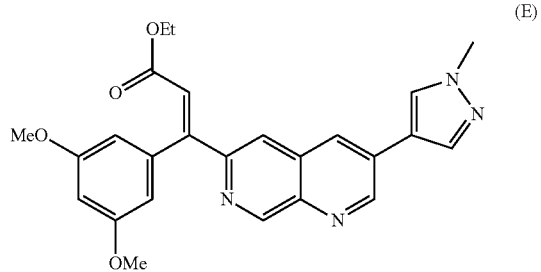 [SMILES: CCOC(=O)/C=C(\c1cc(OC)cc(OC)c1)c1cc2cc(-c3cnn(C)c3)cnc2cn1]

(E)

and Intermediate 41b

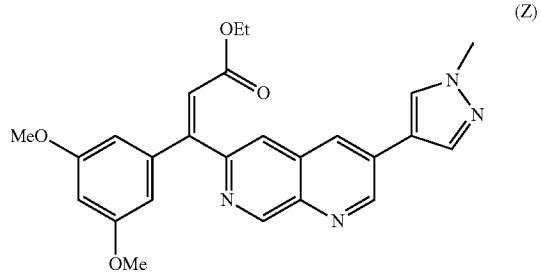 [SMILES: CCOC(=O)/C=C(/c1cc(OC)cc(OC)c1)c1cc2cc(-c3cnn(C)c3)cnc2cn1]

(Z)

Under an argon atmosphere, at 0° C., trietyl phosphonoacetate (1.18 mL; 5.94 mmol) was added to a suspension of NaH (238 mg; 5.94 mmol; 60% in mineral oil) in THF (8 mL). Then, a solution of compound 23 (740 mg; 1.98 mmol) was added drop wise at 0° C. The reaction mixture was stirred for 30 min at 0° C. and then refluxed for 16 hours. Water (300 mL) and a saturated aqueous solution of NaCl (100 mL) were added and the mixture was extracted with DCM (3×100 mL). The combined organic layers were dried over $Na_2SO_4$, filtered and concentrated.

The residue (1.9 g) was purified by column chromatography over silica gel (eluent: gradient from 100% DCM, 0% MeOH to 95% DCM, 5% MeOH). The fractions containing the product were collected and the solvent was evaporated affording, after trituration in $Et_2O$, filtration of the precipitates and drying, 3 samples:

Sample A: 122 mg of intermediate 41a (E)
Sample B: 439 mg of intermediate 41 (mixture of E and Z (E/Z))
Sample C: 260 mg of intermediate 41b (Z)

108

B. Preparation of the Final Compounds

Example B1

Preparation of Compound 1

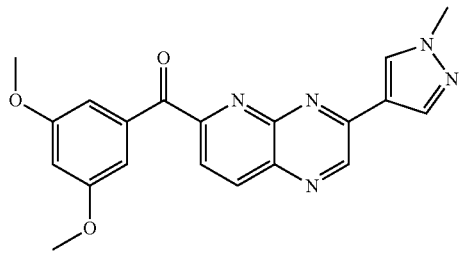

Under N2 at −78° C., 3,5-dimethoxyphenylmagnesium bromide (CAS 322640-05-1) (23 mL; 11.6 mmol) was added drop wise to a solution of intermediate 6 (2.6 g; 9.6 mmol) in THF (100 mL). The solution was stirred at −78° C. for 2.5 hours and the temperature was allowed to rise to 5° C. over a period of 2 hours. The solution was poured onto a cooled saturated solution of $NH_4Cl$. The compound was extracted with DCM and a little of MeOH. The organic layer was dried over $MgSO_4$, filtered and evaporated to dryness. The residue (5.4 g) was purified by chromatography over silica gel (Irregular SiOH 20-45 μm, 450 g; mobile phase: 0.1% $NH_4OH$, 98% DCM, 2% MeOH). The pure fractions were collected and the solvent was evaporated to give 1.65 g of intermediate 6 and 1.45 g (40%) of compound 1.

$^1H$ NMR (500 MHz, DMSO-$d_6$) δ 9.52 (s, 1H), 8.77 (s, 1H), 8.68 (d, J=8.51 Hz, 1H), 8.39 (s, 1H), 8.21 (d, J=8.51 Hz, 1H), 7.18 (d, J=1.9 Hz, 2H), 6.89 (t, J=1.9 Hz, 1H), 3.96 (s, 3H), 3.81 (s, 6H);

MS (ESI$^+$) m/z (%) (r.t. 2.64) 376 (100) [M+H]$^+$, 751 (55) [2M+H]$^+$ method A1. M.P.: 228° C. (Kofler).

Example B2

Preparation of Compound 2

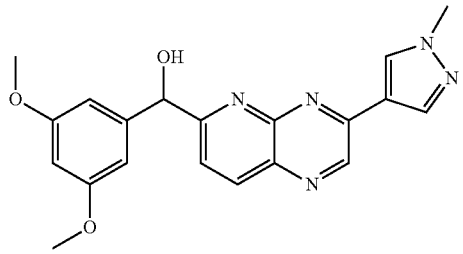 [SMILES: COc1cc(OC)cc(C(O)c2ccc3ncc(-c4cnn(C)c4)nc3n2)c1]

Under N2 at −78° C., 3,5-dimethoxyphenylmagnesium bromide (CAS 322640-05-1) (4.8 mL; 2.39 mmol) was added drop wise to a solution of intermediate 8 (0.44 g; 1.84 mmol) in THF (20 mL). The solution was stirred at −78° C. over a period of 1 hour and allowed to slowly rise to room temperature for 1 hour 30 minutes. The solution was poured onto a cooled saturated solution of $NH_4Cl$. The product was extracted with EtOAc. The organic layer was dried over $MgSO_4$, filtered and evaporated to dryness. The residue (800 mg) was purified by chromatography over silica gel (Silica 5 μm 150×30.0 mm; mobile phase: gradient from 0.2% NH₄OH, 98% DCM, 2% MeOH to 1% NH₄OH, 90% DCM, 10% MeOH). The pure fractions were collected and the solvent was evaporated to give 0.22 g (32%) of compound 2.

¹H NMR (500 MHz, DMSO-d₆) δ 9.35 (s, 1H), 8.70 (s, 1H), 8.42 (d, J=8.51 Hz, 1H), 8.34 (s, 1H), 7.91 (d, J=8.51 Hz, 1H), 6.66 (d, J=2.36 Hz, 2H), 6.43 (d, J=4.10 Hz, 1H), 6.36 (t, J=2.36 Hz, 1H), 5.84 (d, J=4.10 Hz, 1H), 3.96 (s, 3H), 3.70 (s, 6H);

MS (ESI⁺) m/z (%) (r.t. 2.22) 378 (100) [M+H]⁺, 755 (5) [2M+H]⁺ method A1.

Example B3

Preparation of Compound 3

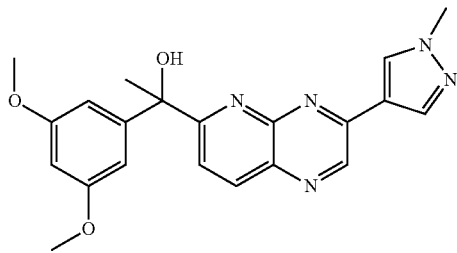 [SMILES: COc1cc(OC)cc(C(C)(O)c2ccc3ncc(-c4cnn(C)c4)nc3n2)c1]

Under N2 at −78° C., 3,5-dimethoxyphenylmagnesium bromide (CAS 322640-05-1) (3 mL; 1.50 mmol) was added drop wise to a solution of intermediate 5 (0.345 g; 1.36 mmol) in THF (20 mL). The solution was stirred at −78° C. for 2 hours. The solution was poured onto a cooled saturated solution of NH₄Cl. The product was extracted with EtOAc. The organic layer was dried over MgSO₄, filtered and evaporated to dryness. The residue (0.55 g) was purified by chromatography over silica gel (irregular 15-40 μm 30 g, mobile phase: 7% MeOH, 40% heptane, 53% EtOAc). The pure fractions were collected and the solvent was evaporated to give 80 mg of intermediate 5 and 190 mg (36%) of compound 3.

¹H NMR (500 MHz, DMSO-d₆) δ 9.36 (s, 1H), 8.75 (s, 1H), 8.25-8.45 (m, 2H), 7.93 (d, J=8.51 Hz, 1H), 6.66 (d, J=1.89 Hz, 2H), 6.34 (t, J=1.89 Hz, 1H), 6.27 (s, 1H), 3.96 (s, 3H), 3.68 (s, 6H), 1.98 (s, 3H);

MS (ESI⁺) m/z (%) (r.t. 2.38) 392 (100) [M+H]⁺, 783 (5) [2M+H]⁺ method A1

M.P.: 228° C. (Kofler).

Example B4

Preparation of Compound 4

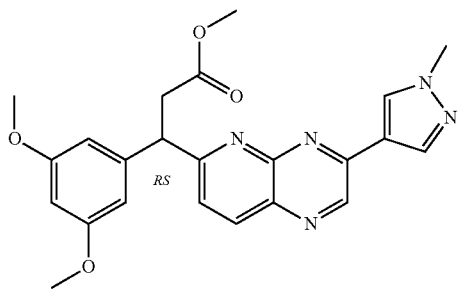 [SMILES: COC(=O)CC(c1cc(OC)cc(OC)c1)c1ccc2ncc(-c3cnn(C)c3)nc2n1]

Magnesium turnings (294 mg; 12.10 mmol) were added in one portion to a suspension of intermediate 9 (490 mg; 1.1 mmol) in THF (10 mL) and MeOH (2 mL) at room temperature. The mixture was stirred for 5 hours at room temperature. MeOH (8 mL) was added and the solution was stirred at room temperature overnight. Ice and a 10% aqueous solution of NH₄Cl were added. The mixture was filtered through a pad of Celite®. The product was extracted with a mixture of DCM and MeOH, dried over MgSO₄, filtered and evaporated. The residue (680 mg) was purified by column chromatography over silica gel (15-40 μm, 40 g, mobile phase: 0.1% NH₄OH, 99% DCM, 1% MeOH). The pure fractions were collected and the solvent was evaporated to give 260 mg (55%) of compound 4.

¹H NMR (500 MHz, DMSO-d₆) δ 9.35 (s, 1H), 8.74 (s, 1H), 8.36 (s, 1H), 8.33 (d, J=8.5 Hz), 7.73 (d, J=8.5 Hz, 1H), 6.55 (d, J=2.21 Hz, 2H), 6.35 (t, J=2.21 Hz, 1H), 4.80 (dd, J=6.0, 9.14 Hz, 1H), 3.97 (s, 3H), 3.68 (s, 6H), 3.61 (dd, J=9.14, 16.55 Hz, 1H), 3.53 (s, 3H), 3.06 (dd, J=6.0, 16.55 Hz, 1H);

MS (ESI⁺) m/z (%) (r.t. 2.57) 434 (100) [M+H]⁺, 867 (30) [2M+H]⁺ method A1.

Example B5

Preparation of Compound 5

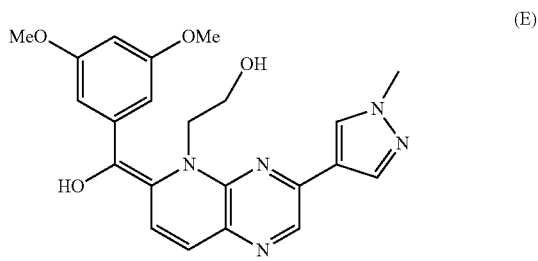 [SMILES: COc1cc(OC)cc(/C(O)=C2/C=Cc3ncc(-c4cnn(C)c4)nc3N2CCO)c1]

(E)

At 10° C., tetrabutyl ammonium fluoride (2.6 mL; 8.82 mmol) was added to a solution containing a mixture of intermediate 10 and intermediate 11 (0.315 g; 0.59 mmol) in THF (10 mL). The mixture was stirred at room temperature overnight. The solution was poured out into cooled water and the product was extracted with EtOAc. The organic layer was dried over MgSO₄, filtered and evaporated to dryness. The residue (0.54 g) was purified by column chromatography over silica gel (irregular 15-40 μm 50 g; mobile phase: 0.1% NH₄OH, 97% DCM, 3% MeOH). The pure fractions were collected and the solvent was evaporated to give 26 mg (11%) of compound 5 as the E-isomer;

¹H NMR (500 MHz, DMSO-d₆) δ 9.36 (s, 1H), 8.76 (s, 1H), 8.33-8.40 (m, 2H), 7.93 (d, J=8.83 Hz, 1H), 6.69 (d, J=2.21 Hz, 2H), 6.33 (t, J=2.21 Hz, 1H), 6.23 (s, 1H), 4.58 (t, J=4.89 Hz, 1H), 3.97 (s, 3H), 3.68 (s, 6H), 3.40-3.51 (m, 2H), 2.68-2.78 (m, 1H), 2.58-2.68 (m, 1H)

MS (ESI⁺) m/z (%) (r.t. 2.16) 422 (100) [M+H]⁺, 843 (5) [2M+H]⁺ method A1

Example B6

Preparation of Compound 6 and 7

Compound 6

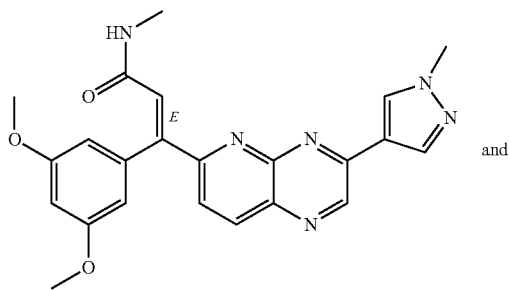

and compound 7

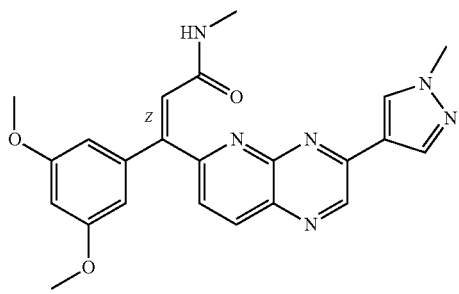

At 0° C. under N₂, a solution of trimethylaluminium 2M in toluene (3.4 mL; 6.82 mmol) was added to a solution of methylamine hydrochloride (0.21 g; 6.82 mmol) in toluene (15 mL). The solution was stirred at room temperature for 1 hour. A solution of intermediate 9 (0.76 g; 1.71 mmol) in toluene (20 mL) was added drop wise at room temperature. The solution was heated at 100° C. for 3 hours. The solution was cooled, poured onto iced water, basified with $K_2CO_3$ and EtOAc was added. The mixture was filtered through a pad of Celite®. The organic layer was washed, dried over $MgSO_4$ and evaporated. The residue (620 mg) was purified by chromatography over silica gel (15-40 μm, 24 g; mobile phase: 95% DCM, 5% MeOH, 0.1% $NH_4OH$). The fractions containing the products were collected and the solvent was evaporated. The resulting residue (310 mg) was purified by chromatography over silica gel (Silica 5 μm, 150×30.0 mm; mobile phase: gradient from 0.2% $NH_4OH$, 98% DCM, 2% MeOH to 1% $NH_4OH$, 90% DCM, 10% MeOH). The pure fractions were collected and the solvent was evaporated to give 25 mg (3%) of compound 6 and 12 mg (2%) of compound 7.

Compound 6: ¹H NMR (400 MHz, DMSO-$d_6$) δ 9.38 (s, 1H), 8.71 (s, 1H), 8.40 (d, J=8.59 Hz, 1H), 8.35 (s, 1H), 8.15-8.24 (m, 1H), 7.41 (d, J=8.59 Hz, 1H), 7.27 (s, 1H), 6.54 (t, J=2.02 Hz, 1H), 6.39 (d, J=2.02 Hz, 2H), 3.97 (s, 3H), 3.74 (s, 6H), 2.58 (d, J=4.55 Hz, 3H); MS (ESI⁺) m/z (%) (r.t. 2.20) 431 (100) [M+H]⁺, 861 (100) [2M+H]⁺ method A1

Compound 7: ¹H NMR (400 MHz, DMSO-$d_6$) δ 9.39 (s, 1H), 8.68 (s, 1H), 8.38 (d, J=8.59 Hz, 1H), 8.32 (s, 1H), 8.15 (q, J=4.55 Hz, 1H), 7.60 (d, J=8.59 Hz, 1H), 6.69 (s, 1H), 6.55 (br.s, 1H), 6.39 (d, J=2.02 Hz, 2H), 3.96 (s, 3H), 3.70 (s, 6H), 2.54 (d, J=4.55 Hz, 3H);

MS (ESI⁺) m/z (%) (r.t. 2.20) 431 (100) [M+H]⁺, 861 (50) [2M+H]⁺ method A1

Example B7

Preparation of Compound 8

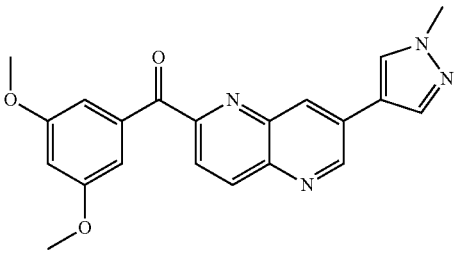 [SMILES: COc1cc(OC)cc(C(=O)c2ccc3ncc(-c4cnn(C)c4)cc3n2)c1]

The reaction was performed from 2 batches of intermediate 20 (103 mg; 0.44 mmol) and (50 mg; 0.21 mmol):

3,5-dimethoxyphenylmagnesium bromide (CAS 322640-05-1) (1.47 mL; 0.87 mmol) was added drop wise to a solution of intermediate 20 (0.100 g; 0.44 mmol) in toluene (1.2 mL) at 0° C. The reaction mixture was stirred at 0° C. for 2 hours and at room temperature overnight. The other batch (coming from 50 mg of intermediate 20) was combined with the reaction mixture for the work-up. The mixture was cooled to 0° C., quenched with a saturated solution of $NH_4Cl$ (150 mL) and extracted with EtOAc (3×100 mL). The combined organic layers were dried over $Na_2SO_4$, filtered and concentrated. The residue (1.21 g, brown oil) was purified by column chromatography over silica gel (mobile phase: from 100% DCM to 95% DCM, 5% MeOH). The fractions containing the product were collected and the solvent was evaporated. The residue (0.222 g, yellow solid) was purified by column chromatography over silica gel (15-40 μm, mobile phase: 99% EtOAc, 1% MeOH). The pure fractions were collected and the solvent was evaporated. The residue was triturated in $Et_2O$ and dried under vacuum to give 78 mg (32%, beige solid) of compound 8, M.P.: 178° C. (DSC).

Compound 8 was alternatively also prepared using the following procedure:

The reaction was performed from 2 batches of intermediate 22 (322 mg; 1.08 mmol) and (77 mg; 0.26 mmol):

3,5-dimethoxyphenylmagnesium bromide (CAS 322640-05-1) (2.19 mL; 1.30 mmol) was added drop wise to a solution of intermediate 22 (0.322 g; 1.08 mmol) in THF (10 mL) at 0° C. The reaction mixture was stirred at 0° C. for 3 hours and at room temperature for 72 hours. A saturated solution of $NH_4Cl$ (100 mL) was added and the mixture was extracted with EtOAc (3×70 mL). The combined organic layers were dried over $Na_2SO_4$, filtered and concentrated. The other batch (coming from 77 mg of intermediate 22) was combined with the reaction mixture for the purification. The residue was purified by chromatography over silica gel (mobile phase: 100% EtOAc). The pure fractions were collected and the solvent was evaporated to give 382 mg (overall yield: 76%, yellow solid) of compound 8.

Example B8

Preparation of Compound 9

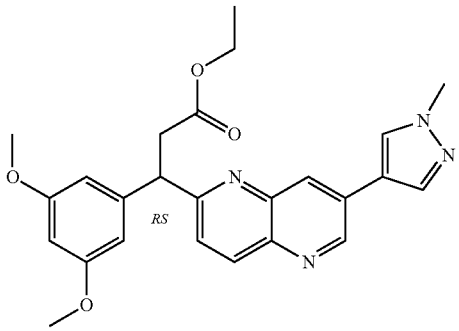 [SMILES: CCOC(=O)CC(c1cc(OC)cc(OC)c1)c1ccc2ncc(-c3cnn(C)c3)cc2n1]

Pd/C 10% (0.046 mg; 0.04 mmol) was added to a solution of intermediate 23 (0.191 mg; 0.43 mmol, E/Z mixture) in THF (2 mL) under argon. The mixture was purged with $H_2$ (3×) and was stirred at room temperature for 72 hours. The mixture was filtered through a pad of Celite®, washed with THF (200 mL) and concentrated to dryness. The residue (0.255 g) was purified by chromatography over silica gel (mobile phase: from 99% DCM, 1% MeOH to 98% DCM, 2% MeOH). The product fractions were collected and the solvent was evaporated. The resulting fraction was triturated with $Et_2O$ and dried under vacuum to give 0.112 g (58%, beige solid) of compound 9.

$^1$H NMR (400 MHz, $CDCl_3$): δ 9.07 (s, 1H), 8.37 (s, 1H), 8.19 (d, J=8.4 Hz, 1H), 7.97 (s, 1H), 7.85 (s, 1H), 7.43 (d, J=8.4 Hz, 1H), 6.48 (s, 2H), 6.33 (s, 1H), 4.73-4.82 (m, 1H), 4.09 (q, J=7.0 Hz, 2H), 4.03 (s, 3H), 3.75 (s, 6H), 3.64 (dd, J=16.4 Hz, J=9.6 Hz, 1H), 3.00 (dd, J=16.4 Hz, J=5.6 Hz, 1H), 1.18 (t, J=7.0 Hz, 3H); MS (ESI$^+$) m/z (%) (r.t. 12.27) 447 [M+H]$^+$ method D1.

M.P.: 124° C. (DSC).

Example B9

Preparation of Compound 10

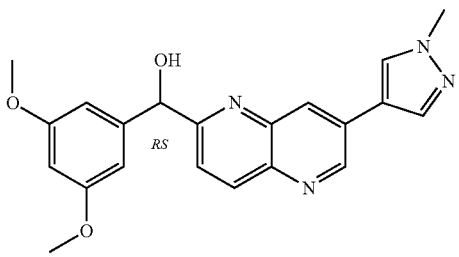 [SMILES: COc1cc(OC)cc(C(O)c2ccc3ncc(-c4cnn(C)c4)cc3n2)c1]

The reaction was performed from 2 batches of intermediate 24 (111 mg; 0.47 mmol) and (30 mg; 0.13 mmol):

3,5-dimethoxyphenylmagnesium bromide (CAS 322640-05-1) (1.57 mL; 0.93 mmol) was added drop wise to a solution of intermediate 24 (0.111 g; 0.47 mmol) in THF (2.5 mL) at 0° C. The reaction mixture was stirred at 0° C. for 3 hours and at room temperature overnight. The other batch (coming from 30 mg of intermediate 24) was combined with the reaction mixture for the work-up. The mixture was cooled to 0° C., quenched with a saturated solution of $NH_4Cl$ (100 mL) and extracted with EtOAc (3×50 mL). The combined organic layers were dried over $Na_2SO_4$, filtered and concentrated. The residue (1.11 g, yellow solid) was purified by column chromatography over silica gel (mobile phase: 100% EtOAc). The pure fractions were collected and the solvent was evaporated to give 118 mg (53%, yellow solid) of compound 10, M.P.: decomposition starting from 169° C. (DSC).

Example B10

Preparation of Compound 15

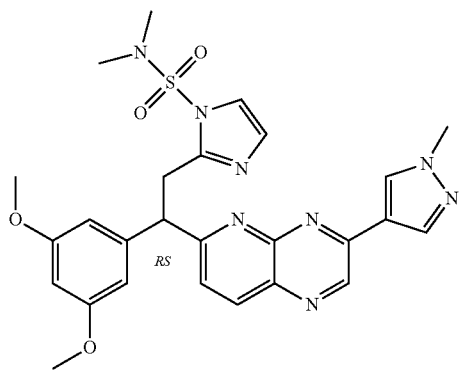 [SMILES: COc1cc(OC)cc(C(Cc2nccn2S(=O)(=O)N(C)C)c2ccc3ncc(-c4cnn(C)c4)nc3n2)c1]

Under N2 at −70° C., butyllithium 1.6 M in hexane (0.803 mL; 1.29 mmol) was added to a solution of diisopropylamine (0.211 mL; 1.50 mmol) in THF (3 mL). The solution was stirred at −70° C. for 30 minutes. This solution of lithium diisopropylamide was added drop wise to a solution of intermediate 18 (387 mg; 1.07 mmol) in THF (10 mL) at −70° C. The mixture was stirred at −70° C. for 2 hours. A solution of intermediate 19 (359 mg; 1.34 mmol) in THF (3 mL) was added drop wise, then the solution was stirred at −78° C. for 2 hours. The reaction mixture was warmed to room temperature and stirred for 1 hour. The mixture was poured into cooled water and extracted with EtOAc. The organic layer was dried over $MgSO_4$, filtered and evaporated to dryness. The residue (700 mg) was purified by chromatography over silica gel (15-40 μm, 30 g; mobile phase: 96% DCM, 4% MeOH, 0.1% $NH_4OH$. The resulting residue (40 mg) was purified by chromatography over silica gel (5 μm 150×30.0 mm; mobile phase: gradient from 0% $NH_4OH$, 100% DCM, 0% MeOH to 0.8% $NH_4OH$, 92% DCM, 8% MeOH). The resulting residue (15 mg) was purified by achiral Supercritical Fluid Chromatography on (CYANO 6 μm 150×21.2 mm; mobile phase: 0.3% isopropylamine, 87% $CO_2$, 13% MeOH). The pure fractions were collected and the solvent was evaporated to give 9 mg (2%) of compound 15.

$^1$H NMR (500 MHz, DMSO-$d_6$) δ 9.32 (s, 1H), 8.68 (s, 1H), 8.24-8.35 (m, 2H), 7.78 (d, J=8.51 Hz, 1H), 7.40 (d, J=1.58 Hz, 1H), 6.81 (d, J=1.58 Hz, 1H), 6.57 (d, J=2.21 Hz, 2H), 6.35 (t, J=2.21 Hz, 1H), 5.19 (dd, J=5.04, 10.09 Hz, 1H), 4.24 (dd, J=10.09, 16.71 Hz, 1H), 3.96 (s, 3H), 3.69 (s, 6H), 3.43 (dd, J=5.04, 16.71 Hz, 1H), 3.00 (s, 6H);

MS (ESI$^+$) m/z (%) (r.t. 2.66) 549 (100) [M+H]$^+$ method A1

Example B11

Preparation of Compound 11

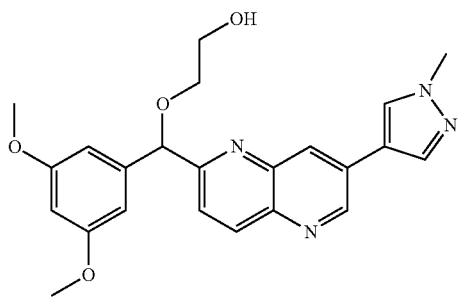 [SMILES: COc1cc(OC)cc(C(OCCO)c2ccc3ncc(-c4cnn(C)c4)cc3n2)c1]

Tetrabutylammonium fluoride 1M in THF (2.15 mL; 2.15 mmol) was added to a solution of a mixture of intermediate 25a and 25b (Example A12) (0.91 g; 0.72 mmol) in THF (3.5 mL). The mixture was stirred at room temperature for 3 hours. Ice-water (50 mL) and a saturated aqueous solution of $K_2CO_3$ (50 mL) were added and the mixture was extracted with EtOAc (3×50 mL). The combined organic layers were dried over $Na_2SO_4$, filtered and concentrated. The residue (0.400 g, yellow oil) was purified by chromatography over silica gel (eluent: 100% EtOAc to 95% EtOAc, 5% MeOH). The product fractions were collected and the solvent was evaporated. Each fraction was triturated in $Et_2O$ and dried under vacuum to give:

57 mg (beige solid) of compound 11

35 mg (beige solid) of compound 11. (Overall yield 31% over 2 steps).

$^1$H NMR (400 MHz, $CDCl_3$): δ 9.11 (s, 1H), 8.40 (s, 1H), 8.32 (d, J=9.0 Hz, 1H), 7.97 (s, 1H), 7.85 (s, 1H), 7.67 (d, J=9.0 Hz, 1H), 6.67 (s, 2H), 6.38 (s, 1H), 5.67 (s, 1H), 4.03 (s, 3H), 3.80-3.96 (m, 3H), 3.78 (s, 6H), 3.67-3.74 (m, 1H), 2.98-3.12 (m 1H);

MS (ESI$^+$) m/z (%) (r.t. 10.24) 421 [M+H]$^+$ method D1. M.P.: 139° C. (DSC).

Example B12

Preparation of Compound 12

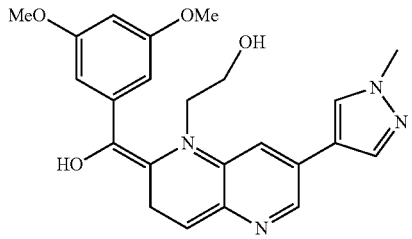

Tetrabutylammonium fluoride 1M in THF (0.133 mL; 0.46 mmol) was added to a solution of intermediate 25b (0.082 g; 0.15 mmol) in THF (1 mL). The mixture was stirred at room temperature overnight. Ice-water (20 mL) and a saturated aqueous solution of $K_2CO_3$ (20 mL) were added and the mixture was extracted with EtOAc (3×15 mL). The combined organic layers were washed with brine (25 mL), dried over $Na_2SO_4$, filtered and concentrated. The residue was triturated in $Et_2O$ and dried under vacuum. The residue (0.31 g, brown solid) was purified by chromatography over silica gel (15-40 µm; eluent: from 97% DCM, 3% MeOH to 95% DCM, 5% MeOH). The product fractions were collected and the solvent was evaporated. The residue (0.020 g, pale brown solid) was triturated in $Et_2O$ and dried under vacuum to give 0.013 g (39% over 2 steps, beige solid) of compound 12. $^1$H NMR (400 MHz, DMSO-$d_6$): δ 9.26 (s, 1H), 8.55 (s, 2H), 8.27 (d, J=8.8 Hz, 1H), 8.25 (s, 1H), 7.85 (d, J=8.8 Hz, 1H), 6.68 (s, 2H), 6.33 (s, 1H), 6.18 (s, 1H), 4.55 (br s, 1H), 3.92 (s, 3H), 3.68 (s, 6H), 3.38-3.53 (m, 2H), 2.60-2.75 (m, 2H);

MS (ESI$^+$) m/z (%) (r.t. 10.07) 421 [M+H]$^+$ method D1. M.P.: 198° C. (DSC).

Example B13

Preparation of Compound 16

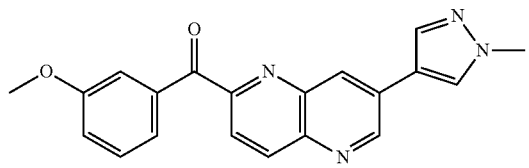

Under an argon atmosphere, at 0° C., in a round bottom flask, (3-methoxyphenyl)magnesium bromide (11 mL; 2.15 mmol; 0.69 M in THF) was added drop wise to a solution of intermediate 22 (0.5 g; 1.68 mmol) in THF (17 mL) and the reaction mixture was stirred at 0° C. for 1 hour. An aqueous saturated solution of $NH_4Cl$ was added and the mixture was extracted with EtOAc (3×100 mL). The combined organic layers were dried over $Na_2SO_4$, filtered and concentrated.

The crude (0.618 g) was purified by column chromatography over silica gel (eluent: 100% EtOAc). The fractions containing the product were collected and the solvent was evaporated. affording after trituration in $Et_2O$ and filtration of the precipitates, 2 samples of compound 16:

134 mg of compound 16 (containing 9% wt of $Et_2O$ as evaluated by 1H NMR)

474 mg (82%) of compound 16. The NMR data of this fraction are reported below.

$^1$H NMR (CHLOROFORM-d, 400 MHz): δ=9.25 (br. s, 1H), 8.57 (d, J=8.6 Hz, 1H), 8.51 (s, 1H), 8.25 (d, J=8.6 Hz, 1H), 7.99 (s, 1H), 7.88 (s, 1H), 7.77 (d, J=7.8 Hz, 1H), 7.74 (br. s., 1H), 7.45 (t, J=7.8 Hz, 1H), 7.22 (d, J=7.8 Hz, 1H), 4.04 (s, 3H), 3.90 ppm (s, 3H)

MS (ESI$^+$) m/z (%) (r.t. 12.47) 345 [M+H]$^+$ (method D1); MP=173° C. (DSC)

Example B14

Preparation of Compound 20

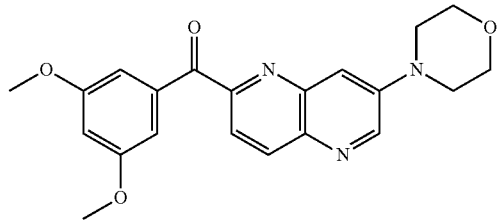 [SMILES: COc1cc(OC)cc(C(=O)c2ccc3ncc(N4CCOCC4)cc3n2)c1]

Under an argon atmosphere, 3,5-dimethoxyphenylmagnesium bromide (CAS 322640-05-1) (5.89 mL; 3.5 mmol; 0.59 M in THF) was added drop wise at 0° C. to a solution of intermediate 31 (0.96 g; 3.18 mmol) in THF (30 mL). The resulting mixture was stirred at 0° C. for 30 min and at room temperature for 16 hours. Then, a saturated aqueous solution of NH₄Cl (200 mL) was added and the mixture was extracted with EtOAc (3×100 mL). The combined organic layers were dried over Na₂SO₄, filtered and concentrated.

The residue (1.4 g; yellow solid) was purified by column chromatography over silica gel (eluent: gradient from 50% cyclohexane, 50% EtOAc to 0% cyclohexane, 100% EtOAc). The fractions containing the product were collected and the solvent was evaporated. affording after trituration in Et₂O and filtration, 837 mg (69%; yellow solid) of compound 20.

$^1$H NMR (400 MHz, DMSO-d$_6$) δ 9.13 (s, 1H), 8.48 (br. s., 1H), 7.98 (br. s, 1H), 7.59 (s, 1H), 7.15 (s., 2H), 6.84 (s, 1H), 3.91-3.72 (m, 10H), 3.51-3.39 (m, 4H)

MS (ESI⁺) m/z (%) (r.t. 12.42) 380 [M+H]⁺ (method D1); MP: 159° C. (DSC)

Example B15

Preparation of Compound 21

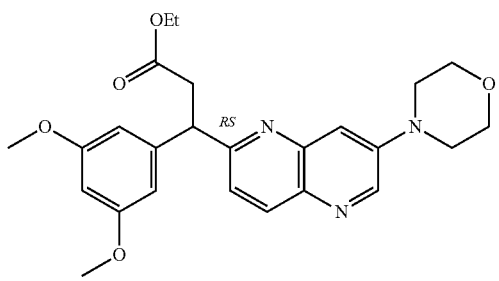 [SMILES: CCOC(=O)CC(c1cc(OC)cc(OC)c1)c1ccc2ncc(N3CCOCC3)cc2n1]

Pd/C, 10% loading (90 mg; 0.084 mmol) was added to a solution of intermediate 32 (1.48 g; 2.11 mmol) in THF (12 mL) and EtOH (4 mL). The mixture was purged 3 times with H₂ and was stirred at room temperature for 72 hours under 1 atm of H₂. The reaction mixture was filtered through a pad of celite which was washed with EtOH. The filtrate was concentrated to dryness.

The residue (1.48 g, brown oil) was purified by column chromatography over silica gel (eluent: gradient from 50% cyclohexane, 50% EtOAc to 90% EtOAc, 10% MeOH). The fractions containing the product were collected and the solvent was evaporated affording 837 mg of a yellow solid which was taken up with Et₂O. The resulting precipitate was filtered to afford, after drying, 183 mg (19% yield over 2 steps) of compound 21.

$^1$H NMR (400 MHz, DMSO-d$_6$) δ 8.91 (s, 1H), 8.11 (d, J=8.2 Hz, 1H), 7.48 (s., 1H), 7.41 (d, J=8.2 Hz, 1H), 6.50 (s, 2H), 6.33 (s, 1H), 4.63-4.71 (m, 1H), 3.97 (q, J=7.1 Hz, 2H), 3.76-3.87 (m, 4H), 3.68 (s, 6H), 3.46 (dd, J=9.8, 16.7 Hz, 1H), 3.34-3.41 (m, 4H), 2.99 (dd, J=5.9, 16.7. Hz, 1H), 1.06 (t, J=7.1 Hz, 3H)

MS (ESI⁺) m/z (%) (r.t. 11.82) 452 [M+H]⁺ (method D1); M.P.: 166° C. (DSC)

Example B16

Preparation of Compound 23

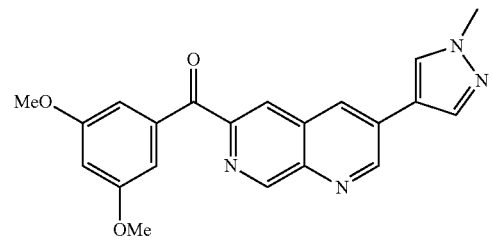 [SMILES: COc1cc(OC)cc(C(=O)c2cc3cc(-c4cnn(C)c4)cnc3cn2)c1]

Under an argon atmosphere, at 0° C., 3,5-dimethoxyphenylmagnesium bromide (CAS 322640-05-1) (10.4 mL; 6.18 mmol; 0.59 M in THF) was added drop wise to a solution of intermediate 40 (1.67 g; 6.62 mmol) in THF (90 mL). The reaction mixture was stirred at 0° C. for 1 hour, and then at room temperature for 16 hours. A saturated aqueous solution of NH₄Cl (500 mL) was added and the mixture was extracted with EtOAc (3×500 mL). The combined organic layers were dried over Na₂SO₄, filtered and concentrated.

The residue (2.8 g) was purified by column chromatography over silica gel (eluent: gradient from 99% DCM, 1% MeOH to 97% DCM, 3% MeOH). The fractions containing the product were collected and the solvent was evaporated. The resulting residue was triturated in Et₂₀ to afford, after filtration, 1.5 g (71%) of compound 23.

$^1$H NMR (400 MHz, DMSO-d$_6$) δ 9.49 (s, 1H), 9.41 (s, 1H), 8.77 (s, 1H), 8.53 (s, 1H), 8.47 (s, 1H), 8.21 (s, 1H), 7.12 (s, 2H), 6.83 (s, 1H), 3.94 (s, 3H), 3.80 (s, 6H)

MS (ESI⁺) m/z (%) (r.t. 12.04) 375 [M+H]⁺ (method D1); MP: 189° C. (DSC)

Example B17

Preparation of Compound 24

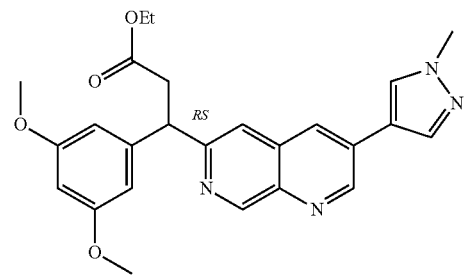 [SMILES: CCOC(=O)CC(c1cc(OC)cc(OC)c1)c1cc2cc(-c3cnn(C)c3)cnc2cn1]

Under argon, Pd/C (100 mg; 10% loading) was added to a solution of intermediate 41 (662 mg; 2.42 mg) in THF (12 mL). Then, the mixture was purged with H₂ (3 times) and stirred at room temperature for 48 hours under. EtOH (4 mL) was added. The reaction mixture was purged with H₂ (3 times), stirred for 16 hours under H₂ atmosphere (1 atm) and then, filtered through a pad of celite which was washed with THF (200 mL). The precipitate was concentrated and the residue (772 mg) was purified by column chromatography over silica gel (eluent: gradient from 99% DCM, 1% MeOH to 95% DCM, 5% MeOH). The fractions containing the product were collected and the solvent was evaporated. The residue was taken up with Et₂O and the precipitate was filtered giving, after drying, 346 mg (32%; white solid) of compound 24.

¹H NMR (400 MHz, DMSO-d₆) δ 9.31-9.23 (m, 2H), 8.48 (s, 1H), 8.43 (s, 1H), 8.17 (s, 1H), 7.69 (s, 1H), 6.57 (s, 2H), 6.34 (s, 1H), 4.72-4.64 (m, 1H), 3.98 (q, J=7.2 Hz, 2H), 3.92 (s, 3H), 3.70 (s, 6H), 3.42 (dd, J=8.6, 15.6 Hz, 1H), 3.06 (dd, J=6.6, 15.6 Hz, 1H), 1.05 (t, J=7.2 Hz, 3H)

MS (ESI⁺) m/z (%) (r.t. 11.66) 447 [M+H]⁺ (method D1); M.P.: 138° C. (DSC)

Example B18

Preparation of Compound 26

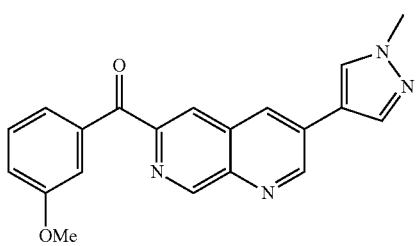 [SMILES: COc1cccc(C(=O)c2cc3cc(-c4cnn(C)c4)cnc3cn2)c1]

Under an argon atmosphere, at 0° C., in a round bottom flask, (3-methoxyphenyl)magnesium bromide (0.487 mL; 0.336 mmol; 0.69 M in THF) was added to a solution of intermediate 40 (0.1 g; 0.336 mmol) in THF (6 mL). The reaction mixture was stirred at 0° C. for 1 hour and, at room temperature for 16 hours. A saturated aqueous solution of NH₄Cl(50 mL) was added and the mixture was extracted with EtOAc (3*25 mL). The combined organic layers were dried over Na₂SO₄, filtered and concentrated.

The residue (121 mg) was purified by column chromatography over silica gel (eluent: 100% EtOAc). The fractions containing the product were collected and the solvent was evaporated. The resulting solid was taken up with Et₂O. The precipitate was filtered and dried to afford 75 mg (65%; white solid) of compound 26.

¹H NMR (400 MHz, DMSO-d₆) δ 9.50 (s, 1H), 9.42 (s, 1H), 8.78 (s, 1H), 8.54 (s, 1H), 8.49 (s, 1H), 8.22 (s, 1H), 7.58 (d, J=7.50 Hz, 1H), 7.54 (br. s., 1H), 7.50 (t, J=7.50 Hz, 1H), 7.28 (d, J=7.50 Hz, 1H), 3.95 (s, 3H), 3.83 (s, 3H)

MS (ESI⁺) m/z (%) (r.t. 11.70) 345 [M+H]⁺ (method D1); M.P.: 198° C. (DSC)

Conversion Reactions

Example C1

Preparation of Compound 14

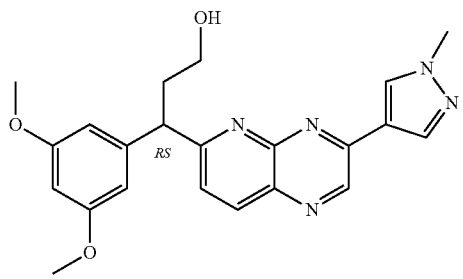 [SMILES: COc1cc(OC)cc(C(CCO)c2ccc3ncc(-c4cnn(C)c4)nc3n2)c1]

Lithium aluminum hydride (45.5 mg; 1.2 mmol) was added to a solution of compound 4 (130 mg; 0.3 mmol) in THF (4 mL) at 0-5° C. under nitrogen. The mixture was stirred for 1 hour at 0-5° C. EtOAc was carefully added followed by water. The mixture was filtered through a pad of Celite®. The filtrate was decanted. The organic layer was dried over MgSO₄, filtered and evaporated. The residue (158 mg) was purified by chromatography over silica gel (5 μm 150×30.0 mm; mobile phase: gradient from 0.2% NH₄OH, 98% DCM, 2% MeOH to 1.2% NH₄OH, 88% DCM, 12% MeOH). The pure fractions were collected and the solvent was evaporated to give 13 mg (11%) of compound 14.

¹H NMR (500 MHz, DMSO-d₆) δ 9.34 (s, 1H), 8.74 (s, 1H), 8.36 (s, 1H), 8.32 (d, J=8.51 Hz, 1H), 7.70 (d, J=8.51 Hz, 1H), 6.56 (d, J=2.21 Hz, 2H), 6.34 (t, J=2.21 Hz, 1H), 4.53 (t, J=5.04 Hz, 1H), 4.46 (t, J=7.57 Hz, 1H), 3.96 (s, 3H), 3.69 (s, 6H), 3.34-3.40 (m, 2H), 2.52-2.57 (m, 1H), 2.17-2.26 (m, 1H);

MS (ESI⁺) m/z (%) (tr 2.25) 406 (100) [M+H]⁺ method A1

Example C2

Preparation of Compound 13

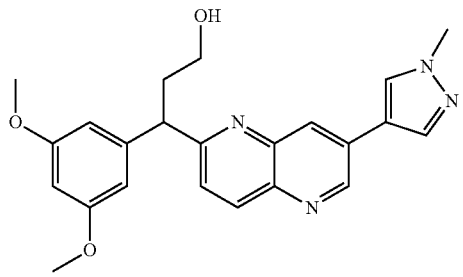 [SMILES: COc1cc(OC)cc(C(CCO)c2ccc3ncc(-c4cnn(C)c4)cc3n2)c1]

Lithium aluminium hydride (0.029 g; 0.75 mmol) was added portion wise to a solution of compound 9 (0.112 g; 0.25 mmol) in THF (2.5 mL) at 0° C. The reaction mixture was stirred at 0° C. for 1 hour. Water (0.5 mL) was slowly added at 0° C. Then the reaction mixture was diluted with a saturated aqueous solution of NH₄Cl (5 mL), water (10 mL) and extracted with a mixture of DCM/MeOH (2×30 mL: 9/1). The combined organic layers were dried over Na₂SO₄, filtered and concentrated. The residue (0.103 g, orange foam) was purified by column chromatography over silica gel (eluent: from 97% DCM, 3% MeOH to 95% DCM, 5% MeOH). The product fractions were collected and the solvent was evaporated. The residue (0.082 g) was sonicated in Et₂O (5 mL). The solid was filtered off, rinsed with Et₂O (2 mL) and dried under vacuum at 80° C. This solid (0.071 g, white solid) was purified by column chromatography over RP-C18 (eluent: from 99.5% DCM, 0.5% MeOH to 98% DCM, 2% MeOH). The product fractions were collected and the solvent was evaporated. The residue was sonicated in Et₂O (5 mL). The solid was filtered off, rinsed with Et₂O (2 mL) and dried under vacuum at 80° C. for 65 hour to give 37 mg (36%, white solid) of compound 13.

$^1$H NMR (400 MHz, CDCl₃): δ 9.13 (s, 1H), 8.50 (s, 1H), 8.29 (d, J=8.4 Hz, 1H), 8.00 (s, 1H), 7.89 (s, 1H), 7.45 (d, J=8.4 Hz, 1H), 6.49 (s, 2H), 6.36 (s, 1H), 4.62 (br s, 1H), 4.03 (s, 3H), 3.68-3.85 (m, 8H), 2.42-2.64 (m, 2H);

MS (ESI⁺) m/z (%) (r.t. 10.10) 405 (100) [M+H]⁺ method D1.

M.P.: 153° C. (DSC).

Example C3

Preparation of Compound 17

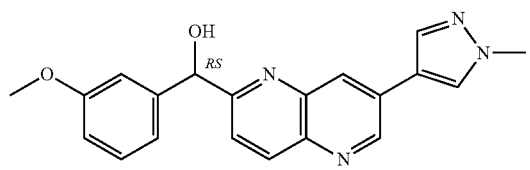

Under an argon atmosphere, at 0° C., sodium borohydride (22 mg; 0.584 mmol) was added to compound 16 (0.134 mg; 0.389 mmol) diluted in methanol (3 mL) and DCM (3 mL). The reaction mixture was stirred at 0° C. for 2 hours and at room temperature for 2 hours. Then, the mixture was concentrated to dryness. The residue was dissolved in EtOAc (30 mL) and the organic layer was washed with H₂O (30 mL). The aqueous layer was extracted with EtOAc (3×10 mL). The combined organic layers were dried over Na₂SO₄, filtered and concentrated.

The residue (153 mg) was purified by column chromatography over silica gel (eluent: gradient from 99% DCM 1% MeOH to 97% DCM 3% MeOH). The fractions containing the product were collected and the solvent was evaporated affording, after trituration in Et₂O and filtration, 103 mg (76%) of compound 17.

$^1$H NMR (DMSO-d₆, 400 MHz): δ=9.25 (s, 1H), 8.47-8.59 (m, 2H), 8.33 (d, J=8.8 Hz, 1H), 8.22 (s, 1H), 7.83 (d, J=8.8 Hz, 1H), 7.22 (t, J=8.0 Hz, 1H), 7.06 (br. s., 1H), 7.01 (d, J=8.0 Hz, 1H), 6.79 (d, J=8.0 Hz, 1H), 6.39 (s, 1H), 5.87 (s, 1H), 3.91 (s, 3H), 3.72 ppm (s, 3H)

MS (ESI⁺) m/z (%) (r.t. 10.33) 347 [M+H]⁺ (method D1);

M.P.: 176° C. (DSC)

Example C4

Preparation of Compound 18

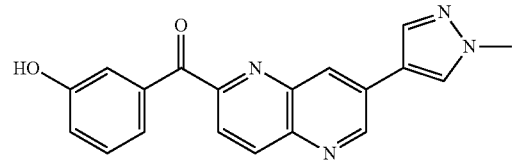 [SMILES: Cn1cc(-c2cnc3ccc(C(=O)c4cccc(O)c4)nc3c2)cn1]

Under an argon atmosphere, at 0° C., 1M boron tribromide in DCM (3.84 mL; 3.84 mmol) was added drop wise to a solution of compound 16 (264 mg; 0.767 mmol) in DCM (10 mL). The reaction mixture was stirred 1 hour at 0° C. and 16 hours at room temperature. Then, 1N aqueous HCl (150 mL) was added, followed by saturated aqueous NaHCO₃. The aqueous layer was extracted with a 95/5 mixture of DCM/MeOH (3*200 mL). The combined organic layers were dried and concentrated to give 134 mg of an intermediate residue A. The precipitate in the aqueous layer was filtered and washed with water to give 398 mg of an intermediate residue B.

The intermediate residues A and B were combined and stirred overnight in aqueous 3M NaOH (100 mL). Then, aqueous 3M HCl was added to reach pH 1 followed by saturated aqueous NaHCO₃ (50 mL) to reach pH 8. The resulting precipitate was filtered, adsorbed on silica gel and purified by column chromatography over silica gel (eluent: gradient from 99% DCM, 1% MeOH to 95% DCM, 5% MeOH). The fractions containing the product were collected and the solvent was evaporated. The resulting residue was triturated in Et₂O (300 mL), filtered off and washed with Et₂O (100 mL) to give, after drying, 196 mg (77%, green solid) of compound 18.

$^1$H NMR (400 MHz, DMSO-d₆) δ 9.90 (br. s., 1H), 9.45 (s, 1H), 8.69 (s, 1H), 8.60 (d, J=8.3 Hz, 1H), 8.59 (s, 1H), 8.29 (s, 1H), 8.14 (d, J=8.3 Hz, 1H), 7.49 (d, J=7.8 Hz, 1H), 7.41 (br s., 1H) 7.38 (t, J=7.8 Hz, 1H), 7.11 (d, J=7.8 Hz, 1H), 3.92 (s; 3H)

MS (ESI⁺) m/z (%) (r.t. 11.44) 331 [M+H]⁺ (method D1);

M.P.: 218° C. (DSC).

Example C5

Preparation of Compound 19

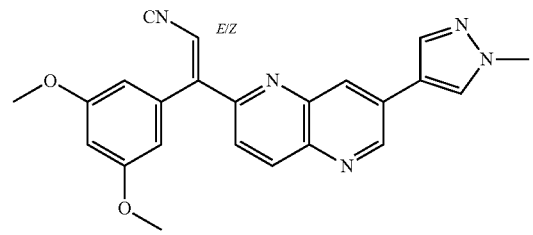

Under an argon atmosphere, at 0° C., diethyl cyanophosphonate (5.05 mL; 31.2 mmol) was added to a suspension of sodium hydride (1.25 g; 31.2 mmol; 60% dispersion in mineral oil) in THF (40 mL). Then, a solution of compound 8 (3.90 g; 10.4 mmol) was added drop wise at 0° C. The

123 reaction mixture was stirred at 0° C. for 30 min at 0° C. and then, refluxed for 16 hours. Water (200 mL) and a saturated NaCl solution (300 mL) were added and the resulting mixture was extracted with EtOAc (4×300 mL). The combined organic layers were dried over Na$_2$SO$_4$, filtered and concentrated.

The residue (6.4 g) was purified by column chromatography over silica gel (eluent: 100% EtOAc). The fractions containing the product were collected and the solvent was evaporated affording 4 g (97%, green solid) of compound 19 as a mixture of isomer E (about 80%) and isomer Z (about 20%).

Example C6

Preparation of Compound 22

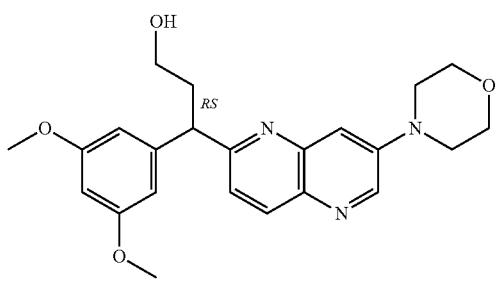 [SMILES: COc1cc(OC)cc(C(CCO)c2ccc3ncc(N4CCOCC4)cc3n2)c1]

Under an argon atmosphere, lithium aluminium hydride (0.013 g; 0.348 mmol) was added to a solution of compound 21 (0.157 g; 0.348 mmol) in THF (3.5 mL) at 0° C. and the reaction mixture was stirred at room temperature for 1 hour. EtOAc (20 mL) was added drop wise at 0° C. followed by water (20 mL). The mixture was filtered through a pad of celite which was washed with a mixture of DCM/MeOH (9/1; 50 mL). The filtrate was washed with a saturated solution of NaCl (50 mL) and the aqueous layer was extracted with a mixture of DCM/MeOH (9/1; 2×50 mL). The combined organic layers were dried over MgSO$_4$, filtered and concentrated.

The residue (117 mg) was purified by column chromatography over silica gel (eluent: 100% EtOAc, 0% MeOH to 95% EtOAc, 5% MeOH). The fractions containing the product were collected and the solvent was evaporated affording, after co-evaporation with Et$_2$O, 2 samples:

21 mg of compound 22 contaminated with impurities (according to tlc)

68 mg (48%; yellow solid) of compound 22

$^1$H NMR (400 MHz, DMSO-d$_6$) δ 8.91 (s, 1H), 8.12 (d, J=8.4 Hz, 1H), 7.52 (s, 1H), 7.44 (d, J=8.4 Hz, 1H), 6.53 (s, 2H), 6.32 (s, 1H), 4.50 (br. s., 1H), 4.27-4.41 (m, 1H), 3.88-3.75 (m, 4H), 3.69 (s, 6H), 3.36-3.44 (m, 6H, partially hidden by water peak), 2.50-2.38 (m, 1H, hidden by DMSO), 2.11-2.26 (m, 1H)

MS (ESI$^+$) m/z (%) (r.t. 9.78) 410 [M+H]$^+$ (method D1);

M.P.: 170° C. (DSC)

Example C7

Preparation of Compound 25

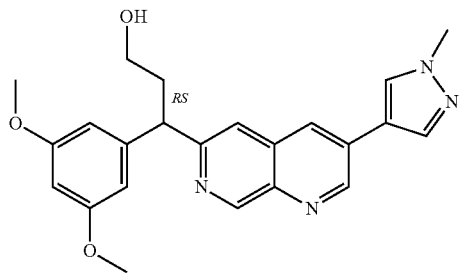 [SMILES: COc1cc(OC)cc(C(CCO)c2cc3cc(-c4cnn(C)c4)cnc3cn2)c1]

Under an argon atmosphere, at 0° C., lithium aluminium hydride (50 mg; 1.33 mmol) was added to a solution of compound 24 (298 mg; 0.667 mmol) in THF 8 mL and the reaction mixture was stirred at 0° C. for 16 hours. Then, EtOAc (50 mL) was added drop wise at 0° C. The mixture was filtered through a pad of celite which was washed with a mixture of DCM/MeOH (9/1; 100 ml). The filtrate was washed with a saturated aqueous solution of NaCl (100 ml) and the aqueous layer was extracted with DCM/MeOH (9/1; 2*100 mL). The combined organic layer were dried over Na$_2$SO$_4$, filtered and concentrated.

The residue (318 mg) was purified by column chromatography over silica gel (eluent: 95% DCM, 5% MeOH to 90% DCM, 10% MeOH). The fractions containing the product were collected and the solvent was evaporated affording 2 samples:

sample A: 113 mg of compound 25 not pure enough sample B: 190 mg of compound 25 not pure enough Sample A was purified again by chromatography over silica gel (eluent: 95% DCM, 5% MeOH to 90% DCM, 10% MeOH). The fractions containing the product were collected and the solvent was evaporated. The residue was taken up with Et$_2$O and the precipitate was filtered affording after filtration 55 mg (20%; white solid) of compound 25.

$^1$H NMR (400 MHz, DMSO-d$_6$) δ 9.40-9.16 (m, 2H), 8.39-8.53 (m, 2H), 8.16 (s, 1H), 7.69 (s, 1H), 6.57 (s, 2H), 6.32 (s, 1H), 4.50 (br. s., 1H), 4.40-4.28 (m, 1H), 3.92 (s, 3H), 3.70 (s, 6H), 3.45-3.20 (m, 2H, hidden by water peak), 2.60-2.39 (m, 1H, hidden by DMSO peak), 2.06-2.27 (m, 1H)

MS (ESI$^+$) m/z (%) (r.t. 9.85) 405 [M+H]$^+$ (method D1);

M.P.: 116° C. (DSC)

Example C8

Preparation of Compound 27

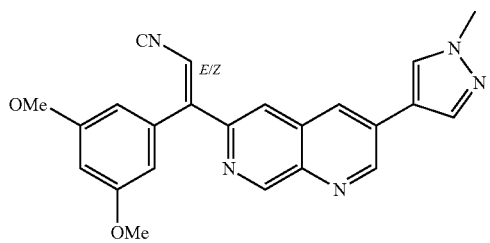

compound 27a:

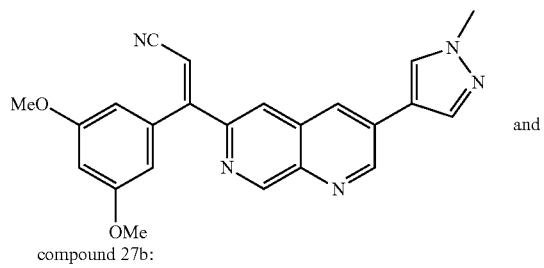

(E)

and compound 27b:

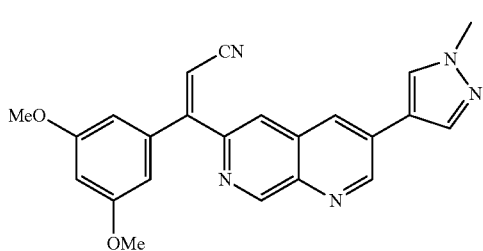

(Z)

Under an argon atmosphere, at 0° C., diethyl cyanomethylphosphonate (959 mL; 5.94 mmol) was added to a suspension of NaH (238 mg; 5.94 mmol; 60% in mineral oil) in THF (8 mL). The reaction mixture was stirred at 0° C. for 30 min and 1 hour at room temperature. Then, at 0° C., a solution of compound 23 (0.740 mg; 1.98 mmol) in THF (24 mL) was added drop wise. The mixture was stirred at 0° C. for 30 min and refluxed for 16 hours. Water (300 mL) and a saturated aqueous solution of NaCl (100 mL) were added. The mixture was extracted with DCM (3×100 mL). The combined organic layers were dried over $Na_2SO_4$, filtered and concentrated.

The residue (1.30 g) was purified by column chromatography over silica gel (eluent: 100% DCM, 0% MeOH to 95% DCM, 5% MeOH). The fractions containing the product were collected and the solvent was evaporated. The residue was taken up with $Et_2O$ and the precipitate was filtered to afford, after drying, 489 mg (62%) of compound 27 as a mixture of E and Z isomers (E/Z).

Compound 27 was purified by column chromatography over silica gel (Spherical SiOH, Eluent: gradient from 71% Heptane, 1% MeOH (+10% $NH_4OH$), 28% AcOEt to 0% Heptane, 20% MeOH (+10% $NH_4OH$), 80% EtOAc). The fractions containing the product were collected and the solvent was evaporated. The resulting residues were taken up with $Et_2O$ and the precipitates were filtered to afford, after drying:

157 mg of compound 27a (E)

$^1$H NMR (500 MHz, DMSO-$d_6$) δ 9.38 (s, 1H), 9.37 (d, J=2.1 Hz, 1H), 8.61 (d, J=2.1 Hz, 1H), 8.47 (s, 1H), 8.15 (s, 1H), 7.56 (s, 1H), 7.01 (s, 1H), 6.72 (t, J=2.2 Hz, 1H), 6.65 (d, J=2.2 Hz, 2H), 3.90 (s, 3H), 3.81 (s, 6H)

MS (ESI$^+$) m/z (%) (r.t. 2.75) 398 [M+H]$^+$ (method A1);
M.P.: 252° C. (kofler)

40 mg of compound 27b (Z)

$^1$H NMR (500 MHz, DMSO-$d_6$) δ 9.43 (d, J=1.9 Hz, 1H), 9.41 (s, 1H), 8.65 (d, J=1.9 Hz, 1H), 8.52 (s, 1H), 8.19 (s, 1H), 7.95 (s, 1H), 6.65 (t, J=2.1 Hz, 1H), 6.56 (d, J=2.1 Hz, 2H), 6.50 (s, 1H), 3.93 (s, 3H), 3.74 (s, 6H)

MS (ESI$^+$) m/z (%) (r.t. 2.61) 398 [M+H]$^+$ (method A1);
M.P.: 180° C. (kofler)

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Analytical Part
LC/GC/NMR

The LC/GC data reported were determined as follows.

General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method A1

In addition to the general procedure A: Reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

General Procedure B

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3.15 kV and the source temperature was maintained at 110° C. on the ZQ™ (simple quadrupole Zspray™ mass spectrometer from Waters). Nitrogen was used as the nebulizer gas. Data acquisition was performed with a Waters-Micromass MassLynx-Openlynx data system.

Method B1

In addition to the general procedure B: Reversed phase HPLC was carried out on a X-Bridge C18 column (3.5 μm, 4.6×100 mm) with a flow rate of 0.8 ml/min. Two mobile phases (mobile phase A: 100% 7 mM ammonium acetate; mobile phase B: 100% acetonitrile; were employed to run a gradient condition from 80% A, 20% B (hold for 0.5 minute) to 10% A, 90% B in 4.5 minutes, hold at 10% A and 90% B for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

General Procedure C

The LC measurement was performed using a UPLC (Ultra Performance Liquid Chromatography) H-Class (Waters) system comprising a quaternary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3. kV and the source temperature was maintained at 130° C. on the SQD2 (simple quadrupole mass spectrometer from Waters). Nitrogen was used as the nebulizer gas. Data acquisition was performed with a Waters-Micromass MassLynx-Openlynx data system.

Method C1

In addition to the general procedure C: Reversed phase UPLC was carried out on a Nucleoshell RP18 column from Macherey Nagel (2.7 µm, 3×50 mm) with a flow rate of 0.6 ml/min. Two mobile phases (mobile phase A: 95% 7 mM ammonium acetate/5% acetonitrile; mobile phase B: 100% acetonitrile) were employed to run a gradient condition from 95% A and 5% B (hold for 0.25 minutes) to 5% A and 95% B in 0.75 minutes, hold for 1.9 min and back to the initial conditions in 0.3 min. An injection volume of 0.7 µl was used. Cone voltage was 30V for positive and negative ionization mode. Mass spectra were acquired by scanning from 100 to 1000 in 0.15 seconds using an interscan delay of 0.05 seconds.

General Procedure D

The HPLC measurement was performed using an HPLC 1100/1200 (Agilent) system comprising a quaternary pump with degasser, an autosampler, a diode-array detector (DAD) and a column as specified in the respective methods below, the column is held at a room temperature. The MS detector (MS-Agilent simple quadrupole) was configured with an electrospray-APCI ionization source. Nitrogen was used as the nebulizer gas. Data acquisition was performed with a Chemstation data system.

Method D1

In addition to the general procedure D: Reversed phase HPLC was carried out on a Agilent Eclipse C18 column (5 µm, 4.6×150 mm) with a flow rate of 1 ml/min. Two mobile phases (mobile phase A: Water TFA 0.1%; mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 µl was used. The capillary voltage was 2 kV, the corona discharge was held at 1 µA and the source temperature was maintained at 250° C. A variable voltage was used for the fragmentor. Mass spectra were acquired in electrospray ionization and APCI in positive mode, by scanning from 80 to 1000 amu.

DSC:

For a number of compounds, melting points (m.p.) were determined with a DSC1 (Mettler-Toledo). Melting points were measured with a temperature gradient of 5 or 10° C./minute. Maximum temperature was 350° C. Values are peak values.

For a number of compounds, melting points were obtained with a Kofler hot bench, consisting of a heated plate with linear temperature gradient, a sliding pointer and a temperature scale in degrees Celsius.

NMR Data

The NMR experiments were carried out using a Bruker Avance III 500 and a Bruker Avance DRX 400 spectrometers at ambient temperature, using internal deuterium lock and equipped with reverse triple-resonance ($^1$H, $^{13}$C, $^{15}$N TXI) probe head for the 500 MHz and with reverse double-resonance ($^1$H, $^{13}$C, SEI) probe head for the 400 MHz. Also, a Bruker Avance 400 spectrometer at ambient temperature, using internal deuterium lock and equipped with a double-resonance ($^1$H, $^{13}$C) BroadBand Observe (BBO) probe head was used. Chemical shifts (δ) are reported in parts per million (ppm).

Pharmacological Part

Biological Assays A

FGFR1 (Enzymatic Assay)

In a final reaction volume of 30 µL, FGFR1 (h) (25 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 5 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an $IC_{50}$ (M) and $pIC_{50}$ ($-\log IC_{50}$) value.

FGFR2 (Enzymatic Assay)

In a final reaction volume of 30 µL, FGFR2 (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 0.4 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an $IC_{50}$ (M) and $pIC_{50}$ ($-\log IC_{50}$) value.

FGFR3 (Enzymatic Assay)

In a final reaction volume of 30 µL, FGFR3 (h) (40 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 25 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an $IC_{50}$ (M) and $pIC_{50}$ ($-\log IC_{50}$) value.

FGFR4 (Enzymatic Assay)

In a final reaction volume of 30 µL, FGFR4 (h) (60 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 5 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature.

Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ ($-log\ IC_{50}$) value.

KDR (VEGFR2) (Enzymatic Assay)

In a final reaction volume of 30 μL, KDR (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 3 μM ATP in the presence of compound (1% DMSO final). After incubation for 120 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an $IC_{50}$ (M) and $pIC_{50}$ ($-log\ IC_{50}$) value.

Ba/F3-FGFR1 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR1-transfected cells. Cells were put in an incubator at 37° C. and 5% $CO_2$. After 24 hours, 10 μl of Alamar Blue solution (0.5 mM $K3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-log\ IC_{50}$) value.

As a counterscreen the same experiment was performed in the presence of 10 ng/ml murine IL3.

Ba/F3-FGFR3 (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR3-transfected cells. Cells were put in an incubator at 37° C. and 5% $CO_2$. After 24 hours, 10 μl of Alamar Blue solution (0.5 mM $K_3Fe(CN)_6$, 0.5 mM $KaFe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-log\ IC_{50}$) value.

As a counterscreen the same experiment was performed in the presence of 10 ng/ml murine IL3.

Ba/F3-KDR (Minus IL3 or Plus IL3) (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-KDR-transfected cells. Cells were put in an incubator at 37° C. and 5% $CO_2$. After 24 hours, 10 μl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-log\ IC_{50}$) value.

As a counterscreen the same experiment was performed in the presence of 10 ng/ml murine IL3.

Ba/F3-FGFR4 (Cellular Proliferation Assay)

In a 384 well plate, 100 nl of compound dilution in DMSO was sprayed before adding 50 μl cell culture medium (phenol red free RPMI-1640, 10% FBS, 2 mM L-Glutamine and 50 μg/ml Gentamycin) containing 20000 cells per well of Ba/F3-FGFR4-transfected cells. Cells were put in an incubator at 37° C. and 5% CO2. After 24 hours, 10 μl of Alamar Blue solution (0.5 mM $K3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a fluorescence plate reader.

In this assay, the inhibitory effect of different compound concentrations (range 10 μM to 0.1 nM) was determined and used to calculate an $IC_{50}$ (M) and $pIC_{50}$ ($-log\ IC_{50}$) value.

Data for the compounds of the invention in the above assays are provided in Table A1.

TABLE A1

| Co. No. | FGFR1 $pIC_{50}$ | FGFR2 $pIC_{50}$ | FGFR3 $pIC_{50}$ | FGFR4 $pIC_{50}$ | VEGFR2 (KDR) $pIC_{50}$ | BAF3-FGFR1 (MIN IL3) $pIC_{50}$ | BAF3-FGFR1 (PLUS IL3) $pIC_{50}$ | BAF3-FGFR3 (MIN IL3) $pIC_{50}$ | BAF3-FGFR3 (PLUS IL3) $pIC_{50}$ | BAF3-KDR (MIN IL3) $pIC_{50}$ | BAF3-KDR (PLUS IL3) $pIC_{50}$ | BAF3-FGFR4 $pIC_{50}$ |
|---|---|---|---|---|---|---|---|---|---|---|---|---|
| 1 | <6 | <6 | <5 | <5 | <6 | <5 | <5 | <5 | <5 | <5 | <5 | <5 |
| 2 | 6.1 | 6.3 | 6.6 | 5.9 | <6 | 5.2 | <5 | 5 | <5 | <5 | <5 | <5 |
| 3 | <6 | <6 | 5.8 | 5.2 | <6 | <5 | <5 | <5 | <5 | <5 | <5 | <5 |
| 4 | ~6.1 | 6.3 | 6.3 | <6 | <6 | <5 | <5 | <5 | <5 | <5 | <5 | <5 |
| 5 | <6 | <6 | <6 | <6 | <6 | <5 | <5 | <5 | <5 | <5 | <5 | <5 |
| 6 | 7.0 | 7.5 | 6.9 | ~6.3 | 6.6 | 5.2 | <5 | 5.2 | <5 | <5 | <5 | ~5 |
| 7 | 6.3 | 6.6 | 6.5 | <6 | <6 | 5.1 | <5 | 5 | <5 | <5 | <5 | <5 |
| 8 | 6.3 | 6.8 | 6.8 | <5 | <6 | <5 | <5 | <5 | <5 | <5 | <5 | <5 |
| 9 | 6.8 | 7.1 | 7.0 | 5.9 | 6.3 | <5 | <5 | ~5 | <5 | <5 | <5 | <5 |
| 10 | 6.8 | 6.9 | 7.2 | 6.2 | <6 | 5.1 | <5 | 5.1 | <5 | <5 | <5 | <5 |
| 14 | ~6.4 | 6.8 | 7.2 | 6.2 | <6 | 5.1 | <5 | 5.1 | <5 | <5 | <5 | <5 |

TABLE A1-continued

| Co. No. | FGFR 1 pIC$_{50}$ | FGFR 2 pIC$_{50}$ | FGFR 3 pIC$_{50}$ | FGFR 4 pIC$_{50}$ | VEGFR 2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FGFR 4 pIC$_{50}$ |
|---|---|---|---|---|---|---|---|---|---|---|---|---|
| 16 | <6 | <6 | 6.3 | 5.1 | <6 | <5 | <5 | <5 | <5 | <5 | <5 | <5 |
| 17 | <6 | ~6.1 | 6.1 | 5.3 | <6 | <5 | <5 | <5 | <5 | <5 | <5 | <5 |
| 18 | 6.1 | ~6.6 | 6.7 | 5.8 | 7.0 | <5 | <5 | ~5.1 | <5 | 5.3 | <5 | <5 |
| 20 | <5 | 5.8 | 5.6 | <5 | <5 | <5 | <5 | <5 | <5 | <5 | <5 | <5 |
| 21 | <5 | 5.3 | 5.5 | <5 | <5 | <5 | <5 | <5 | <5 | <5 | <5 | <5 |
| 23 | <6 | 6.0 | 5.9 | <5 | <6 | <5 | <5 | <5 | <5 | <5 | <5 | <5 |
| 24 | <5 | 5.0 | <5 | <5 | <5 | <5 | <5 | <5 | <5 | <5 | <5 | <5 |
| 25 | <5 | <5 | <5 | <5 | <5 | <5 | <5 | <5 | <5 | <5 | <5 | <5 |
| 12 | <6 | <6 | 5.9 | 5.1 | <6 | <5 | <5 | <5 | <5 | <5 | <5 | <5 |
| 26 | <5 | 5.3 | <5 | <5 | 5.6 | <5 | <5 | <5 | <5 | <5 | <5 | <5 |
| 13 | 7.1 | 7.3 | 7.8 | 6.6 | 6.2 | 5.3 | <5 | 5.7 | <5 | <5 | <5 | 5.0 |
| 11 | 6.2 | 6.6 | 6.7 | 5.7 | <6 | <5 | <5 | ~5.2 | <5 | <5 | <5 | <5 |
| 15 | 6.2 | 6.3 | 6.2 | 5.6 | <6 | <5 | <5 | <5 | <5 | <5 | <5 | <5 |

The invention claimed is:

1. A method for treating a subject suffering from, or being at risk of suffering from cancer, said method comprising administering to the subject a compound selected from the group consisting of a compound of formula (I-A) or (I-B)

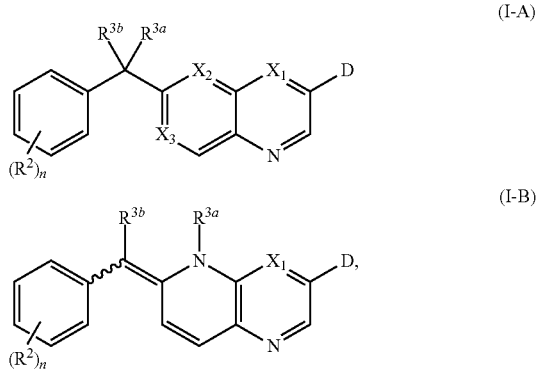

a tautomeric form, stereochemically isomeric form and isotopic form thereof, wherein
for (I-A)
$X_1$ is N, $X_2$ is N and $X_3$ is CH; or
$X_1$ is $CR^{3d}$, $X_2$ is N and $X_3$ is CH; or
$X_1$ is $CR^{3d}$, $X_2$ is $CR^{3d}$ and $X_3$ is N;
for (I-B)
$X_1$ is N or $CR^{3d}$;
each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo-$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy-$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —NR$^7$R$^8$, $C_{1-4}$alkoxy substituted with —C(=O)—NR$^7$R$^8$, $C_{1-4}$alkoxy substituted with —NR$^7$R$^8$, $C_{1-4}$alkoxy substituted with —C(=O)—NR$^7$R$^8$, —NR$^7$R$^8$ and —C(=O)—NR$^7$R$^8$; or when two $R^2$ groups are attached to adjacent carbon atoms they may be taken together to form a radical of formula:
—O—(C(R$^{17}$)$_2$)$_p$—O—;
—X—CH=CH—; or
—X—CH=N—; wherein R$^{17}$ represents hydrogen or fluorine, p represents 1 or 2 and X represents O or S;
D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more $R^1$ groups;
$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo-$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, —NR$^4$R$^5$, $C_{1-6}$alkyl substituted with —O—C(=O)—$C_{1-6}$alkyl, $C_{1-6}$alkyl substituted with —NR$^4$R$^5$, —C(=O)—NR$^4$R$^5$, —C(=O)—$C_{1-6}$alkyl-NR$^4$R$^5$, $C_{1-6}$alkyl substituted with —C(=O)—NR$^4$R$^5$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, R$^6$, $C_{1-6}$alkyl substituted with R$^6$, —C(=O)—R$^6$, $C_{1-6}$alkyl substituted with —C(=O)—R$^6$, hydroxy$C_{1-6}$alkyl substituted with R$^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;
R$^{3a}$ represents —NR$^{10}$R$^{11}$, hydroxyl, $C_{1-6}$alkoxy, hydroxy$C_{1-6}$alkoxy, $C_{1-6}$alkoxy substituted with —NR$^{10}$R$^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy- $C_{1-6}$alkyl-C(=O)—, $C_{1-6}$alkyl substituted with —O—C(=O)—$C_{1-6}$alkyl, $C_{1-6}$ alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$ alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)2; provided that for a compound of formula (I-B), $R^{3a}$ may not represent —$NR^{10}R^{11}$;

$R^{3b}$ represents hydrogen or hydroxyl; provided that if $R^{3a}$ represents —$NR^{10}R^{11}$, then $R^{3b}$ represents hydrogen; or for a compound of formula (I-A), $R^{3a}$ and $R^{3b}$ may also be taken together to form =O, to form =$NR^{10}$ to form cyclopropyl together with the carbon atom to which they are attached, to form =CH—$C_{0-4}$alkyl substituted with $R^{3c}$, or to form

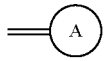

wherein ring A is a monocyclic 5 to 7 membered saturated heterocycle containing one heteroatom selected from N, O or S, said heteroatom not being positioned in alpha position of the double bond, wherein ring A is optionally being substituted with cyano, $C_{1-4}$alkyl, hydroxy$C_{1-4}$alkyl, H$_2$N—$C_{1-4}$alkyl, ($C_{1-4}$alkyl)NH—$C_{1-4}$alkyl, ($C_{1-4}$alkyl)$_2$N—$C_{1-4}$alkyl, (halo$C_{1-4}$alkyl)NH—$C_{1-4}$alkyl, $C_{1-4}$alkoxy$C_{1-4}$alkyl, —C(=O)—NH$_2$, —C(=O)—NH($C_{1-4}$alkyl), —C(=O)—N($C_{1-4}$alkyl)$_2$;

$R^{3c}$ represents hydrogen, hydroxyl, $C_{1-6}$alkoxy, $R^9$, —$NR^{10}R^{11}$, —C(=O)—$NR^{14}R^{15}$, cyano, —C(=O)—$C_{1-6}$alkyl or —CH(OH)—$C_{1-6}$alkyl;

$R^{3d}$ represents hydrogen, chlorine, hydroxyl, or $C_{1-6}$alkoxy;

$R^4$ and $R^5$ each independently represent hydrogen, $C_{1-6}$alkyl, $C_{1-6}$alkyl substituted with —$NR^{14}R^{15}$, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo$C_{1-6}$alkyl, —S(=O)$_2$—$NR^{14}R^{15}$, —C(=O)—$NR^{14}R^{15}$, —C(=O)—O—$C_{1-6}$alkyl, —C(=O)—$R^{13}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl substituted with $C_{1-4}$alkyl-O—C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O or S;

$R^{10}$ and $R^{11}$ each independently represent hydrogen, carboxyl, $C_{1-6}$alkyl, cyano$C_{1-6}$alkyl, $C_{1-6}$alkyl substituted with —$NR^{14}R^{15}$, $C_{1-6}$alkyl substituted with —C(=O)—$NR^{14}R^{15}$, halo$C_{1-6}$alkyl, hydroxy-$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy-$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo-$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with carboxyl, or $C_{1-6}$alkyl substituted with —NH—S(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, halo$C_{1-6}$alkyl, =O, cyano, —C(=O)—$C_{1-6}$alkyl, $C_{1-6}$alkoxy, or —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or —C(=O)$NR^{14}R^{15}$;

n independently represents an integer equal to 0, 1, 2, 3 or 4;

or an N-oxide thereof, a pharmaceutically acceptable salt thereof or a solvate thereof.

2. A method according to claim 1 wherein the compound is selected from the group consisting of a compound of formula (I-A), a tautomeric form, stereochemically isomeric form, and isotopic form thereof, or an N-oxide thereof, a pharmaceutically acceptable salt thereof or a solvate thereof.

3. A method according to claim 2 wherein the compound is selected from the group consisting of a compound of formula (I-A), a tautomeric form, stereochemically isomeric form, and isotopic form thereof, wherein $X_1$ is N, $X_2$ is N and $X_3$ is CH, or an N-oxide thereof, a pharmaceutically acceptable salt thereof or a solvate thereof.

4. A method according to claim 2 wherein the compound is selected from the group consisting of a compound of formula (I-A), a tautomeric form, stereochemically isomeric form, and isotopic form thereof, wherein $X_1$ is $CR^{3d}$, $X_2$ is N and $X_3$ is CH, or an N-oxide thereof, a pharmaceutically acceptable salt thereof or a solvate thereof.

5. A method according to claim 2 wherein the compound is selected from the group consisting of a compound of formula (I-A), a tautomeric form, stereochemically isomeric form, and isotopic form thereof, wherein $X_1$ is $CR^{3d}$, $X_2$ is $CR^{3d}$ and $X_3$ is N, or an N-oxide thereof, a pharmaceutically acceptable salt thereof or a solvate thereof.

6. A method according to claim 1 wherein the compound is selected from the group consisting of a compound of formula (I-B), a tautomeric form, stereochemically isomeric form, and isotopic form thereof, or an N-oxide thereof, a pharmaceutically acceptable salt thereof or a solvate thereof.

7. A method according to claim 6 wherein the compound is selected from the group consisting of a compound of formula (I-B), a tautomeric form, stereochemically isomeric form, and isotopic form thereof, wherein $X_1$ is $CR^{3d}$, or an N-oxide thereof, a pharmaceutically acceptable salt thereof or a solvate thereof.

8. A method according to claim 6 wherein the compound is selected from the group consisting of a compound of formula (I-B), a tautomeric form, stereochemically isomeric form, and isotopic form thereof, wherein $X_1$ is N, or an N-oxide thereof, a pharmaceutically acceptable salt thereof or a solvate thereof.

9. A method according to claim 1 wherein the compound is selected from the group consisting of a compound of formula (I-A) or (I-B), a tautomeric form, stereochemically isomeric form, and isotopic form thereof, wherein D is optionally substituted pyrazolyl, or an N-oxide thereof, a pharmaceutically acceptable salt thereof or a solvate thereof.

10. A method according to claim 1 wherein the compound is selected from the group consisting of a compound of formula (I-A) or (I-B), a tautomeric form, stereochemically isomeric form, and isotopic form thereof, wherein $R^2$ is independently selected from hydroxyl, halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, halo$C_{1-4}$alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ or —C(=O)—$NR^7R^8$, or an N-oxide thereof, a pharmaceutically acceptable salt thereof or a solvate thereof.

11. A method according to claim 10 wherein the compound is selected from the group consisting of a compound of formula (I-A) or (I-B), a tautomeric form, stereochemically isomeric form, and isotopic form thereof, wherein $R^2$ represents $C_{1-4}$alkoxy, or an N-oxide thereof, a pharmaceutically acceptable salt thereof or a solvate thereof.

12. A method according to claim 1 wherein the compound is selected from the group consisting of a compound of formula (I-A) or (I-B), a tautomeric form, stereochemically isomeric form, and isotopic form thereof, wherein $R^{3a}$ is hydroxyl, $C_{1-6}$alkyl, hydroxy$C_{1-6}$alkyl, hydroxy$C_{1-6}$alkoxy, $C_{1-6}$alkyl substituted with
—C(=O)—O—$C_{1-6}$alkyl, $C_{1-6}$alkyl substituted with $R^9$, or an N-oxide thereof, a pharmaceutically acceptable salt thereof or a solvate thereof.

13. A method according to claim 1 wherein the compound is selected from the group consisting of a compound of formula (I-A) or (I-B), a tautomeric form, stereochemically isomeric form, and isotopic form thereof, wherein $R^{3b}$ represents hydrogen or hydroxyl, or an N-oxide thereof, a pharmaceutically acceptable salt thereof or a solvate thereof.

14. A method according to claim 1 wherein the compound is selected from the group consisting of a compound of formula (I-A), a tautomeric form, stereochemically isomeric form, and isotopic form thereof, wherein $R^{3a}$ and $R^{3b}$ are taken together to form =O or to form =CH—$C_{0-4}$alkyl substituted with $R^{3c}$, or an N-oxide thereof, a pharmaceutically acceptable salt thereof or a solvate thereof.

15. A method according to claim 6 wherein the compound is selected from the group consisting of a compound of formula (I-B), a tautomeric form, stereochemically isomeric form, and isotopic form thereof, wherein $R^{3b}$ represents hydroxyl and $R^{3a}$ represents hydroxy$C_{1-6}$alkyl, or an N-oxide thereof, a pharmaceutically acceptable salt thereof or a solvate thereof.

16. A method according to claim 1 wherein the compound is selected from the group consisting of a compound of formula (I-A) or (I-B), a tautomeric form, stereochemically isomeric form, and isotopic form thereof, wherein n represents an integer equal to 1 or 2; and each $R^2$ represents hydroxyl or $C_{1-4}$alkoxy; $R^{3a}$ represents hydroxyl, hydroxy$C_{1-6}$alkyl, hydroxy$C_{1-6}$alkoxy, $C_{1-6}$alkyl, $C_{1-6}$alkyl substituted with $R^9$, $C_{1-6}$alkyl substituted with —C(=O)—O—$C_{1-6}$alkyl; or $R^{3a}$ and $R^{3b}$ are taken together to form =O, or to form =CH—$C_{0-4}$alkyl substituted with $R^{3c}$; $R^{3c}$ represents hydroxyl, cyano or —C(=O)—NR$^{14}$R$^{15}$; $R^{3b}$ represents hydrogen or hydroxyl; $R^{3d}$ represents hydrogen; D represents morpholinyl or pyrazolyl substituted with $C_{1-6}$alkyl; $R^9$ represents an optionally substituted 5 membered aromatic heterocycle, $R^{14}$ and $R^{15}$ each independently represent hydrogen or $C_{1-4}$alkyl, or an N-oxide thereof, a pharmaceutically acceptable salt thereof or a solvate thereof.

17. A method according to claim 1 wherein the compound is selected from the group consisting of a compound of formula (I-B), a tautomeric form, stereochemically isomeric form, and isotopic form thereof, wherein n represents an integer equal to 2; and each $R^2$ represents $C_{1-4}$alkoxy; $R^{3'}$ represents hydroxy$C_{1-6}$alkyl; $R^{3b}$ represents hydroxyl; $R^{3d}$ represents hydrogen; D represents pyrazolyl substituted with $C_{1-6}$alkyl, or an N-oxide thereof, a pharmaceutically acceptable salt thereof or a solvate thereof.

18. A method according to claim 1 comprising administering to the subject a compound selected from the group consisting of a compound of formula (I-A) or (I-B), a tautomeric form, stereochemically isomeric form and isotopic form thereof, or a pharmaceutically acceptable salt or solvate thereof.

19. A method for treating a subject suffering from, or being at risk of suffering from a carcinoma, wherein the carcinoma is selected from a carcinoma of the bladder, breast, colon, kidney, epidermis, liver, lung, esophagus, head and neck, gall bladder, ovary, pancreas, stomach, gastrointestinal (also known as gastric) cancer, cervix, endometrium, thyroid, prostate, or skin, a hematopoietic tumour of lymphoid lineage; a hematopoietic tumour of myeloid lineage; multiple myeloma; thyroid follicular cancer; a tumour of mesenchymal origin; a tumour of the central or peripheral nervous system; melanoma; seminoma; teratocarcinoma; osteosarcoma; xeroderma pigmentosum; keratoctanthoma; or Kaposi's sarcoma, said method comprising administering to the subject a compound selected from the group consisting of a compound of formula (I-A) or (I-B)

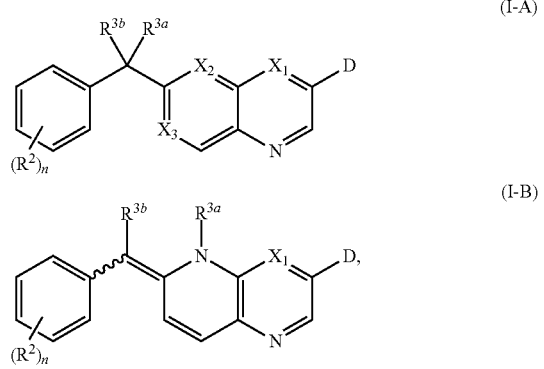

a tautomeric form, stereochemically isomeric form and isotopic form thereof, wherein for (I-A)
$X_1$ is N, $X_2$ is N and $X_3$ is CH; or
$X_1$ is CR$^{3d}$, $X_2$ is N and $X_3$ is CH; or
$X_1$ is CR$^{3d}$, $X_2$ is CR$^{3d}$ and $X_3$ is N;
for (I-B)
$X_1$ is N or CR$^{3d}$;
each $R^2$ is independently selected from hydroxyl, halogen, cyano, $C_{1-4}$alkyl, $C_{2-4}$alkenyl, $C_{2-4}$alkynyl $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo-$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy-$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —NR$^7$R$^8$, $C_{1-4}$alkyl substituted with —C(=O)—NR$^7$R$^8$, $C_{1-4}$alkoxy substituted with —NR$^7$R$^8$, $C_{1-4}$alkoxy substituted with —C(=O)—NR$^7$R$^8$, —NR$^7$R$^8$ and —C(=O)—NR$^7$R$^8$; or when two $R^2$ groups are attached to adjacent carbon atoms they may be taken together to form a radical of formula:
$C(R^{17})_2)_p$—O—;
—X—CH=CH—; or
—X—CH=N—; wherein $R^{17}$ represents hydrogen or fluorine, p represents 1 or 2 and X represents O or S;
D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more $R^1$ groups;
$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo-$C_{1-6}$alkyl, cyano$C_{1-4}$alkyl, $C_{1-6}$ alkoxy$C_{1-6}$alkyl wherein each $C_{1-6}$alkyl may optionally be substituted with one or two hydroxyl groups, —NR$^4$R$^5$, $C_{1-6}$alkyl substituted with —O—C(=O)—$C_{1-6}$alkyl, $C_{1-6}$alkyl substituted with —NR$^4$R$^5$, —C(=O)—NR$^4$R$^5$, —C(=O)—$C_{1-6}$alkyl-NR$^4$R$^5$, $C_{1-6}$alkyl substituted with —C(=O)—NR$^4$R$^5$, —S(=O)$_2$—$C_{1-6}$alkyl, —S(=O)$_2$-halo$C_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}$R$^{15}$, $R^6$, $C_{1-6}$alkyl substituted with $R^6$, —C(=O)—$R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;
$R^{3a}$ represents —NR$^{10}$R$^{11}$, hydroxyl, $C_{1-6}$alkoxy, hydroxy$C_{1-6}$alkoxy, $C_{1-6}$alkoxy substituted with —NR$^{10}$R$^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy-$C_{1-6}$alkyl-C(=O)—, $C_{1-6}$alkyl substituted with —O—C(=O)—$C_{1-6}$alkyl, $C_{1-6}$ alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$ alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$; provided that for a compound of formula (I-B), $R^{3a}$ may not represent —$NR^{10}R^{11}$;

$R^{3b}$ represents hydrogen or hydroxyl; provided that if $R^{3a}$ represents —$NR^{10}R^{11}$, then $R^{3b}$ represents hydrogen; or for a compound of formula (I-A), $R^{3a}$ and $R^{3b}$ may also be taken together to form =O, to form =$NR^{10}$ to form cyclopropyl together with the carbon atom to which they are attached, to form =CH—$C_{0-4}$alkyl substituted with $R^{3c}$, or to form

wherein ring A is a monocyclic 5 to 7 membered saturated heterocycle containing one heteroatom selected from N, O or S said heteroatom not being positioned in alpha position of the double bond, wherein ring A is optionally being substituted with cyano, $C_{1-4}$alkyl, hydroxy$C_{1-4}$alkyl, $H_2N$—$C_{1-4}$alkyl, ($C_{1-4}$alkyl)NH—$C_{1-4}$alkyl, ($C_{1-4}$alkyl)$_2$N—$C_{1-4}$alkyl, (halo$C_{1-4}$alkyl)NH—$C_{1-4}$alkyl, $C_{1-4}$alkoxy$C_{1-4}$alkyl, —C(=O)—$NH_2$, —C(=O)—NH($C_{1-4}$alkyl), —C(=O)—N($C_{1-4}$alkyl)$_2$;

$R^{3c}$ represents hydrogen, hydroxyl, $C_{1-6}$ alkoxy, $R^9$, —$NR^{10}R^{11}$, —C(=O)—$NR^{14}R^{15}$, cyano, —C(=O)—$C_{1-6}$alkyl or —CH(OH)—$C_{1-6}$alkyl;

$R^{3d}$ represents hydrogen, chlorine, hydroxyl, or $C_{1-6}$ alkoxy;

$R^4$ and $R^5$ each independently represent hydrogen, $C_{1-6}$alkyl, $C_{1-6}$alkyl substituted with —$NR^{14}R^{15}$, hydroxy$C_{1-6}$ halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo-$C_{1-6}$alkyl, —S(=O)$_2$—$NR^{14}R^{15}$, —C(=O)—$NR^{14}R^{15}$, —C(=O)—O—$C_{1-6}$alkyl, —C(=O)—$R^{13}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo-$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl substituted with —C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo-$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O or S;

$R^{10}$ and $R^{11}$ each independently represent hydrogen, carboxyl, $C_{1-6}$alkyl, cyano$C_{1-6}$alkyl, $C_{1-6}$alkyl substituted with —$NR^{14}R^{15}$, $C_{1-6}$alkyl substituted with —C(=O)—$NR^{14}R^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with carboxyl, or $C_{1-6}$alkyl substituted with —NH—S(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, halo$C_{1-6}$alkyl, =O, cyano, —C(=O)—$C_{1-6}$alkyl, $C_{1-6}$alkoxy, or —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono-or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or

—C(=O)$NR^{14}R^{15}$;

n independently represents an integer equal to 0, 1, 2, 3 or 4;

or an N-oxide thereof, a pharmaceutically acceptable salt thereof or a solvate thereof.

20. A method of inhibiting a FGFR kinase, which method comprises contacting the kinase with a kinase-inhibiting compound selected from the group consisting of a compound of formula (I-A) or (I-B)

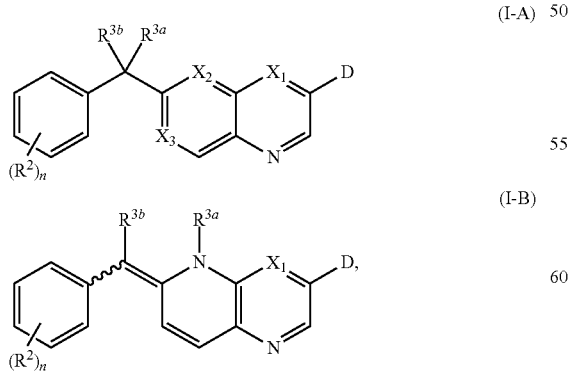

a tautomeric form, stereochemically isomeric form and isotopic form thereof, wherein for (I-A)
$X_1$ is N, $X_2$ is N and $X_3$ is CH; or
$X_1$ is $CR^{3d}$, $X_2$ is N and $X_3$ is CH; or
$X_1$ is $CR^{3d}$, $X_2$ is $CR^{3d}$ and $X_3$ is N;

for (I-B)
$X_1$ is N or $CR^{3d}$;

each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy-$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —$NR^7R^8$, $C_{1-4}$alkyl substituted with —C(=O)—$NR^7R^8$, $C_{1-4}$alkoxy substituted with —$NR^7R^8$, $C_{1-4}$alkoxy substituted with —C(=O)—$NR^7R^8$, —$NR^7R^8$ and —C(=O)—$NR^7R^8$; or when two $R^2$ groups are attached to adjacent carbon atoms they may be taken together to form a radical of formula:
—O–(C($R^{17}$)$_2$)$_p$—O—;
—X—CH=CH—, or
—X—CH=N—; wherein $R^{17}$ represents hydrogen or fluorine, p represents 1 or 2 and X represents O or S;

D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more $R^1$ groups;

$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo-$C_{1-6}$alkyl, cyano$C_{1-4}$alkyl, $C_{1-6}$ alkoxy$C_{1-6}$alkyl wherein each $C_{1-6}$alkyl may optionally be substituted with one or two hydroxyl groups, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, —C(=O)—$R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;

$R^{3a}$ represents —$NR^{10}R^{11}$, hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy-$C_{1-6}$alkyl-C(=O)—, $C_{1-6}$alkyl substituted with —O—C(=O)—$C_{1-6}$alkyl, $C_{1-6}$ alkoxy$C_{1-6}$alkyl wherein each $C_{1-6}$alkyl may optionally be substituted with one or two hydroxyl groups or with —O—C(=O)—$C_{1-6}$alkyl, $C_{2-6}$ alkenyl substituted with $C_{1-6}$ alkoxy, $C_{2-6}$ alkynyl substituted with $C_{1-6}$ alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$ substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$ $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$ $C_{1-6}$alkyl substituted with —$NR^{12}$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$; provided that for a compound of formula (I-B), $R^{3a}$ may not represent —$NR^{10}R^{11}$;

$R^{3b}$ represents hydrogen or hydroxyl; provided that if $R^{3a}$ represents —$NR^{10}R^{11}$, then $R^{3b}$ represents hydrogen; or for a compound of formula (I-A), $R^{3a}$ and $R^{3b}$ may also be taken together to form =O, to form =$NR^{10}$ to form cyclopropyl together with the carbon atom to which they are attached, to form =CH—$C_{1-4}$alkyl substituted with $R^{3c}$, or to form

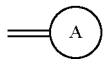

wherein ring A is a monocyclic 5 to 7 membered saturated heterocycle containing one heteroatom selected from N, O or S, said heteroatom not being positioned in alpha position of the double bond, wherein ring A is optionally being substituted with cyano, $C_{1-4}$alkyl, hydroxy$C_{1-4}$alkyl, $H_2N$—$C_{1-4}$alkyl, ($C_{1-4}$alkyl)NH—$C_{1-4}$alkyl, ($C_{1-4}$alkyl)$_2$N—$C_{1-4}$alkyl, (halo$C_{1-4}$alkyl)NH—$C_{1-4}$alkyl, $C_{1-4}$alkoxy-$C_{1-4}$alkyl, —C(=O)—$NH_2$, —C(=O)—NH($C_{1-4}$alkyl), —C(=O)—N($C_{1-4}$alkyl)$_2$;

$R^{3c}$ represents hydrogen, hydroxyl, $C_{1-6}$alkoxy, $R^9$, —$NR^{10}R^{11}$, —C(=)—$NR^{14}R^{15}$, cyano, —C(=O)—$C_{1-6}$alkyl or —CH(OH)—$C_{1-6}$alkyl;

$R^{3d}$ represents hydrogen, chlorine, hydroxyl, or $C_{1-6}$ alkoxy;

$R^4$ and $R^5$ each independently represent hydrogen, $C_{1-6}$alkyl, $C_{1-6}$alkyl substituted with —$NR^{14}R^{15}$, hydroxy$C_{1-6}$alkyl, halo$C_{1-6}$alkyl, hydroxyhalo-$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo-$C_{1-6}$alkyl, —S(=O)$_2$—$NR^{14}R^{15}$, —C(=O)—$NR^{14}R^{15}$, —C(=O)—O—$C_{1-6}$alkyl, —C(=O)—$R^{13}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo-$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl or $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O or S;

$R^{10}$ and $R^{11}$ each independently represent hydrogen, carboxyl, $C_{1-6}$alkyl, cyano$C_{1-6}$alkyl, $C_{1-6}$alkyl substituted with —NR$^{14}$R$^{15}$, C$_{1-6}$alkyl substituted with —C(=O)—NR$^{14}$R$^{15}$, haloC$_{1-6}$alkyl, hydroxyC$_{1-6}$alkyl, hydroxyhaloC$_{1-6}$alkyl, C$_{1-6}$ alkoxy, C$_{1-6}$alkoxyC$_{1-6}$alkyl wherein each C$_{1-6}$alkyl may optionally be substituted with one or two hydroxyl groups, R$^6$, C$_{1-6}$alkyl substituted with R$^6$, —C(=O)—R$^6$, —C(=O)—C$_{1-6}$alkyl,
—C(=O)-hydroxyC$_{1-6}$ alkyl, —C(=O)-haloC$_{1-6}$ alkyl, —C(=O)-hydroxyhaloC$_{1-6}$alkyl, C$_{1-6}$alkyl substituted with —Si(CH$_3$)$_3$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with carboxyl, or C$_{1-6}$alkyl substituted with —NH—S(=O)$_2$—NR$^{14}$R$^{15}$;

R$^{12}$ represents hydrogen or C$_{1-4}$alkyl optionally substituted with C$_{1-4}$alkoxy;

R$^{13}$ represents C$_{3-8}$cycloalkyl or a saturated 4 to 6-membered monocyclic heterocyclyl containing at least one heteroatom selected from N, O or S, wherein said C$_{3-8}$cycloalkyl or monocyclic heterocyclyl is optionally substituted with 1, 2 or 3 substituents each independently selected from halogen, hydroxyl, C$_{1-6}$alkyl, haloC$_{1-6}$alkyl, =O, cyano,
—C(=O)—C$_{1-6}$alkyl, C$_{1-6}$alkoxy, or —NR$^{14}$R$^{15}$;

R$^{14}$ and R$^{15}$ each independently represent hydrogen, or haloC$_{1-4}$alkyl, or C$_{1-4}$alkyl optionally substituted with a substituent selected from hydroxyl, C$_{1-4}$alkoxy, amino or mono-or di(C$_{1-4}$alkyl)amino;

R$^{16}$ represents hydroxyl, halogen, cyano, C$_{1-4}$alkyl, C$_{1-4}$alkoxy, —NR$^{14}$R$^{15}$ or
—C(=O)NR$^{14}$R$^{15}$;

n independently represents an integer equal to 0, 1, 2, 3 or 4;

or an N-oxide thereof, a pharmaceutically acceptable salt thereof or a solvate thereof.

\* \* \* \* \*

UNITED STATES PATENT AND TRADEMARK OFFICE
CERTIFICATE OF CORRECTION

PATENT NO. : 9,737,544 B2
APPLICATION NO. : 15/000304
DATED : August 22, 2017
INVENTOR(S) : Angibaud et al.

It is certified that error appears in the above-identified patent and that said Letters Patent is hereby corrected as shown below:

Column 132, Line 36, Claim 1: delete "$C_{1-6}$ alkoxy$C_{1-6}$alkyl" and insert -- $C_{1-6}$alkoxy$C_{1-6}$alkyl --

Column 133, Line 28, Claim 1: delete "-P(=O)(O$C_{1-6}$alkyl)2" and insert -- -P(=O)(O$C_{1-6}$alkyl)$_2$ --

Column 134, Line 45, Claim 1: delete "$C_{1-4}$alkyl substituted" and insert -- $C_{1-4}$alkyl-O-C(=O)-, $C_{1-4}$alkyl substituted --

Column 134, Line 46, Claim 1: delete "$C_{1-4}$alkoxy$C_{1-4}$alkyl" and insert -- $C_{1-4}$alkyl-C(=O)-, $C_{1-4}$alkoxy$C_{1-4}$alkyl --

Column 134, Line 51, Claim 1: delete "C(=O)-N$R^{14}R^{15}$, –S(=O)$_2$-$C_{1-4}$alkyl," and insert -- C(=O)-N$R^{14}R^{15}$, $C_{1-4}$alkoxy, –S(=O)$_2$-$C_{1-4}$alkyl, --

Column 138, Line 25, Claim 19: delete "C($R^{17}$)$_2$)$_p$-O-;" and insert -- -O-(C($R^{17}$)$_2$)$_p$-O-; --

Column 138, Line 38, Claim 19: delete "$C_{1-6}$ alkoxy$C_{1-6}$alkyl" and insert -- $C_{1-6}$alkoxy$C_{1-6}$alkyl --

Column 139, Line 4, Claim 19: delete "$C_{1-6}$ alkoxy$C_{1-6}$alkyl" and insert -- $C_{1-6}$alkoxy$C_{1-6}$alkyl --

Column 139, Lines 48-49, Claim 19: delete "N, O or S said" and insert -- N, O or S, said – --

Column 140, Line 22, Claim 19: delete "-C(=O)-N$R^{14}R^{15}$," and insert -- -N$R^{14}R^{15}$, -C(=O)-N$R^{14}R^{15}$, --

Column 140, Line 24, Claim 19: delete "N$R^{14}R^{15}$, S(=O)$_2$-$C_{1-6}$alkyl," and insert -- N$R^{14}R^{15}$, –S(=O)$_2$-$C_{1-6}$alkyl, --

Column 140, Line 45, Claim 19: delete "$C_{1-4}$alkyl substituted" and insert -- $C_{1-4}$alkyl-O-C(=O)-, $C_{1-4}$alkyl substituted --

Page 1 of 2

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,737,544 B2

Column 140, Line 46, Claim 19: delete "$C_{1-4}alkoxyC_{1-4}alkyl$ wherein" and insert -- $C_{1-4}alkyl-C(=O)-$, $C_{1-4}alkoxyC_{1-4}alkyl$ wherein --

Column 140, Line 49, Claim 19: delete "-$NR^{14}R^{15}$, $C_{1-4}alkyl$ substituted with" and insert -- -$NR^{14}R^{15}$, -$C(=O)-NR^{14}R^{15}$, $C_{1-4}alkyl$ substituted with --

Column 142, Line 8, Claim 20: delete "cyano, $C_{1-4}$ alkyl, $C_{2-4}alkenyl$," and insert -- cyano, $C_{1-4}alkyl$, $C_{2-4}alkenyl$, --

Column 142, Line 38, Claim 20: delete "$C_{1-6}$ $alkoxyC_{1-6}alkyl$" and insert -- $C_{1-6}alkoxyC_{1-6}alkyl$ --

Column 143, Line 4, Claim 20: delete "$C_{1-6}$ $alkoxyC_{1-6}alkyl$" and insert -- $C_{1-6}alkoxyC_{1-6}alkyl$ --

Column 143, Line 15, Claim 20: delete "-$NR^{10}R^{11}$ substituted" and insert -- -$NR^{10}R^{11}$, $C_{2-6}alkynyl$ substituted --

Column 143, Line 22, Claim 20: delete "-$S(=O)_2-C_{1-6}$" and insert -- -$S(=O)_2-C_{1-6}alkyl$, --

Column 143, Line 27, Claim 20: delete "$haloC_{1-6}$ $C_{1-6}alkyl$ substituted" and insert -- -$haloC_{1-6}alkyl$, $C_{1-6}alkyl$ substituted --

Column 143, Line 38, Claim 20: delete "$C_{1-4}alkyl$ substituted" and insert -- $C_{0-4}alkyl$ substituted --

Column 143, Line 56, Claim 20: delete "-$NR^{10}R^{11}$, -$C(=)-NR^{14}R^{15}$," and insert -- -$NR^{10}R^{11}$, -$C(=O)-NR^{14}R^{15}$, --

Column 144, Line 20, Claim 20: delete "-$C(=O)-NR^{14}R^{15}$," and insert -- -$NR^{14}R^{15}$, -$C(=O)-NR^{14}R^{15}$, --